United States Patent
Li et al.

(10) Patent No.: US 10,829,464 B2
(45) Date of Patent: Nov. 10, 2020

(54) BENZOHETEROCYCLIC ALKYLAMINE COMPOUNDS AND USE THEREOF

(71) Applicants: EAST CHINA UNIVERSITY OF SCIENCE AND TECHNOLOGY, Shanghai (CN); SHANGHAI INSTITUTE OF MATERIA MEDICA, CHINESE ACADEMY OF SCIENCES, Shanghai (CN)

(72) Inventors: Jian Li, Shanghai (CN); Lefu Lan, Shanghai (CN); Baoli Li, Shanghai (CN); Feifei Chen, Shanghai (CN); Shuaishuai Ni, Shanghai (CN); Yifu Liu, Shanghai (CN); Hanwen Wei, Shanghai (CN); Fei Mao, Shanghai (CN); Jin Zhu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 16/461,234

(22) PCT Filed: Nov. 17, 2017

(86) PCT No.: PCT/CN2017/111679
§ 371 (c)(1),
(2) Date: May 15, 2019

(87) PCT Pub. No.: WO2018/095287
PCT Pub. Date: May 31, 2018

(65) Prior Publication Data
US 2019/0315703 A1    Oct. 17, 2019

(30) Foreign Application Priority Data
Nov. 23, 2016    (CN) .......................... 2016 1 1037724

(51) Int. Cl.
| | | |
|---|---|---|
| *C07D 307/81* | (2006.01) |
| *A61P 31/04* | (2006.01) |
| *A61P 31/10* | (2006.01) |
| *C07D 307/82* | (2006.01) |
| *C07D 333/58* | (2006.01) |
| *C07D 409/12* | (2006.01) |

(52) U.S. Cl.
CPC ............ *C07D 307/81* (2013.01); *A61P 31/04* (2018.01); *A61P 31/10* (2018.01); *C07D 307/82* (2013.01); *C07D 333/58* (2013.01); *C07D 409/12* (2013.01)

(58) Field of Classification Search
CPC .................................................... C07D 307/81
See application file for complete search history.

(56) References Cited

U.S. PATENT DOCUMENTS

| | | |
|---|---|---|
| 4,680,291 A | 7/1987 | Hamberger et al. |
| 5,132,459 A | 7/1992 | Stuetz |

FOREIGN PATENT DOCUMENTS

| | | | |
|---|---|---|---|
| CN | 85109165 A | | 7/1986 |
| CN | 101379034 A | | 3/2009 |
| CN | 105566262 | * | 5/2015 |
| CN | 105272952 | * | 1/2016 |
| CN | 105272952 A | | 1/2016 |
| CN | 105566262 A | | 5/2016 |

* cited by examiner

*Primary Examiner* — Paul V Ward
(74) *Attorney, Agent, or Firm* — Lewis Roca Rothgerber Christie LLP

(57) ABSTRACT

Disclosed are benzoheterocyclic alkylamine compounds, or a pharmaceutically acceptable salt thereof, or a stereoisomer thereof, and a preparation method thereof, and use of the same in the manufacture of an antibacterial drug as an inhibitor of staphyloxanthin synthesis in *Staphylococcus aureus*.

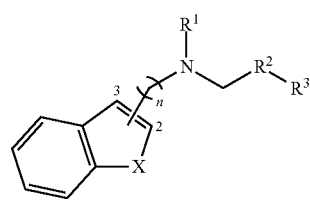

10 Claims, 3 Drawing Sheets

BENZOHETEROCYCLIC ALKYLAMINE COMPOUNDS AND USE THEREOF

CROSS-REFERENCE TO RELATED APPLICATION(S)

This application is a National Phase Patent Application of International Patent Application Number PCT/CN2017/111679, filed on Nov. 17, 2017, which claims priority of Chinese Patent Application No. 201611037724.9, filed Nov. 23, 2016. The entire contents of all of which are incorporated herein by reference.

TECHNICAL FIELD

The invention relates to the fields of medicinal chemistry and pharmacotherapeutics, and more particularly to benzoheterocyclic alkylamine compounds and the use thereof, and a method for preparing the same and the use thereof.

BACKGROUND ART

*Staphylococcus aureus* (SA) is the most common pathogen causing health care-associated infections worldwide. As a representative of Gram-positive bacteria, it is the most common pathogen causing human pyogenic infections, which can directly lead to local pyogenic infections, pneumonia, pseudomembranous colitis, pericarditis, meningitis, systemic infections such as septicemia, and sepsis. SA infections can be divided into hospital-acquired infection and community-acquired infection, the latter's finding increasing the potential biohazards of this pathogen and the possibility of an outbreak of infection.

At present, not only methicillin-resistant *Staphylococcus aureus* (MRSA) but also extremely high drug-resistant (XDR) and total drug-resistant (TDR) MRSAs have been discovered; even Vancomycin-intermediate and -resistant *Staphylococcus aureus* (VISA), Glycopeptide-intermediate and -resistant *Staphylococcus aureus* (GISA) and Vancomycin-resistant *Staphylococcus aureus* (VRSA) also have been discovered. MRSA is resistant to a variety of antibacterial agents, leading to difficulties in the treatment of infections, higher mortality, and a status being on the brink of "no cure", and causing serious difficulties in clinical treatment.

According to the U. S. Centers for Disease Control (CDC), about 100,000 people are hospitalized each year because of MRSA infections. It is imperative to develop new antibacterial agents against MRSA infections.

In summary, there is an urgent need in the art to develop new targets for antibacterial drug and novel antibacterial infection drugs, especially antibacterial drugs against staphyloxanthin synthesis.

CONTENTS OF THE INVENTION

It is an object of the invention to provide benzoheterocyclic alkylamine compounds, and the preparation method and use thereof.

In a first aspect, the invention provides a compound of Formula I, or a pharmaceutically acceptable salt thereof or a stereoisomer thereof:

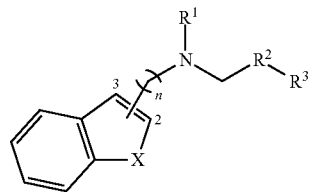

I in the formula:
X is S or O;
$R^1$ is H, a substituted or unsubstituted $C_1$-$C_4$ linear or branched alkyl;
$R^2$ is a substituted or unsubstituted $C_1$-$C_3$ linear alkyl, a substituted or unsubstituted $C_3$-$C_8$ cycloalkyl, a substituted or unsubstituted $C_2$-$C_6$ linear or branched alkenyl, —(CH=CH)-p, and a substituted or unsubstituted $C_2$-$C_6$ linear or branched alkynyl, wherein p is a positive integer from 2 to 5 (preferably 2 or 3); $R^3$ is a substituted or unsubstituted $C_1$-$C_3$ linear or branched alkyl, a substituted or unsubstituted $C_3$-$C_8$ cycloalkyl, a substituted or unsubstituted $C_3$-$C_7$ heteroaromatic ring group, and a substituted or unsubstituted $C_6$-$C_{10}$ aromatic ring group;
n is an integer from 1 to 3;
wherein, the group

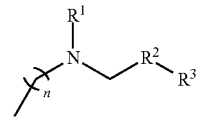

is located at position 2 or 3;
wherein, in $R^1$, $R^2$, and $R^3$, the substitution means having 1, 2, 3 or 4 substituents selected from the group consisting of a $C_1$-$C_6$ linear or branched alkyl, a $C_1$-$C_6$ haloalkyl, halogen, nitro, cyano, a $C_1$-$C_4$ linear or branched alkoxy, a —(C=O)—O—$C_1$-$C_4$ alkyl, a $C_6$-$C_{10}$ aromatic ring group, and a $C_3$-$C_8$ cycloalkyl.

In another preferred embodiment, the $C_6$-$C_{10}$ aromatic ring group is phenyl or naphthyl.

In another preferred embodiment, the $R^1$ is H, methyl, ethyl or isopropyl.

In another preferred embodiment, the $R^2$ is vinyl, cyclopropyl, ethynyl or (CH=CH)-p, wherein, p is a positive integer from 2 to 3.

In another preferred embodiment, the $R^3$ is a substituted $C_4$-$C_7$ cycloalkyl, a substituted $C_5$-$C_6$ heteroaromatic ring group, and a substituted $C_6$-$C_{10}$ aromatic ring group, the substitution means having 1, 2, 3 or 4 substituents selected from the group consisting of a $C_1$-$C_6$ alkyl, —$CF_3$, halogen, nitro, or a $C_1$-$C_4$ linear or branched alkoxy, and the number of substituents is an integer from 1 to 4.

In another preferred embodiment, the $R^3$ is a substituted $C_6$-$C_{10}$ aromatic ring group, and the substitution means having 1, 2, 3 or 4 substituents selected from the group consisting of halogen, trifluoromethyl, difluoromethyl, nitro, methoxy, a —(C=O)—O—$C_1$-$C_4$ alkyl, methyl or phenyl.

In another preferred embodiment, the substitution means having 1, 2, 3 or 4 substituents selected from the group consisting of a $C_1$-$C_3$ linear or branched alkyl, a $C_1$-$C_3$ perfluoroalkyl, a $C_1$-$C_3$ linear or branched alkoxy, halogen or nitro, and the number of substituents is an integer from 1 to 4.

In another preferred embodiment, the substitution means having 1, 2, 3 or 4 substituents selected from the group consisting of chlorine, bromine, methoxy, trifluoromethyl or nitro, and the number of substituents is an integer from 1 to 2.

In another preferred embodiment, the $R^3$ is a substituted phenyl, wherein the substitution means having 1, 2, 3 or 4 substituents selected from the group consisting of a $C_1$-$C_6$ alkyl group, a $C_1$-$C_6$ haloalkyl, a $C_1$-$C_6$ perfluoroalkyl and halogen.

In another preferred embodiment, the $R^3$ is a substituted phenyl, wherein the substitution means substitution by halogen or —$CF_3$.

In another preferred embodiment, the $R^3$ is a mono-substituted phenyl.

In another preferred embodiment, the $R^3$ is a bromo or trifluoromethyl substituted phenyl.

In another preferred embodiment, the compound of Formula I is selected from the group consisting of:

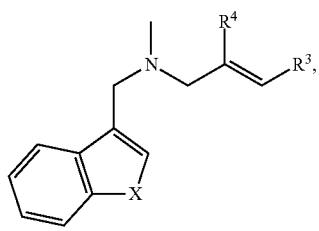

$I_A$

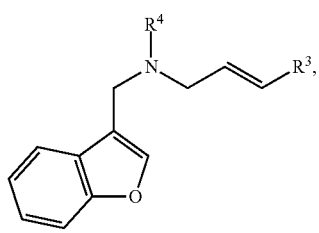

$I_B$

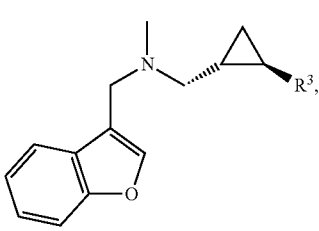

$I_C$

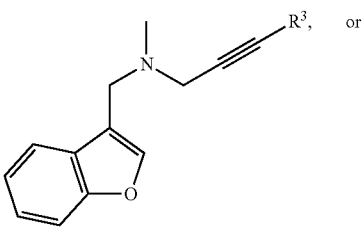

$I_D$, or

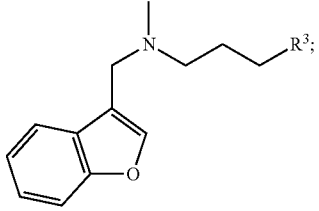

$I_E$

Wherein, X, $R^1$ and $R^3$ are as defined above, and $R^4$ is H, a substituted or unsubstituted $C_1$-$C_3$ linear alkyl.

In another preferred embodiment, the compound of Formula I is selected from the group consisting of:
(E)-N-methyl-N-[(benzofuran-3-yl)methylene]-3-phenyl-prop-2-en-1-amine;
(E)-N-methyl-N-[(benzofuran-3-yl)methylene]-3-(4-trifluoromethylphenyl)prop-2-en-1-amine;
(E)-N-methyl-N-[(benzofuran-3-yl)methylene]-3-(4-chlorophenyl)prop-2-en-1-amine;
(E)-N-methyl-N-[(benzofuran-3-yl)methylene]-3-(4-fluorophenyl)prop-2-en-1-amine;
(E)-N-methyl-N-[(benzofuran-3-yl)methylene]-3-(4-bromophenyl)prop-2-en-1-amine;
(E)-N-methyl-N-[(benzofuran-3-yl)methylene]-3-(4-difluoromethylphenyl)prop-2-en-1-amine;
(E)-N-methyl-N-[(benzofuran-3-yl)methylene]-3-(4-cyclopentyl)prop-2-en-1-amine;
(E)-N-methyl-N-[(benzofuran-3-yl)methylene]-3-(2-chlorophenyl)prop-2-en-1-amine;
(E)-N-methyl-N-[(benzofuran-3-yl)methylene]-3-(3-fluoro-4-trifluoromethylphenyl)prop-2-en-1-amine;
(E)-N-methyl-N-[(benzofuran-3-yl)methylene]-3-(naphthalen-1-yl)prop-2-en-1-amine;
(E)-N-methyl-N-[(benzofuran-3-yl)methylene]-3-(2,4-dichlorophenyl)prop-2-en-1-amine;
(E)-N-methyl-N-[(benzofuran-3-yl)methylene]-3-(3-chlorophenyl)prop-2-en-1-amine;
(E)-N-methyl-N-[(benzofuran-3-yl)methylene]-3-(4-methylcarboxylate phenyl)prop-2-en-1-amine;
(E)-N-methyl-N-[(benzofuran-3-yl)methylene]-3-(furan-2-yl)-prop-2-en-1-amine;
(E)-N-methyl-N-[(benzofuran-3-yl)methylene]-3-(4-methoxyphenyl)-prop-2-en-1-amine;
(E)-N-methyl-N-[(benzofuran-3-yl)methylene]-3-(4-nitrophenyl)-prop-2-en-1-amine;
(E)-N-methyl-N-[(benzofuran-3-yl)methylene]-3-(4-ethoxyphenyl)-prop-2-en-1-amine;
(E)-N-methyl-N-[(benzofuran-3-yl)methylene]-3-(3-trifluoromethylphenyl)-prop-2-en-1-amine;
(E)-N-methyl-N-[(benzofuran-3-yl)methylene]-3-(3-fluorophenyl)-prop-2-en-1-amine;
(E)-N-methyl-N-[(benzofuran-3-yl)methylene]-3-(3-methoxyphenyl)-prop-2-en-1-amine;
(E)-N-methyl-N-[(benzofuran-3-yl)methylene]-3-(4-methylphenyl)-prop-2-en-1-amine;
(E)-N-methyl-N-[(benzofuran-3-yl)methylene]-3-(2-nitrophenyl)-prop-2-en-1-amine;
(E)-N-methyl-N-[(benzofuran-3-yl)methylene]-but-2-en-1-amine;
(E)-N-methyl-N-[(benzofuran-3-yl)methylene]-3-(4-cyanophenyl)-prop-2-en-1-amine;
(E)-N-methyl-N-[(benzofuran-3-yl)methylene]-3-(4-phenylphenyl)-prop-2-en-1-amine;

(E)-N-methyl-N-[(benzofuran-3-yl)methylene]-3-(2-naphthyl)-prop-2-en-1-amine;
(E)-N-methyl-N-[(benzofuran-3-yl)methylene]-3-(4-tert-butylphenyl)-prop-2-en-1-amine;
(E)-N-methyl-N-[(benzofuran-3-yl)methylene]-3-(2-fluorophenyl)-prop-2-en-1-amine;
(E)-N-methyl-N-[(benzofuran-3-yl)methylene]-3-(3-nitrophenyl)-prop-2-en-1-amine;
(E)-N-methyl-N-[(benzofuran-3-yl)methylene]-3-(2-trifluoromethyphenyl)-prop-2-en-1-amine;
(E)-N-methyl-N-[(benzofuran-3-yl)methylene]-3-(2-fluoro-4-trifluoromethylphenyl)-prop-2-en-1-amine;
(E)-N-methyl-N-[(benzofuran-3-yl)methylene]-3-cyclopentylprop-2-en-1-amine;
(E)-N-methyl-N-[(benzofuran-3-yl)methylene]-3-thiophen-2-en-1-amine;
(E)-N-methyl-N-[(benzofuran-3-yl)methylene]-3-(2-methoxyphenyl)-prop-2-en-1-amine;
(E)-N-methyl-N-[(benzofuran-3-yl)methylene]-3-(2-fluoro-4-methoxyphenyl)-prop-2-en-1-amine;
(E)-N-methyl-N-[(benzofuran-3-yl)methylene]-3-(2-methylphenyl)-prop-2-en-1-amine;
(E)-N-methyl-N-[(benzofuran-3-yl)methylene]-3-(3-methylphenyl)-prop-2-en-1-amine;
(E)-N-methyl-N-[(benzofuran-3-yl)methylene]-3-(3-fluoro-4-methoxyphenyl)-prop-2-en-1-amine;
(E)-N-methyl-N-[(benzothiophen-3-yl)methylene]-3-(3-fluoro-4-methoxyphenyl)-prop-2-en-1-amine;
(E)-N-[(benzofuran-3-yl)methylene]-3-(4-trifluoromethylphenyl)-prop-2-en-1-amine;
(E)-N-ethyl-N-[(benzofuran-3-yl)methylene]-3-(4-trifluoromethylphenyl)-prop-2-en-1-amine;
(E)-N-isopropyl-N-[(benzofuran-3-yl)methylene]-3-(4-trifluoromethylphenyl)-prop-2-en-1-amine;
N-methyl-N-[(benzofuran-7-yl)methylene]-1-[(1S,2S)-2-phenylcyclopropyl]-methylamine;
N-methyl-N-[(6,7,8,9-tetrahydro-5H-benzo[3]annulen-2-yl)methyl]-3-(4-phenylphenyl)-prop-2-yn-1-amine;
N-methyl-N-[(6,7,8,9-tetrahydro-5H-benzo[3]annulen-2-yl)methylene]-3-phenyl-prop-1-amine;
(E)-N-methyl-N-[(benzofuran-2-yl)methylene]-3-(4-phenylphenyl)-prop-2-en-1-amine;
(E)-N-methyl-N-[(benzothiophen-2-yl)methylene]-3-(4-phenylphenyl)-prop-2-en-1-amine.

In a second aspect, the invention provides a pharmaceutical composition comprising: (1) the compound, or a pharmaceutically acceptable salt thereof, or a stereoisomer thereof according to the first aspect of the invention as an active ingredient; and
(2) a pharmaceutically acceptable carrier.

In another preferred embodiment, the pharmaceutical composition also contains an additional antibiotic.

In another preferred embodiment, the pharmaceutically acceptable salt is a hydrochloride.

In a third aspect, the invention provides an antibacterial drug comprising:
(1) the compound, or a pharmaceutically acceptable salt thereof, or a stereoisomer thereof according to the first aspect of the invention;
(2) an additional antibiotic; and
(3) a pharmaceutically acceptable carrier.

In a fourth aspect, the invention provides use of the compound, or a pharmaceutically acceptable salt thereof, or a stereoisomer thereof according to the first aspect of the invention in the preparation of a preparation or a medicament for:

(1) inhibiting staphyloxanthin synthesis in *Staphylococcus aureus*; and/or
(2) inhibiting a key enzyme CrtN during staphyloxanthin synthesis in *Staphylococcus aureus*; and/or
(3) inhibiting or killing *Staphylococcus aureus*; and/or
(4) treating infectious diseases caused by *Staphylococcus aureus*.

In another preferred embodiment, the *Staphylococcus aureus* comprises MRSA.

In another preferred embodiment, the medicament is a drug against *Staphylococcus aureus*.

It is to be understood that within the scope of the invention, the various technical features of the invention described above and the various technical features specifically described hereinafter (such as in the examples) may be combined with each other to form a new or preferred technical solution. Limited by space, they will not be further described herein.

SPECIFIC EMBODIMENTS

Figure 1:
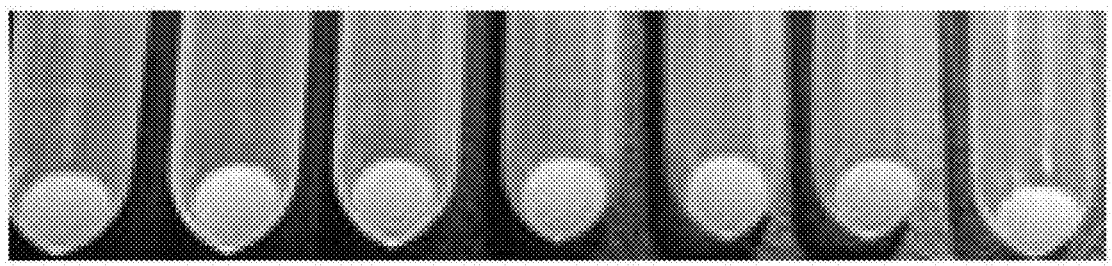
FIG. 1 shows the final photograph of inhibition of staphyloxanthin synthesis by Compound $I_A$-25 of the invention, with the concentrations of 50 μM, 10 μM, 5 μM, 2.5 μM, 1.25 μM, 0.625 μM, 0.3125 μM, and 0 μM from left to right successively and the colors of white to yellow from left to right gradually.

Through an extensive and intensive research, the inventors have unexpectedly discovered a novel inhibitor of *Staphylococcus aureus*, and the preparation method and use thereof for the first time. The invention was completed on the basis of this finding.

Terminology

All technical and scientific terms used herein have the same meaning as commonly understood by one of ordinary skill in the art to which the invention belongs, unless otherwise defined.

As used herein, when used in reference to a particularly recited value, the term "about" means that the value can vary by no more than 1% from the recited value. For example, as used herein, the expression "about 100" includes all values between 99 and 101 (e.g., 99.1, 99.2, 99.3, 99.4, etc.).

As used herein, the terms "containing" or "including (comprising)" may be open, semi-closed, and closed. In other words, the terms also include "consisting essentially of . . . ", or "consisting of . . . ".

The following terms used in the specification and claims have the meanings commonly understood by those skilled in the art, unless otherwise defined. All patents, patent applications, and publications cited herein are incorporated herein by reference in their entirety, unless otherwise stated.

It is to be understood that both the foregoing general description and the following detailed description are exemplary and explanatory only, and are not any restrictive of the invention. In the present application, the use of the singular also includes the plural unless otherwise specified. It must be noted that the singular forms used in the specification and claims include the plural forms of the indicated, unless otherwise indicated obviously in the text. It should also be noted that "or" is used to mean "and/or", unless otherwise indicated. Furthermore, the terms "containing" or "including (comprising)" may be open, semi-closed, and closed. In other words, the terms also include "consisting essentially of . . . ", or "consisting of . . . ".

The standard definitions of chemical terms can be found in references (including Carey and Sundberg "ADVANCED ORGANIC CHEMISTRY 4TH ED." Vols. A (2000) and B (2001), Plenum Press, New York). Conventional methods within the skill of the art, such as mass spectrometry, NMR, IR and UV/VIS spectroscopy and pharmacological methods, are employed, unless otherwise indicated. Unless specifically defined, the terms used herein in the descriptions of analytical chemistry, organic synthetic chemistry, and pharmaceutical and pharmaceutical chemistry are known in the art. Standard techniques can be used in chemical synthesis, chemical analysis, pharmaceutical preparation, formulation and delivery, and treatment of patients. For example, the reaction and purification can be carried out using the manufacturer's instructions for use of the kit, or in a manner well known in the art or according to the descriptions of the invention. The above techniques and methods can generally be carried out according to conventional methods well known in the art, as described in the various summaries and more specific references cited and discussed in this specification. In the present specification, the groups and their substituents can be selected by those skilled in the art to provide stable structural moieties and compounds.

When a substituent is described by a conventional chemical formula written from left to right, the substituent also includes the chemically equivalent substituent obtained when the structural formula is written from right to left. For example, —$CH_2O$— is equivalent to —$OCH_2$—.

The section headings used herein are for the purpose of organizing article only, and are not to be construed as limiting the subject matter. All documents or parts of the documents cited in this application, including but not limited to patents, patent applications, articles, books, operating manuals and papers, are incorporated herein by reference in their entirety.

Certain chemical groups defined herein are preceded by a simplified symbol to indicate the total number of carbon atoms present in the groups. For example, a $C_1$-$C_6$ alkyl refers to an alkyl as defined below having a total of from 1 to 6 carbon atoms. The total number of carbon atoms in the simplified symbol does not include carbon that may be present in the substituents of the group.

In addition to the foregoing, when used in the specification and claims of the present application, the following terms have the meanings indicated below, unless otherwise specifically indicated.

In the present application, the term "halogen" refers to fluorine, chlorine, bromine or iodine.

"Hydroxyl" refers to —OH group.

"Nitro" refers to —$NO_2$.

In the present application, as a group or a part of other group (for example, in a group such as a halogen-substituted alkyl, etc.), the term "alkyl" means a fully saturated linear or branched hydrocarbon chain group, consisting only of carbon atoms and hydrogen atoms, for example, having, for example, from 1 to 7 carbon atoms, and being linked to the remainder of the molecule by a single bond, which includes, for example, but not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl and the like.

In the present application, the term "alkenyl" as a group or a part of other group means a linear or branched hydrocarbon chain group consisting only of carbon atoms and hydrogen atoms, containing at least one double bond, having, for example, from 2 to 8 (preferably 2 to 6) carbon atoms and being linked to the remainder of the molecule by a single bond, which includes, for example, but not limited to, ethenyl, propenyl, allyl, but-1-enyl, but-2-enyl, pent-1-enyl, pent-1,4-dienyl and the like. As used herein, "a $C_2$-$C_6$ linear or branched alkenyl" includes a single double bond, or multiple discrete double bonds.

In the present application, the term "alkynyl" as a group or a part of other group means a linear or branched hydrocarbon chain group consisting only of carbon atoms and hydrogen atoms, containing at least one triple bond, optionally containing at least one double bond, having, for example, from 2 to 6 carbon atoms and being linked to the remainder of the molecule by a single bond, which includes, for example, but not limited to, ethynyl, prop-1-ynyl, but-1-ynyl, pent-1-en-4-ynyl and the like. As used herein, "a $C_2$-$C_6$ linear or branched alkynyl" includes a single triple bond, or a plurality of discrete triple bonds.

In the present application, the term "aryl" as a group or a part of other group means a conjugated hydrocarbon ring system group having from 6 to 18 (preferably from 6 to 10) carbon atoms. For the purposes of the invention, the aryl may be a monocyclic, bicyclic, tricyclic or more cyclic ring system, and may also be fused to the cycloalkyl or heterocyclic group as defined above, provided that the aryl is linked to the remainder of the molecule by a single bond via an atom on the aromatic ring. Examples of aryl include, but are not limited to, phenyl, naphthyl, anthryl, phenanthryl, fluorenyl, and the like.

In the present application, the term "heteroaryl" as a group or a part of other group means a 5- to 16-membered conjugated ring system group having from 1 to 15 (preferably from 1 to 10) carbon atoms and 1 to 6 heteroatoms selected from nitrogen, oxygen and sulfur within the ring.

Unless otherwise specifically indicated in the specification, the heteroaryl may be a monocyclic, bicyclic, tricyclic or more cyclic ring system, and may also be fused to the cycloalkyl or heterocyclic groups as defined above, provided that the aryl is linked to the remainder of the molecule by a single bond via an atom on the aromatic ring. The nitrogen, carbon or sulfur atom in the heteroaryl can be optionally oxidized; and the nitrogen atom can optionally be quaternized.

For the purposes of the invention, the heteroaryl is preferably a stable 5- to 12-membered aromatic group containing from 1 to 5 heteroatoms selected from nitrogen, oxygen and sulfur, more preferably a stable 5- to 10-membered aromatic group containing from 1 to 4 heteroatoms selected from nitrogen, oxygen, and sulfur or a 5- to 6-membered aromatic group containing from 1 to 3 heteroatoms selected from nitrogen, oxygen, and sulfur. Examples of the heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolyl, isoquinolyl, diazanaphthyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxatriazolyl, cinnolinyl, quinazolinyl, phenylthio, indolizinyl, phenanthrolinyl, isoxazolyl, phenoxazinyl, phenothiazinyl, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, and the like.

In the present application, "optionally" or "optional" means that the subsequently described event or condition may or may not occur, and that the description includes both the occurrence and non-occurrence of the event or condition. For example, "a optionally substituted aryl" means that the aryl is substituted or unsubstituted, and the description includes both a substituted aryl and a unsubstituted aryl. The "optional" substituents described in the claims and the specification of the invention are selected from the group consisting of alkyl, alkenyl, alkynyl, halogen, haloalkyl, haloalkenyl, haloalkynyl, cyano, nitro, an optionally substituted aryl, an optionally substituted heteroaryl, an optionally substituted cyclic hydrocarbon group, an optionally substituted heterocyclic hydrocarbon group.

The terms "moiety," "structural moiety," "chemical moiety," "group," and "chemical group", as used herein, refer to a particular fragment or functional group in a molecule. A chemical moiety is generally considered to be a chemical entity that is embedded or attached to a molecule.

When the compound of the invention contains an olefinic double bond, the compound of the invention are intended to include the E- and Z-geometric isomers, unless otherwise stated.

In the present application, the term "pharmaceutically acceptable salt" includes pharmaceutically acceptable acid addition salts and pharmaceutically acceptable base addition salts.

The "pharmaceutically acceptable acid addition salt" means a salt formed with an inorganic or organic acid, which is capable of retaining the bioavailability of the free base without any other side effects. The inorganic acid salts include, but are not limited to, hydrochlorides, hydrobromides, sulfates, nitrates, phosphates, and the like; the organic acid salts include, but are not limited to, formates, acetates, 2,2-dichloroacetates, trifluoroacetates, propionates, hexanoates, octoates, decanoates, undecylenates, glycolates, gluconates, lactates, sebacates, adipates, glutarates, malonates, oxalates, maleates, succinates, fumarates, tartrates, citrates, palmitates, stearates, oleates, cinnamates, laurates, malates, glutamates, pyroglutamates, aspartates, benzoates, methanesulfonates, besylates, p-toluenesulfonates, alginates, ascorbates, salicylates, 4-aminosalicylates, naphthalene disulfonates, and the like. These salts can be prepared by methods known in the art.

The "pharmaceutically acceptable base addition salt" refers to a salt formed with an inorganic or organic base, which is capable of retaining the bioavailability of the free acid without other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium salts, sodium salts, potassium salts, calcium salts and magnesium salts. Salts derived from organic bases include, but are not limited to, the following salts of: primary amines, secondary amines and tertiary amines, substituted amines, including naturally substituted amines, cyclic amines, and basic ion exchange resins, for example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline, and caffeine. These salts can be prepared by methods known in the art.

In the present application, "a pharmaceutical composition" refers to a formulation of the compound of the invention and a medium generally accepted in the art for delivery of a biologically active compound to a mammal (such as human). The medium includes a pharmaceutically acceptable carrier. The purpose of the pharmaceutical composition is to promote the administration of an organism, thereby facilitating the absorption of an active ingredient and thereby exerting biological activity.

The term "pharmaceutically acceptable" as used herein, refers to a substance (such as a carrier or diluent) that does not affect the biological activity or properties of the compound of the invention, and is relatively non-toxic, i.e., the substance can be administered to an individual without causing undesirable biological reactions or interacting with any of the components contained in the composition in an undesirable manner.

In the present application, "pharmaceutically acceptable excipients" include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant administrative departments of government for acceptable use by human or livestock.

The terms "prophylactic", "prevention" and "preventing" as used herein include reducing the possibility of occurrence or progression of a disease or condition in a patient.

The term "treatment" and other similar synonyms as used herein include the following meanings:

(i) preventing a disease or condition from occurring in mammals, particularly when such mammals are susceptible to the disease or condition, but have not been diagnosed as having the disease or condition;

(ii) inhibiting a disease or condition, i.e., suppressing its development;

(iii) alleviating a disease or condition, i.e., causing the state of the disease or condition to regress; or (iv) relieving the symptoms caused by a disease or condition.

The term "effective amount," "therapeutically effective amount," or "pharmaceutically effective amount," as used herein, refers to an amount of at least one agent or compound that is sufficient to alleviate one or more symptoms of the disease or condition being treated to some extent upon administration. The results can be regression and/or alleviation of signs, symptoms or causes, or any other desired changes in the biological system. For example, an "effective amount" for treatment is an amount of a composition comprising the compound disclosed herein that is required to provide a significant relief effect of a condition clinically.

An effective amount suitable for any individual case can be determined using techniques such as a dose escalation trial.

The terms "taking," "administering," "administration" and the like, as used herein, refer to a method of delivering a compound or composition to a desired site for biological action. These methods include, but are not limited to, oral routes, duodenal routes, parenteral injections (including intravenous, subcutaneous, intraperitoneal, intramuscular, intraarterial injection or infusion), topical administration, and rectal administration. The techniques of administration of the compounds and methods described herein are well known to those skilled in the art, for example, those discussed in "Goodman and Gilman, The Pharmacological Basis of Therapeutics, current ed.; Pergamon; and Remington's, Pharmaceutical Sciences (current edition), Mack Publishing Co., Easton, Pa". In a preferred embodiment, the compounds and compositions discussed herein are administered orally.

The terms "pharmaceutical combination", "drug combination", "combined medication", "administering other treatments", "administering other therapeutic agents" and the like, as used herein, refer to a drug treatment obtained by mixing or combining more than one active ingredient, including fixed and unfixed combinations of active ingredients. The term "fixed combination" refers to the simultaneous administration of at least one compound described herein and at least one synergistic agent to a patient in the form of a single entity or a single dosage form. The term "unfixed combination" refers to the simultaneous, combinational or sequential administration at variable intervals of at least one of the compounds described herein and at least one synergistic preparation to the patient in the form of separate entities.

The invention has the main advantages of:
1. providing a compound of Formula I having a novel benzoheterocyclic alkylamine structure;
2. providing a inhibitor of *Staphylococcus aureus* having novel structure and the preparation method and use thereof, and the inhibitor has a higher inhibitory activity on staphyloxanthin, targeting a key enzyme CrtN in the synthesis process of staphyloxanthin; most of the compounds of the invention have potent inhibitory activity against staphyloxanthin synthesis, and have very strong inhibitory activity against staphyloxanthin in drug-resistant bacteria (*S. aureus* USA400MW2, USA300LAC, and Mu50); and
3. providing a class of pharmaceutical compositions for treating the diseases associated with the activity of *Staphylococcus aureus*.

The invention is further illustrated below in conjunction with the specific examples. It is to be understood that these examples are used for illustrating the invention only, and not intended to limit the scope of the invention. The experimental methods in the following examples which do not specify the specific conditions usually follow conventional conditions or the conditions recommended by the manufacturer. Unless otherwise stated, the percentages and parts are weight percentages and parts by weight.

The experimental materials and reagents used in the following examples are obtained from commercially available sources unless otherwise specified.

Compounds of Formula I In a preferred embodiment of the invention, the benzofuran-3-alkylamine compounds, the compounds of Formula I are selected from the group consisting of the following compounds, or their salts formed with a pharmaceutically acceptable acid or base:

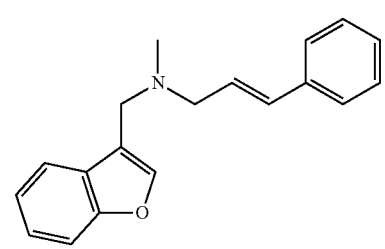

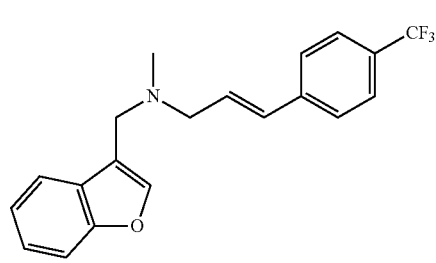

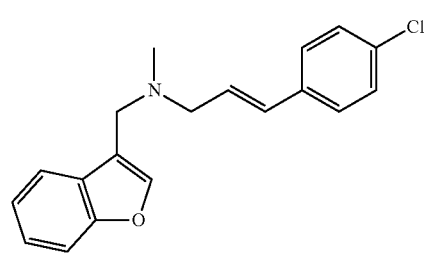

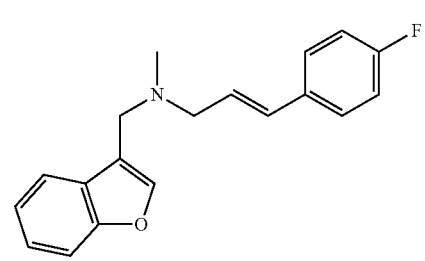

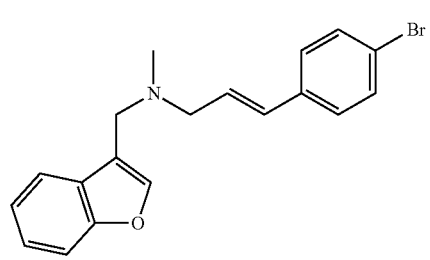

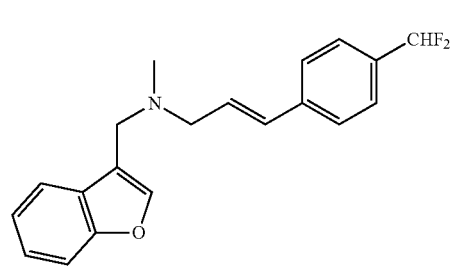

-continued
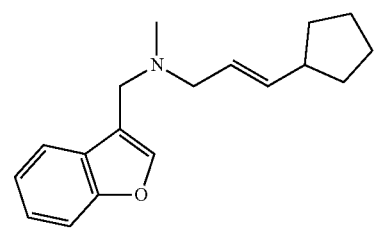
I$_A$-7
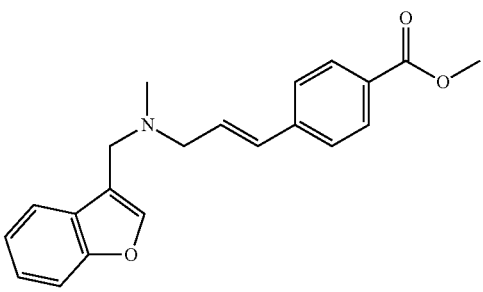
I$_A$-13
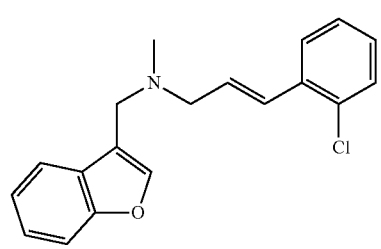
I$_A$-8
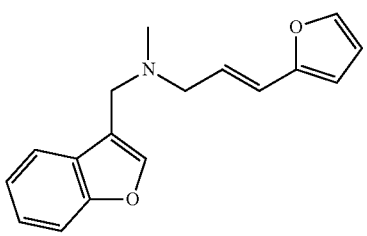
I$_A$-14
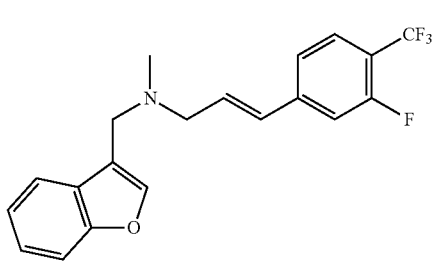
I$_A$-9
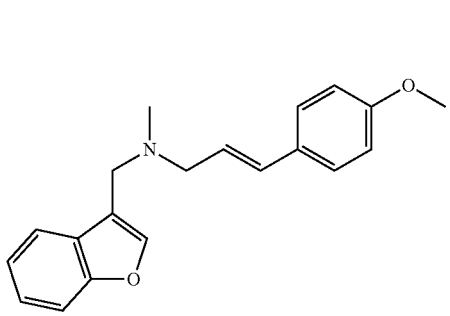
I$_A$-15
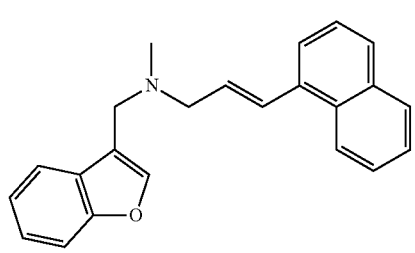
I$_A$-10
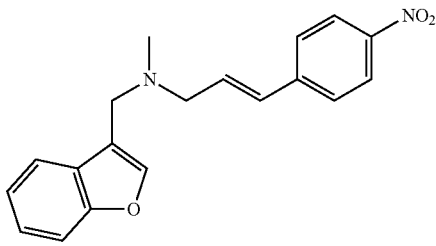
I$_A$-16
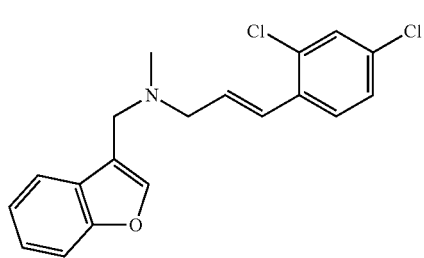
I$_A$-11
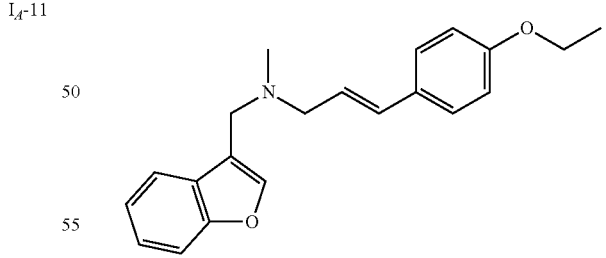
I$_A$-17
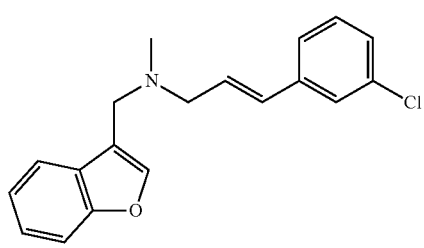
I$_A$-12
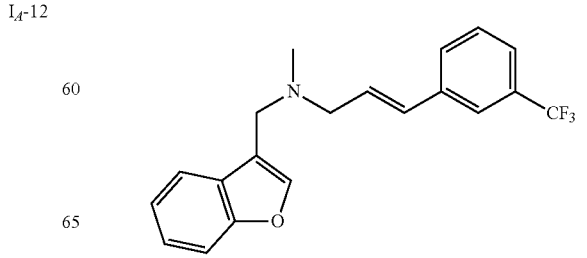
I$_A$-18

-continued
I_A-19
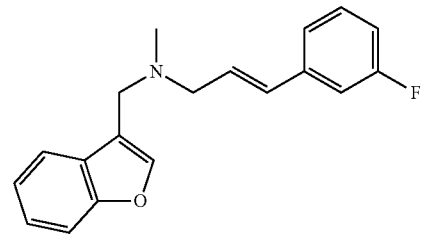
I_A-20
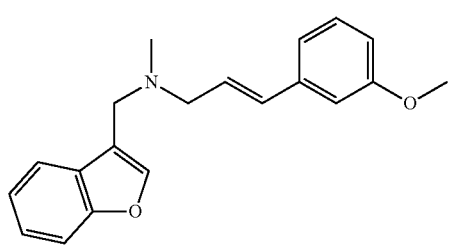
I_A-21
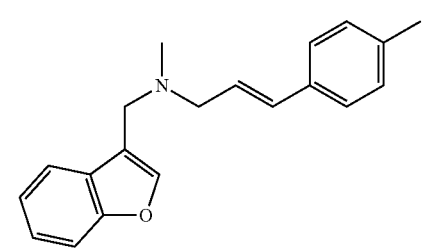
I_A-22
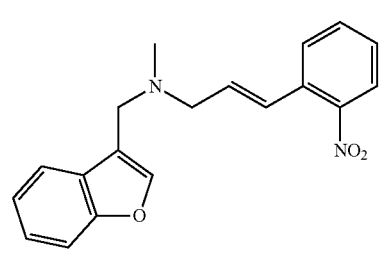
I_A-23
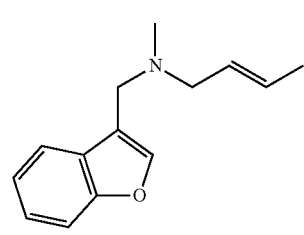
I_A-24
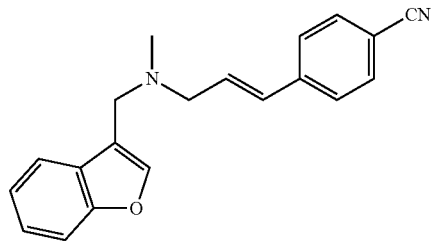
-continued
I_A-25
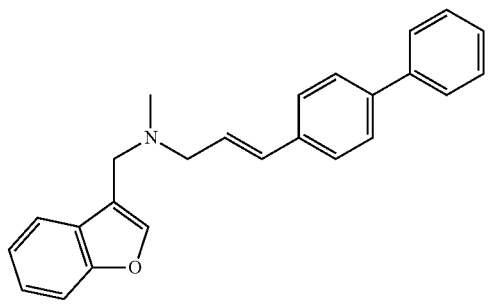
I_A-26
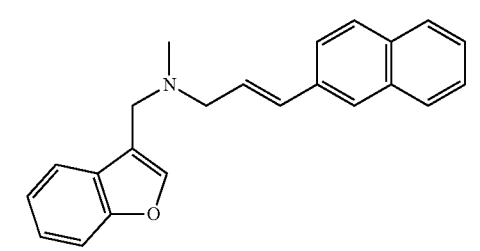
I_A-27
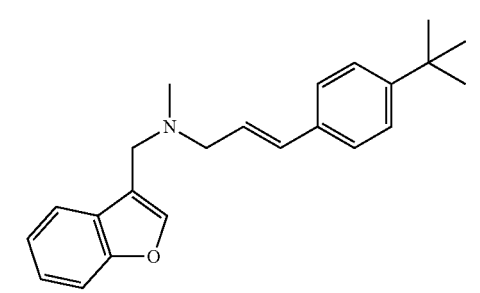
I_A-28
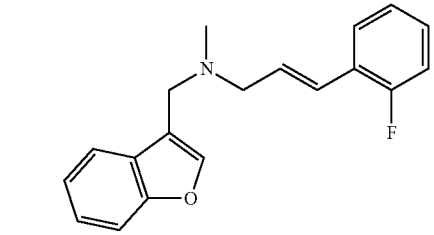
I_A-29
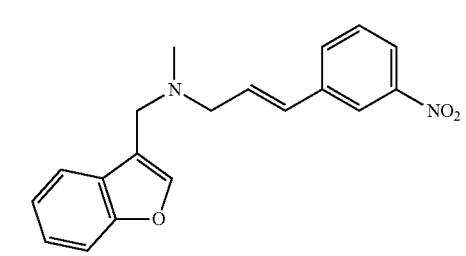
I_A-30
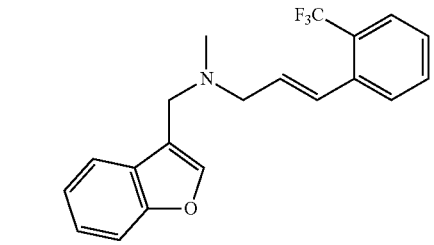

I<sub>A</sub>-31
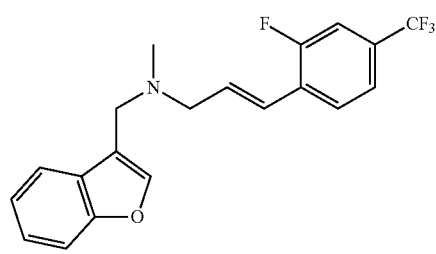
I<sub>A</sub>-32
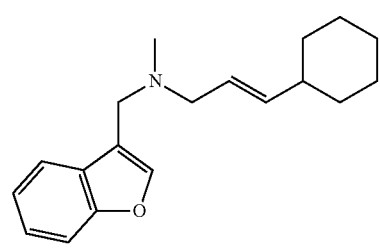
I<sub>A</sub>-33
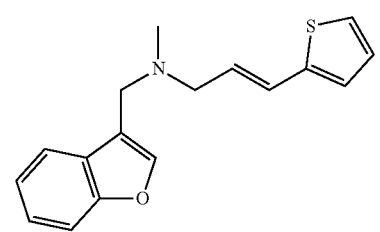
I<sub>A</sub>-34
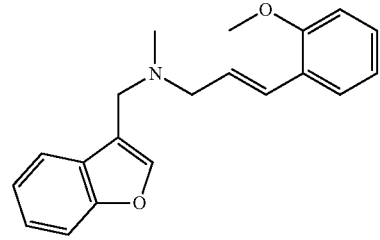
I<sub>A</sub>-35
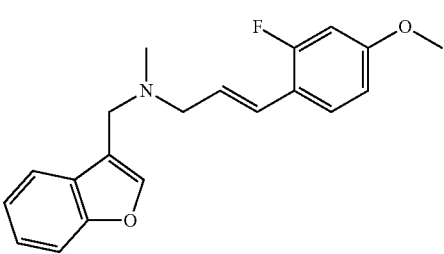
I<sub>A</sub>-36
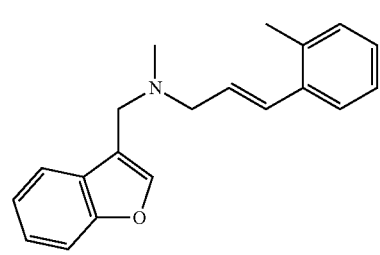
I<sub>A</sub>-37
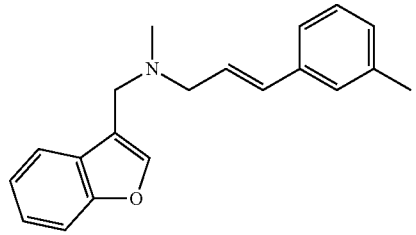
I<sub>A</sub>-38
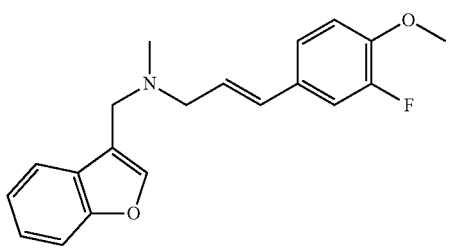
I<sub>A</sub>-39
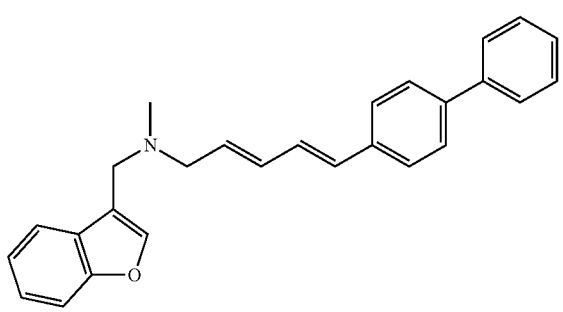
I<sub>A</sub>-40
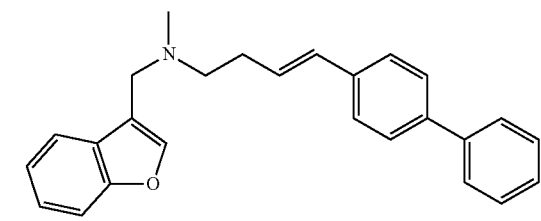
I<sub>A</sub>-41
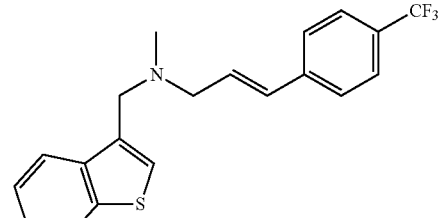
I<sub>B</sub>-1
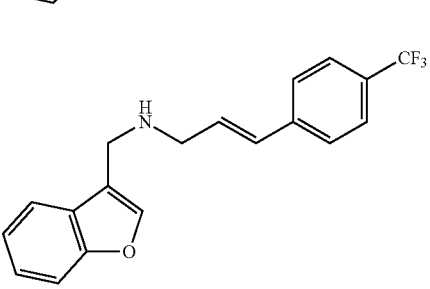

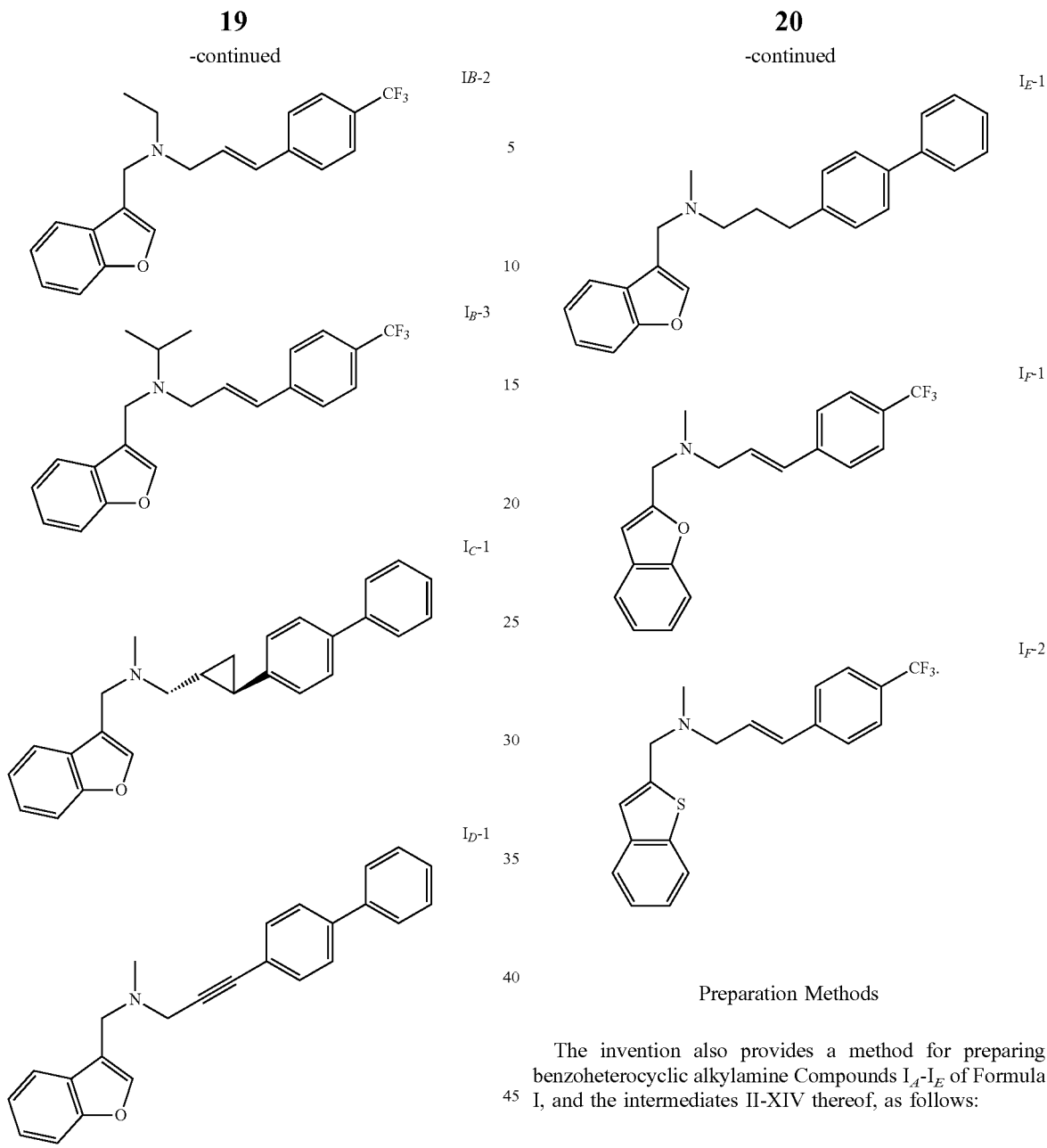
Preparation Methods
The invention also provides a method for preparing benzoheterocyclic alkylamine Compounds $I_A$-$I_E$ of Formula I, and the intermediates II-XIV thereof, as follows:
Synthesis of $I_A$
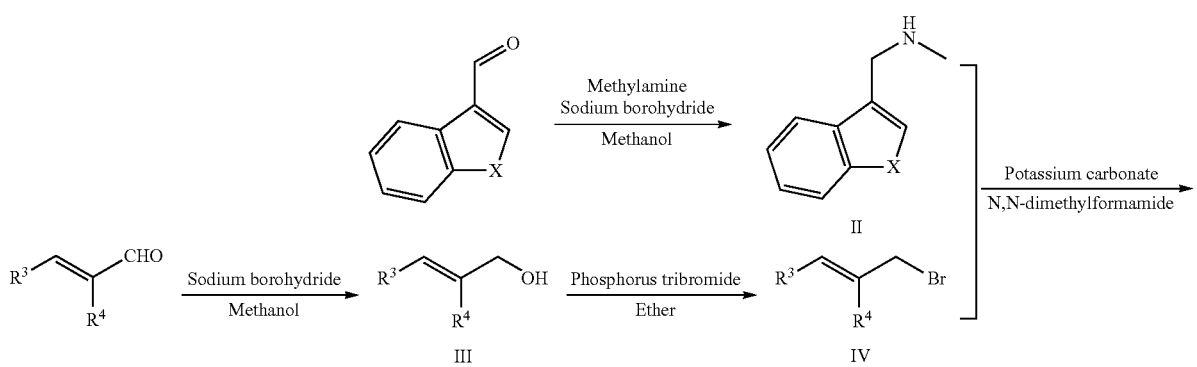

-continued

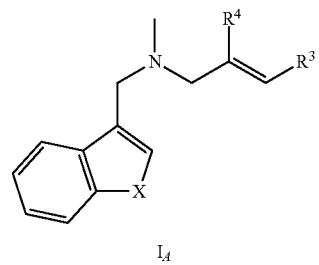

I$_A$

In the formulas X is O or S, and R$^3$ has the same meaning as described above, and R$^4$ is selected from a C$_0$-C$_3$ linear alkyl.

1) Benzofuran-3-carboxaldehyde/benzothiophene-3-carboxaldehyde is dissolved in methanol, and an alcohol solution of methylamine is added thereto; the mixture is stirred at room temperature for 4 h and added with sodium borohydride; the mixture is added with water for quenching the reaction, extracted with ethyl acetate for 3 times, washed with a saturated saline (benzofuran/thiophen-3-yl)methylamine (Intermediate II).

2) (E)-2-R-3-R-propenal is dissolved in methanol, and sodium borohydride is added in batches under ice bath; the mixture reacts at room temperature for 10-30 min followed by concentration; the residue is added with water, extracted with ethyl acetate for 3 times, washed with a saturated saline solution, dried over anhydrous magnesium sulfate, followed by filtration and concentration to obtain an intermediate (E)-2-R$^4$-3-R$^3$-propenol (Intermediate III).

3) Intermediate III is dissolved in anhydrous diethyl ether, phosphorus tribromide is added under nitrogen protection and ice bath, and the mixture reacts at 20-30° C. for 10-20 h; after completion of the reaction, the reaction system is poured into an ice-cold saturated solution of sodium hydrogen carbonate, extracted with ethyl acetate for 3 times, washed with a saturated saline solution, dried over anhydrous magnesium sulfate, then filtered, and concentrated at 30° C. to obtain an intermediate (E)-2-R$^4$-3-R$^3$-propylene bromide (Intermediate IV).

4) Intermediate II, intermediate IV, and potassium carbonate are added to N,N-dimethylformamide, and the mixture reacts at 20-30° C. for 10-20 h; after completion of the reaction, the reaction system is added with water, extracted with ethyl acetate for 3 times, washed with a saturated saline solution, dried over anhydrous sodium sulfate, followed by filtration and concentration; and the residue is purified by column chromatography to obtain a compound (E)-N-methyl-N-[(benzofuran-7-yl)methylene]-2-R$^4$-3-R$^3$-prop-2-en-1-amine (I$_A$).

Synthesis of I$_B$

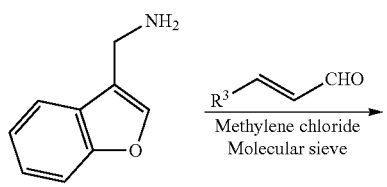

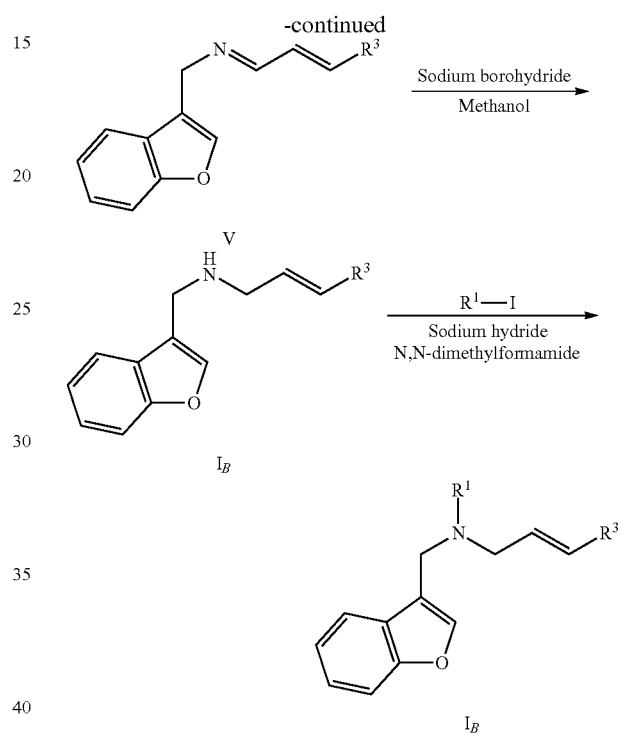

In the formulas, the meanings of R$^1$ and R$^3$ are the same as described above.

1) Benzofuran-3-methylamine, E-3-R$^3$-propenal, and molecular sieve are added to dichloromethane, and the mixture is heated under reflux to react for 15-30 h; after completion of the reaction, and the mixture is cooled to room temperature followed by filtration and concentration; and the residue is purified by column chromatography to obtain an intermediate (E,E)-N-(3-R$^3$-prop-2-en-1-ylidene)-N-(benzofuran-3-yl)methylamine (Intermediate V).

2) Intermediate V is dissolved in methanol, and sodium borohydride is added in batches under ice bath; the mixture reacts at room temperature for 10-30 min followed by concentration; the residue is added with water, extracted with ethyl acetate for 3 times, washed with a saturated saline solution, and dried over anhydrous sodium sulfate followed by filtration and concentration to obtain an intermediate (E)-N-[(benzofuran-3-yl)methylene]-3-R$^3$-prop-2-en-1-amine (one type of targets I$_B$).

3) The target I$_B$ is dissolved in anhydrous N,N-dimethylformamide, sodium hydride is added in batches under ice bath, and the mixture reacts with stirring for 10-30 min; R$^1$ is added to replace iodine, and the reaction is carried out at 20-30° C. for 10-20 h under nitrogen protection; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain a compound (E)-N—$R^1$—N-[(benzofuran-7-yl)methylene]-3-$R^3$-prop-2-en-1-amine (another type of targets $I_B$).

Synthesis of $I_C$

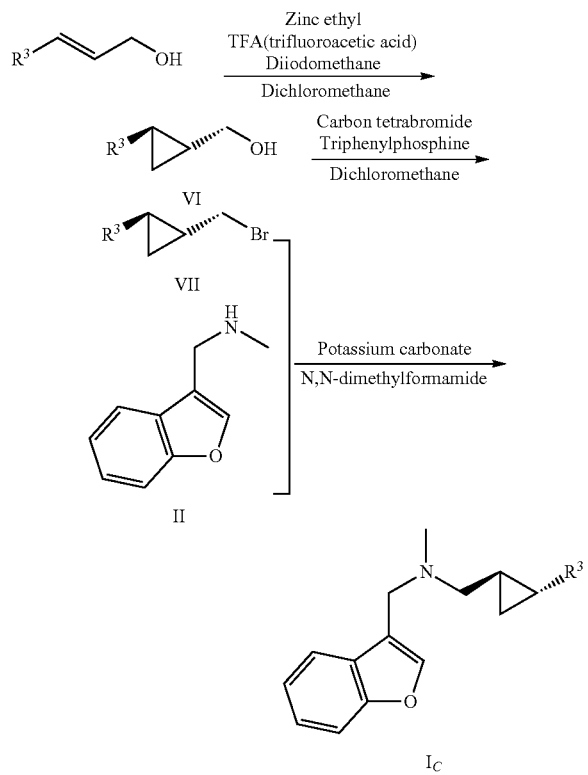

C. for 10-20 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain N-(benzooxo-alicyclic-methyl)-N-methyl-(1S,2S)-2-$R^3$-1-cyclopropyl-methylamine ($I_C$).

Synthesis of $I_D$

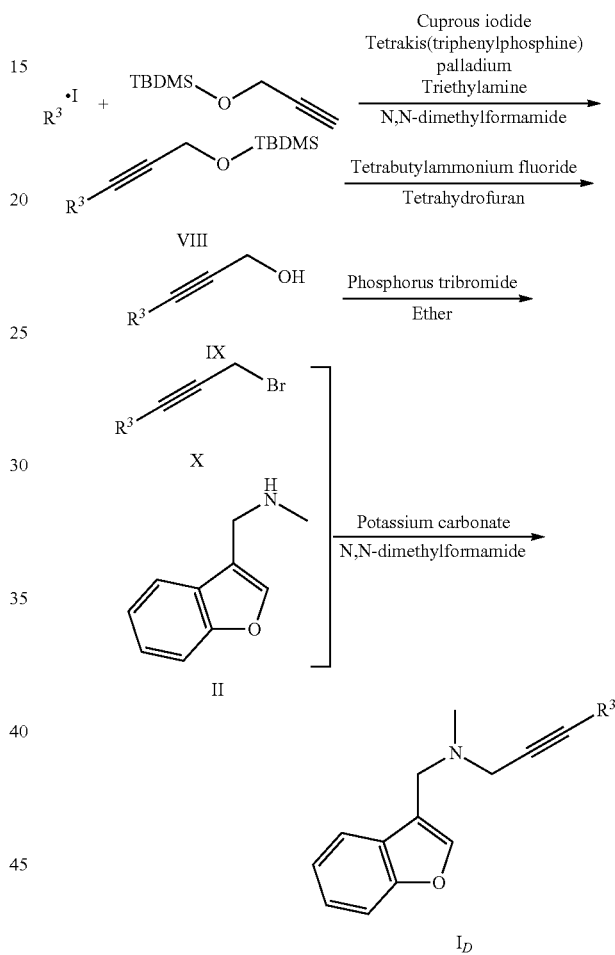

In the formulas, the meaning of $R^3$ is the same as described above.

1) Ethyl zinc is dissolved in dichloromethane, trifluoroacetic acid and diiodomethane are added slowly under nitrogen protection, and the mixture reacts at 5° C. for 30 min; $R^3$ cinnamyl alcohol is dissolved in dichloromethane, and then the mixture was slowly added dropwise into the above solution for 3 h reaction; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain (1S,2S)-2-$R^3$-1-hydroxymethylcyclopropane (VI).

2) Carbon tetrabromide is dissolved in dichloromethane, triphenylphosphine is added in batches under stirring; then Intermediate VI is added after stirring for 15 min, the mixture reacts for 1-3 h followed by filtration and concentration; and the residue is purified by column chromatography to obtain (1S,2S)-2-$R^3$-1-bromomethylcyclopropane (Intermediate VII).

3) Intermediate VII, N-methylbenzooxo-alicyclic methylamine intermediate, and potassium carbonate are added to N,N-dimethylformamide, and the mixture reacts at 20-30°

In the formulas, the meaning of $R^3$ is the same as described above.

1) Iodine substituted $R^3$ intermediate and TBDMS-protected propargyl alcohol are dissolved in N,N-dimethylformamide, cuprous iodide, tetrakis(triphenylphosphine) palladium and triethylamine are added respectively, and the mixture reacts at 80° C. for 4-6 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain O-TBDMS-3-$R^3$-propanol-2-yne (Intermediate VIII).

2) Intermediate VIII is dissolved in tetrahydrofuran, the mixture was cooled to less than 5° C. and stirred under nitrogen protection, tetrabutylammonium fluoride is added, and the reaction is carried out for 1-3 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain 3-R³-propanol-2-yne (Intermediate IX).

3) Intermediate IX is dissolved in anhydrous diethyl ether, phosphorus tribromide is added thereto under nitrogen protection and ice bath, and the mixture reacts at 20-30° C. for 15 min; after completion of the reaction, the reaction system was poured into a ice-cold saturated solution of sodium bicarbonate, extracted with ethyl acetate for 3 times, washed with a saturated saline solution, dried over anhydrous magnesium sulfate, then filtered, and concentrated at 30° C. to obtain an intermediate 3-R³-1-propylbromo-2-yne (Intermediate X).

4) Intermediate X, N-methylbenzooxo-alicyclic methylamine intermediate, and potassium carbonate are added to N,N-dimethylformamide, and the mixture reacts at 20-30° C. for 10-20 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain (E)-N-(benzooxo-alicyclic-methyl)-N-methyl-2-methyl-3-R³-2-1-propynylamine ($I_D$).

Synthesis of $I_E$

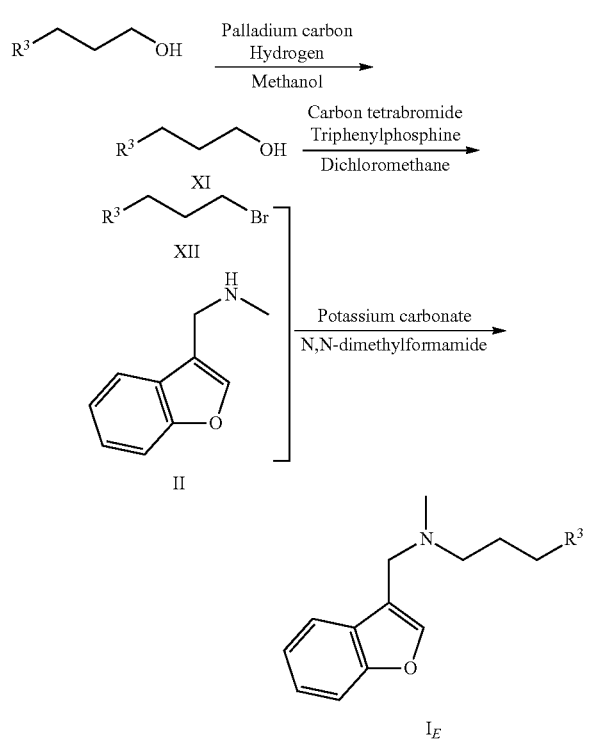

In the formulas, the meaning of R³ is the same as described above.

(1) R³ cinnamyl alcohol is dissolved in methanol, a catalytic amount of palladium carbon is added, air is replaced and hydrogen gas is introduced, and the mixture reacts at 20-30° C. for 8-10 h followed by filtration and concentration; and the residue is purified by column chromatography to obtain 3-R³-propanol (Intermediate XI);

(2) Carbon tetrabromide was dissolved in dichloromethane, triphenylphosphine was added in batches under stirring, Intermediate XI is added after stirring for 15 min, and the mixture reacts for 1-3 h followed by filtration and concentration; and the residue is purified by column chromatography to obtain 3-R³-1-bromopropane (Intermediate XII).

(3) Intermediate XII, N-methylbenzooxo-alicyclic methylamine intermediate, and potassium carbonate are added to N,N-dimethylformamide, and the mixture reacts at 20-30° C. for 10-20 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain N-(benzooxo-alicyclic-methyl)-N-methyl-3-R¹-propylamine XI(I).

Synthesis of $I_F$

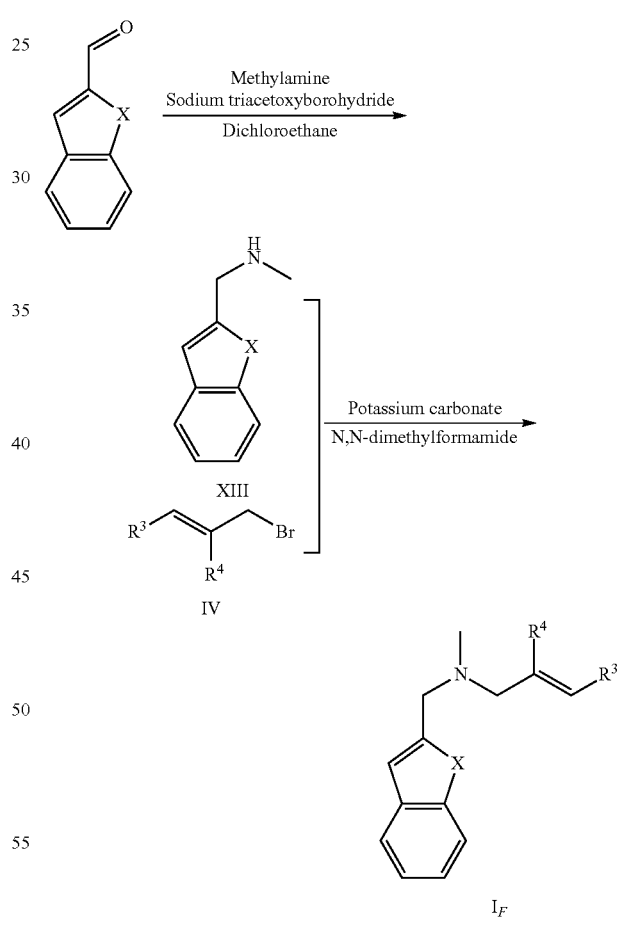

1) Benzofuran-2-carboxaldehyde/benzothiophene-2-carboxaldehyde is dissolved in dichloroethane, an alcohol solution of methylamine is added thereto, the mixture is stirred at room temperature for 4 h, and then sodium borohydride triacetate was added; the reaction system was added with water for quenching the reaction, extracted with ethyl acetate for 3 times, washed with a saturated saline solution, and dried over anhydrous magnesium sulfate followed by filtration and concentration; and the residue is purified by column chromatography to obtain an intermediate N-methyl (benzofuran/thiophen-2-yl)methylamine (Intermediate XIII).

2) Intermediate IV, Intermediate X, and potassium carbonate are added to N,N-dimethylformamide, and the mixture reacts at 20-30° C. for 10-20 h; after completion of the reaction, the reaction system is added with water, extracted with ethyl acetate for 3 times, washed with a saturated saline solution, and dried over anhydrous sodium sulfate followed by filtration and concentration; and the residue is purified by column chromatography to obtain a compound (E)-N-methyl-N-[(benzofuran-2-yl)methylene]-2-$R^4$-3-$R^3$-prop-2-en-1-amine ($I_A$).

All of the compounds encompassed by Formulas $I_A$-$I_F$ can be obtained by one of ordinary skill in the art in light of the teachings of the above-described preparation methods, without any creative labor.

The invention will be further illustrated in the following examples. These examples are for illustrative purposes only, and are not intended to limit the scope of the invention in any way. All parameters in the examples, as well as the rest of the description, are in mass (grams) unless otherwise stated.

Example 1

Preparation of 1-(benzofuran-3-yl)-N-methylmethylamine (Intermediate II)

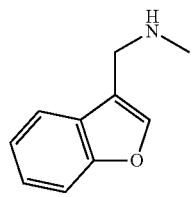

II 18.2 g of benzofuran-3-carboxaldehyde was dissolved in 20 mL of methanol solution, 31 g of alcohol solution of methylamine (mass fraction: 33%) was added dropwise to the reaction system, and the mixture reacted at room temperature for 4 h; 7.5 g of NaBH$_4$ was added in batches at 0° C., and the mixture reacted for 10 min; after completion of the reaction, the reaction system was added with 8 mL of water for quenching the reaction, followed by extraction with ethyl acetate, drying, filtration and concentration to obtain 7.8 g of the yellow oily title compound with a yield of 95%.

$^1$H-NMR (400 MHz, CDCl3) δ7.63 (dt, J=15.3, 4.5 Hz, 1H), 7.58 (s, 1H), 7.34-7.27 (m, 1H), 7.26-7.24 (m, 1H), 3.90 (d, J=0.9 Hz, 2H), 2.51 (d, J=4.2 Hz, 3H).

Example 2

Preparation of (E)-3-phenyl-propenol (Intermediate III-1)

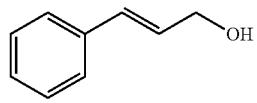

III-1

100 mg of (E)-3-phenyl-propenal was dissolved in 10 mL of methanol, 26 mg of sodium borohydride was added in batches under ice bath, and the mixture reacted at room temperature for 15 min; the reaction system was concentrated, and the residue was added with water, extracted with ethyl acetate for 3 times, washed with a saturated saline solution, and dried over anhydrous magnesium sulfate, followed by filtration and concentration to obtain 99 mg oily title compound with a yield of 98%, which was used for the following reaction directly.

Example 3

Preparation of (E)-1-phenyl-3-bromo-propene (Intermediate IV-1)

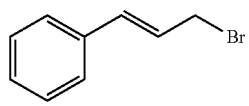

IV-1

370 mg of Intermediate III-1 was dissolved in 20 mL of anhydrous diethyl ether, 85 μl of phosphorus tribromide was added under nitrogen protection and ice bath, and the reaction was carried out at room temperature overnight; after completion of the reaction, the reaction system was poured into an ice-cold saturated solution of sodium bicarbonate, extracted with ethyl acetate for 3 times, washed with a saturated saline solution, and dried over anhydrous magnesium sulfate, followed by filtration and concentration at 30° C. to obtain 395 mg of title compound as a white solid with a yield of 85%. $^1$H-NMR (400 MHz, CDCl3) δ7.24 (t, J=7.4 Hz, 2H), 7.13 (d, J=7.4 Hz, 2H), 7.33 (d, 1H), 6.61 (d, J=15.6 Hz, 1H), 6.34 (dt, J=15.6, 7.8 Hz, 1H), 3.97 (d, J=7.7 Hz, 2H).

Example 4

Preparation of (E)-N-methyl-N-[(benzofuran-3-yl)methylene]-3-phenylprop-2-en-1-amine (Compound $I_A$-1)

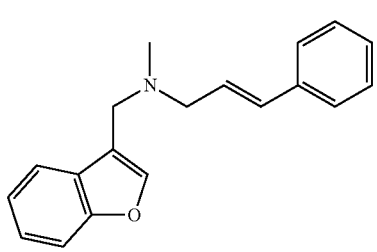

$I_A$-1

120 mg of Intermediate II, 148 mg of Intermediate IV-1, and 116 mg of potassium carbonate were added to 10 mL of N,N-dimethylformamide, and the mixture reacted at room temperature overnight; after completion of the reaction, the reaction system was added with water, extracted with ethyl acetate for 3 times, washed with a saturated saline solution, dried over anhydrous sodium sulfate, followed by filtration and concentration, and the residue was purified with column chromatography to obtain 145 mg of title compound as colorless oil with a yield of 67%; the compound was purified by dissolving it in 1 mL of ethyl acetate, introducing hydrogen chloride gas for 1 min to prepare the hydrochloride thereof, evaporating the solvent to dryness, adding a 1/100 petroleum ether/ethyl acetate mixed solvent, precipitating white hydrochloride solid, followed by suction filtration and washing to obtain Compound $I_A$-1 hydrochloride. $^1$H-NMR data is obtained from the hydrochloride form.

$^1$H-NMR (400 MHz, MeOD) δ 8.12 (s, 1H), 7.80 (m, 1H), 7.60 (m, 1H), 7.48 (d, J=23.1 Hz, 2H), 7.39 (m, 5H), 6.95 (d, J=16.0 Hz, 1H), 6.40 (m, 1H), 4.68 (d, J=13.7 Hz, 1H), 4.52 (d, J=13.5 Hz, 1H), 4.12 (s, 1H), 3.95 (s, 1H), 2.88 (d, J=17.6 Hz, 3H); HRMS (ESI) m/z calcd for $C_{19}H_{20}NO$ (M+H)$^+$ 278.1545, found 278.1545.

Example 5

Preparation of (E)-N-methyl-N-[(benzofuran-3-yl)methylene]-3-(4-trifluoromethylphenyl)-prop-2-en-1-amine (Compound $I_A$-2)

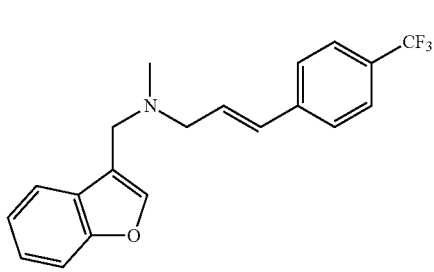

In addition to replacement of (E)-3-phenyl-propenal with (E)-3-(4-trifluoromethylphenyl)-propenal, the remaining starting materials, reagents and preparation methods as required were the same as in Examples 2-4, and 122 mg oily title compound was obtained with a yield of 49%. The hydrochloride of this compound was a white solid.

$^1$H-NMR (400 MHz, MeOD) δ 8.13 (s, 1H), 7.82 (d, J=8.1 Hz, 1H), 7.73-7.64 (m, 5H), 7.60 (d, J=7.8 Hz, 1H), 7.41 (dtd, J=17.8, 7.3, 1.2 Hz, 2H), 7.01 (d, J=15.9 Hz, 1H), 6.59-6.47 (m, 1H), 4.61 (d, J=37.0 Hz, 2H), 4.24-4.07 (m, 1H), 4.00 (s, 1H), 2.92 (s, 3H). HRMS (ESI) m/z calcd for $C_{20}H_{19}F_3NO$ (M+H)$^+$ 346.1419, found 346.1418.

Example 6

Preparation of (E)-N-methyl-N-[(benzofuran-3-yl)methylene]-3-(4-chlorophenyl)prop-2-en-1-amine (Compound $I_A$-3)

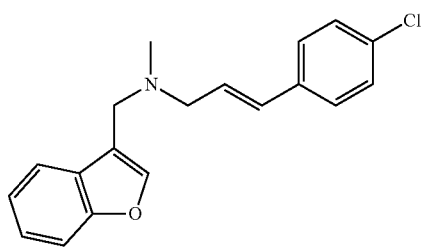

In addition to replacement of (E)-3-phenyl-propenal with (E)-3-(4-chlorophenyl)-propenal, the remaining starting materials, reagents and preparation methods as required were the same as in Examples 2-4, and 116 mg oily title compound was obtained with a yield of 49%. The hydrochloride salt of this compound was a white solid.

$^1$H-NMR (400 MHz, MeOD) δ 8.12 (s, 1H), 7.80 (d, J=7.4 Hz, 1H), 7.60 (d, J=8.0 Hz, 1H), 7.50 (d, J=8.5 Hz, 2H), 7.46-7.34 (m, 4H), 6.92 (d, J=16.3 Hz, 1H), 6.39 (dd, J=15.2, 7.9 Hz, 1H), 4.59 (d, J=36.9 Hz, 2H), 4.02 (d, J=52.6 Hz, 2H), 2.90 (s, 3H); HRMS (ESI) m/z calcd for $C_{19}H_{19}ClNO$ (M+H)$^+$ 312.1155, found 312.1154.

Example 7

Preparation of (E)-N-methyl-N-[(benzofuran-3-yl)methylene]-3-(4-fluorophenyl)prop-2-en-1-amine (Compound $I_A$-4)

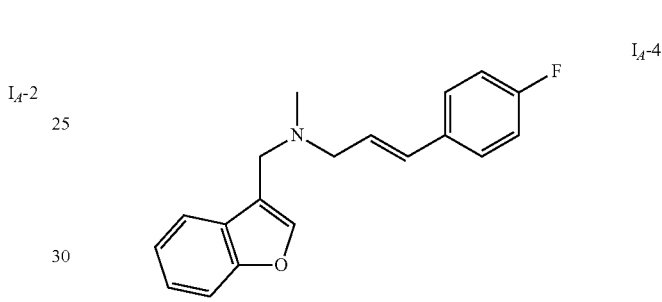

In addition to replacement of (E)-3-phenyl-propenal with (E)-3-(4-fluorophenyl)-propenal, the remaining starting materials, reagents and preparation methods as required were the same as in Examples 2-4, and 110 mg oily title compound was obtained with a yield of 51%. The hydrochloride salt of this compound was a white solid.

$^1$H-NMR (400 MHz, MeOD) δ 8.11 (s, 1H), 7.80 (d, J=7.7 Hz, 1H), 7.64-7.51 (m, 3H), 7.40 (ddd, J=15.1, 13.9, 6.8 Hz, 2H), 7.12 (t, J=8.7 Hz, 2H), 6.92 (d, J=15.8 Hz, 1H), 6.41-6.24 (m, 1H), 4.54 (s, 2H), 4.02 (d, J=51.4 Hz, 2H), 2.90 (s, 3H). HRMS (ESI) m/z calcd for $C_{19}H_{19}FNO$ (M+H)$^+$ 296.1451, found 296.1450.

Example 8

Preparation of (E)-N-methyl-N-[(benzofuran-3-yl)methylene]-3-(4-bromophenyl)prop-2-en-1-amine (Compound $I_A$-5)

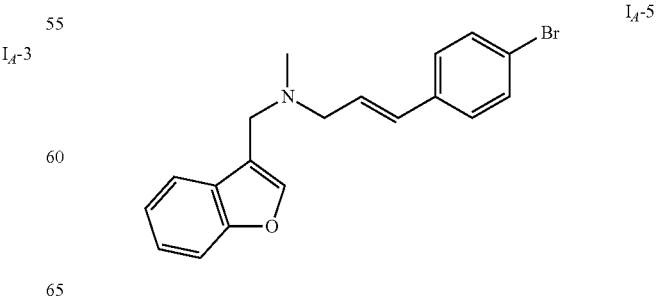

In addition to replacement of (E)-3-phenyl-propenal with (E)-3-(4-bromophenyl)-propenal, the remaining starting materials, reagents and preparation methods as required were the same as in Examples 2-4, and 115 mg oily title compound was obtained with a yield of 53%. The hydrochloride salt of this compound was a white solid.

¹H-NMR (400 MHz, MeOD) δ 8.12 (s, 1H), 7.81 (d, J=7.4 Hz, 1H), 7.60 (d, J=8.1 Hz, 1H), 7.54 (d, J=8.4 Hz, 2H), 7.47-7.35 (m, 4H), 6.90 (d, J=15.8 Hz, 1H), 6.51-6.31 (m, 1H), 4.58 (s, 2H), 4.01 (s, 2H), 2.89 (s, 3H); HRMS (ESI) m/z calcd for $C_{19}H_{19}BrNO$ (M+H)⁺ 356.0650, found 358.0636.

Example 9

Preparation of (E)-N-methyl-N-[(benzofuran-3-yl)methylene]-3-(4-difluoromethylphenyl)-prop-2-en-1-amine (Compound $I_A$-6)

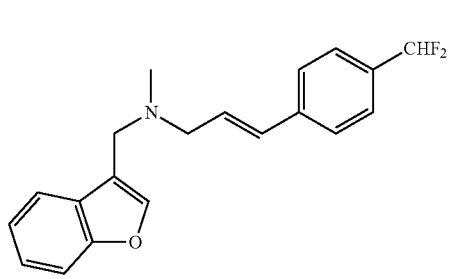

$I_A$-6

In addition to replacement of (E)-3-phenyl-propenal with (E)-3-(4-difluoromethylphenyl)-propenal, the remaining starting materials, reagents and preparation methods as required were the same as in Examples 2-4, and 111 mg oily title compound was obtained with a yield of 47%. The hydrochloride salt of this compound was a white solid.

¹H-NMR (400 MHz, MeOD) δ 8.11 (s, 1H), 7.81 (d, J=7.5 Hz, 1H), 7.67-7.53 (m, 5H), 7.47-7.35 (m, 2H), 6.98 (d, J=16.1 Hz, 1H), 6.84 (d, J=56.0 Hz, 1H), 6.47 (dt, J=15.1, 7.5 Hz, 1H), 4.55 (s, 2H), 3.99 (s, 2H), 2.91 (s, 3H); HRMS (ESI) m/z calcd for $C_{20}H_{20}F_2NO$ (M+H)⁺ 328.1513, found 328.1512.

Example 10

Preparation of (E)-N-methyl-N-[(benzofuran-3-yl)methylene]-3-(4-cyclopentyl)prop-2-en-1-amine (Compound $I_A$-7)

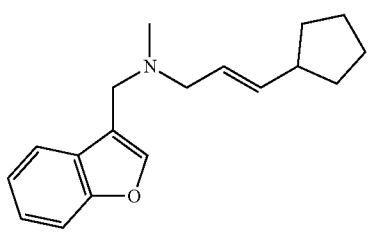

$I_A$-7

In addition to replacement of (E)-3-phenyl-propenal with (E)-3-(4-cyclopentyl)-propenal, the remaining starting materials, reagents and preparation methods as required were the same as in Examples 2-4, and 85 mg oily title compound was obtained with a yield of 43%. The hydrochloride salt of this compound was a white solid.

¹H-NMR (400 MHz, MeOD) δ 8.08 (s, 1H), 7.78 (d, J=7.3 Hz, 1H), 7.60 (d, J=7.9 Hz, 1H), 7.47-7.34 (m, 2H), 6.07 (dd, J=15.4, 7.7 Hz, 1H), 5.62 (dt, J=14.8, 7.3 Hz, 1H), 4.59 (d, J=14.0 Hz, 1H), 4.42 (d, J=13.9 Hz, 1H), 3.99-3.84 (m, 1H), 3.77-3.62 (m, 1H), 2.82 (s, 3H), 2.59 (dd, J=15.9, 8.3 Hz, 1H), 1.85 (s, 2H), 1.77-1.58 (m, 4H), 1.39 (s, 2H); HRMS (ESI) m/z calcd for $C_{18}H_{24}NO$ (M+H)⁺ 270.1858, found 270.1857.

Example 11

Preparation of (E)-N-methyl-N-[(benzofuran-3-yl)methylene]-3-(2-chlorophenyl)prop-2-en-1-amine (Compound $I_A$-8)

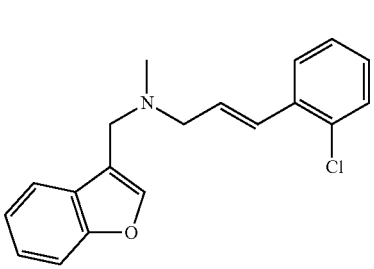

$I_A$-8

In addition to replacement of (E)-3-phenyl-propenal with (E)-3-(2-chlorophenyl)-propenal, the remaining starting materials, reagents and preparation methods as required were the same as in Examples 2-4, and 110 mg oily title compound was obtained with a yield of a 47%. The hydrochloride salt of this compound was a white solid.

¹H-NMR (400 MHz, MeOD) δ 8.11 (s, 1H), 7.82 (d, J=7.2 Hz, 1H), 7.74-7.69 (m, 1H), 7.60 (d, J=8.0 Hz, 1H), 7.42 (dd, J=17.3, 7.5 Hz, 3H), 7.37-7.29 (m, 3H), 6.40 (dt, J=15.4, 7.6 Hz, 1H), 4.58 (s, 2H), 4.04 (s, 2H), 2.91 (s, 3H); HRMS (ESI) m/z calcd for $C_{19}H_{19}ClNO$ (M+H)⁺ 312.1155, found 312.1156.

Example 12

Preparation of (E)-N-methyl-N-[(benzofuran-3-yl)methylene]-3-(3-fluoro-4-trifluoromethyl-phenyl)prop-2-ene-1-the amine (Compound $I_A$-9)

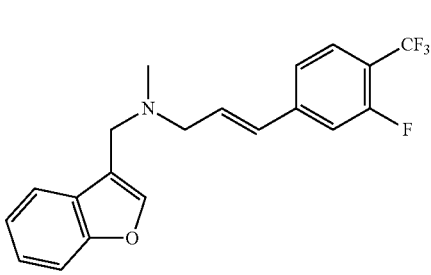

$I_A$-9

In addition to replacement of (E)-3-phenyl-propenal with (E)-3-(3-fluoro-4-trifluoromethylphenyl)-propenal, the remaining starting materials, reagents and preparation methods as required were the same as in Examples 2-4, and 121 mg oily title compound was obtained with a yield of 53%. The hydrochloride salt of this compound was a white solid.

$^1$H-NMR (400 MHz, MeOD) δ 8.07 (s, 1H), 7.80 (d, J=7.1 Hz, 1H), 7.69 (t, J=7.6 Hz, 1H), 7.58 (d, J=8.0 Hz, 1H), 7.54-7.34 (m, 4H), 6.92 (d, J=16.4 Hz, 1H), 6.63-6.50 (m, 1H), 4.63 (s, 2H), 4.49 (s, 1H), 3.96 (s, 1H), 3.48 (s, 1H), 2.83 (s, 3H); HRMS (ESI) m/z calcd for $C_{20}H_{18}F_4NO$ (M+H)$^+$ 364.1325, found 364.1326.

Example 13

Preparation of (E)-N-methyl-N-[(benzofuran-3-yl)methylene]-3-(naphthalen-1-yl)prop-2-en-1-amine (Compound $I_A$-10)

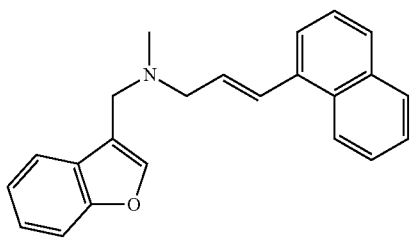

I$_A$-10

In addition to replacement of (E)-3-phenyl-propenal with (E)-3-(naphthalen-1-yl)-propenal, the remaining starting materials, reagents and preparation methods as required were the same as in Examples 2-4, and 144 mg oily title compound was obtained with a yield of 59%. The hydrochloride salt of this compound was a white solid.

$^1$H-NMR (400 MHz, MeOD) δ 8.16 (d, J=8.7 Hz, 2H), 7.94-7.87 (m, 2H), 7.86-7.73 (m, 3H), 7.61 (d, J=7.8 Hz, 1H), 7.59-7.34 (m, 5H), 6.49-6.34 (m, 1H), 4.67 (d, J=36.8 Hz, 2H), 4.18 (d, J=49.8 Hz, 2H), 2.97 (s, 3H); HRMS (ESI) m/z calcd for $C_{23}H_{22}NO$ (M+H)$^+$ 328.1701, found 328.1700.

Example 14

Preparation of (E)-N-methyl-N-[(benzofuran-3-yl)methylene]-3-(2,4-dichlorophenyl)prop-2-en-1-amine (Compound $I_A$-11)

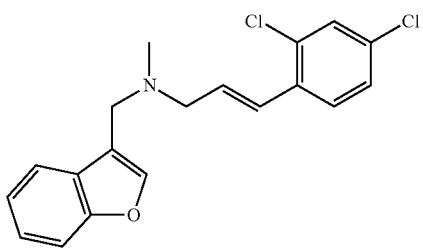

I$_A$-11

In addition to replacement of (E)-3-phenyl-propenal with (E)-3-(2,4-dichlorophenyl)-propenal, the remaining starting materials, reagents and preparation methods as required were the same as in Examples 2-4, and 143 mg oily title compound was obtained with a yield of 59%. The hydrochloride salt of this compound was a white solid.

$^1$H-NMR (400 MHz, MeOD) δ 8.13 (s, 1H), 7.82 (d, J=7.5 Hz, 1H), 7.71 (d, J=8.5 Hz, 1H), 7.60 (d, J=7.7 Hz, 1H), 7.53 (d, J=2.0 Hz, 1H), 7.40 (ddt, J=9.9, 8.5, 4.1 Hz, 3H), 7.27 (d, J=15.7 Hz, 1H), 6.43 (dt, J=15.6, 7.7 Hz, 1H), 4.69 (d, J=13.9 Hz, 1H), 4.55 (d, J=13.8 Hz, 1H), 4.19 (dd, J=13.3, 6.8 Hz, 1H), 4.02 (dd, J=13.5, 7.8 Hz, 1H), 2.92 (s, 3H); HRMS (ESI) m/z calcd for $C_{19}H_{18}C_2NO$ (M+H)$^+$ 346.0765, found 346.0763.

Example 15

Preparation of (E)-N-methyl-N-[(benzofuran-3-yl)methylene]-3-(3-chlorophenyl)prop-2-en-1-amine (Compound $I_A$-12)

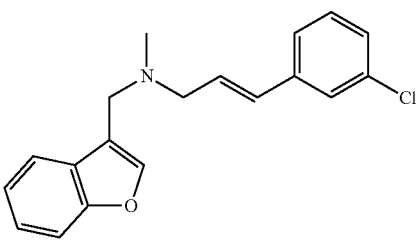

I$_A$-12

In addition to replacement of (E)-3-phenyl-propenal with (E)-3-(3-chlorophenyl)-propenal, the remaining starting materials, reagents and preparation methods as required were the same as in Examples 2-4, and 170 mg oily title compound was obtained with a yield of 70%. The hydrochloride salt of this compound was a white solid.

$^1$H-NMR (400 MHz, MeOD) δ 8.14 (s, 1H), 7.83 (d, J=7.0 Hz, 1H), 7.63-7.54 (m, 2H), 7.43 (t, J=8.1 Hz, 2H), 7.40-7.32 (m, 3H), 6.91 (d, J=15.8 Hz, 1H), 6.52-6.36 (m, 1H), 4.61 (d, J=36.8 Hz, 2H), 4.04 (d, J=55.0 Hz, 2H), 2.90 (s, 3H); HRMS (ESI) m/z calcd for $C_{19}H_{19}ClNO$ (M+H)$^+$ 312.1155, found 312.1154.

Example 16

Preparation of (E)-N-methyl-N-[(benzofuran-3-yl)methylene]-3-(4-methylcarboxylate phenyl)prop-2-en-1-amine (Compound $I_A$-13)

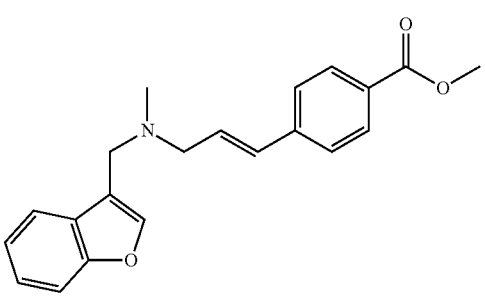

I$_A$-13

In addition to replacement of (E)-3-phenyl-propenal with (E)-3-(4-methylcarboxylate phenyl)-propenal, the remaining starting materials, reagents and preparation methods as required were the same as in Examples 2-4, and 212 mg oily title compound was obtained with a yield of 85%. The hydrochloride salt of this compound was a white solid.

$^1$H-NMR (400 MHz, MeOD) δ 8.13 (s, 1H), 8.02 (d, J=8.4 Hz, 2H), 7.82 (d, J=7.5 Hz, 1H), 7.62 (t, J=8.8 Hz, 3H), 7.48-7.30 (m, 2H), 7.00 (d, J=15.8 Hz, 1H), 6.60-6.43 (m, 1H), 4.69 (d, J=13.9 Hz, 1H), 4.54 (d, J=13.7 Hz, 1H), 4.15 (d, J=7.1 Hz, 1H), 4.04-3.94 (m, 1H), 3.91 (s, 3H), 2.92 (s, 3H); HRMS (ESI) m/z calcd for $C_{21}H_{22}NO_3$ (M+H)$^+$ 336.1600, found 336.1599.

Example 17

Preparation of (E)-N-methyl-N-[(furan-3-yl)methylene]-3-(furan-2-yl)-prop-2-en-1-amine (Compound $I_A$-14)

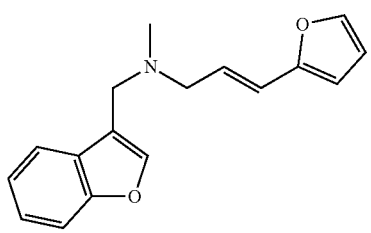

I$_A$-14

In addition to replacement of (E)-3-phenyl-propenal with (E)-3-(furan-2-yl)-propenal, the remaining starting materials, reagents and preparation methods as required were the same as in Examples 2-4, and 111 mg oily title compound was obtained with a yield of 56%. The hydrochloride salt of this compound was a white solid.

$^1$H-NMR (400 MHz, MeOD) δ 8.14 (d, J=20.9 Hz, 1H), 7.81 (d, J=7.2 Hz, 1H), 7.60 (d, J=8.0 Hz, 1H), 7.54 (s, 1H), 7.40 (ddd, J=15.0, 13.9, 6.8 Hz, 2H), 6.76 (dd, J=25.9, 15.6 Hz, 1H), 6.60-6.44 (m, 2H), 6.28-6.12 (m, 1H), 4.66 (d, J=13.9 Hz, 1H), 4.50 (d, J=13.9 Hz, 1H), 4.10 (dt, J=14.4, 7.2 Hz, 1H), 3.91 (dd, J=13.1, 8.3 Hz, 1H), 2.93-2.76 (m, 3H); HRMS (ESI) m/z calcd for $C_{17}H_{18}NO_2$ (M+H)$^+$ 268.1338, found 268.1334.

Example 18

Preparation of (E)-N-methyl-N-[(benzofuran-3-yl)methylene]-3-(4-methoxyphenyl)-prop-2-en-1-amine (Compound $I_A$-15)

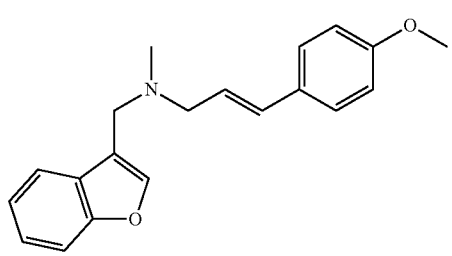

I$_A$-15

In addition to replacement of (E)-3-phenyl-propenal with (E)-3-(4-methoxyphenyl)-propenal, the remaining starting materials, reagents and preparation methods as required were the same as in Examples 2-4, and 113 mg oily title compound was obtained with a yield of 49%. The hydrochloride salt of this compound was a white solid.

$^1$H-NMR (400 MHz, MeOD) δ 8.12 (s, 1H), 7.85-7.74 (m, 1H), 7.60 (d, J=7.8 Hz, 1H), 7.46 (d, J=8.7 Hz, 2H), 7.42-7.35 (m, 2H), 6.98-6.91 (m, 2H), 6.88 (d, J=15.7 Hz, 1H), 6.22 (dt, J=15.5, 7.5 Hz, 1H), 4.66 (d, J=13.9 Hz, 1H), 4.50 (d, J=13.9 Hz, 1H), 4.10 (dd, J=12.7, 7.2 Hz, 1H), 3.91 (dd, J=13.0, 7.8 Hz, 1H), 3.81 (s, 3H), 2.89 (s, 3H); HRMS (ESI) m/z calcd for $C_{20}H_{22}NO_2$ (M+H)+308.1651, found 308.1651.

Example 19

Preparation of (E)-N-methyl-N-[(benzofuran-3-yl)methylene]-3-(4-nitrophenyl)-prop-2-en-1-amine (Compound $I_A$-16)

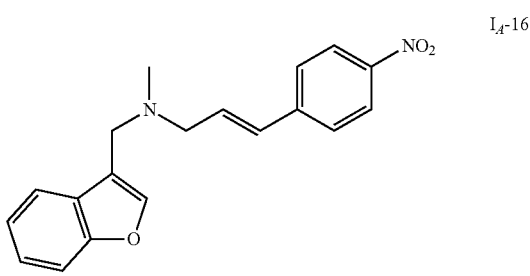 [SMILES: CN(C/C=C/c1ccc([N+](=O)[O-])cc1)Cc1coc2ccccc12]

I$_A$-16

In addition to replacement of (E)-3-phenyl-propenal with (E)-3-(4-nitrophenyl)-propenal, the remaining starting materials, reagents and preparation methods as required were the same as in Examples 2-4, and 140 mg colorless oily title compound was obtained with a yield of 58%. The hydrochloride salt of this compound was a white solid.

$^1$H-NMR (400 MHz, MeOD) δ 8.25 (d, J=8.5 Hz, 2H), 8.14 (s, 1H), 7.81 (t, J=13.0 Hz, 1H), 7.75 (d, J=8.8 Hz, 2H), 7.60 (d, J=8.1 Hz, 1H), 7.41 (dq, J=14.6, 7.2 Hz, 2H), 7.05 (d, J=15.8 Hz, 1H), 6.63 (dd, J=15.5, 7.8 Hz, 1H), 4.70 (d, J=13.6 Hz, 1H), 4.57 (d, J=14.0 Hz, 1H), 4.19 (dd, J=13.2, 6.9 Hz, 1H), 4.06-3.94 (m, 1H), 2.92 (d, J=7.7 Hz, 3H); HRMS (ESI) m/z calcd for $C_{19}H_{19}N_2O_3$ (M+H)$^+$ 323.1396, found 323.1393.

Example 20

Preparation of (E)-N-methyl-N-[(benzofuran-3-yl)methylene]-3-(4-ethoxyphenyl)-prop-2-en-1-amine (Compound $I_A$-17)

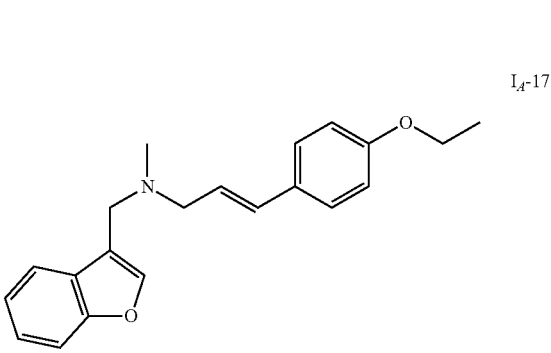 [SMILES: CCOc1ccc(/C=C/CN(C)Cc2coc3ccccc23)cc1]

I$_A$-17

In addition to replacement of (E)-3-phenyl-propenal with (E)-3-(4-ethoxyphenyl)-propenal, the remaining starting materials, reagents and preparation methods as required were the same as in Examples 2-4, and 78 mg colorless oily title compound was obtained with a yield of 39%. The hydrochloride salt of this compound was a white solid.

¹H-NMR (400 MHz, MeOD) δ 8.12 (d, J=5.9 Hz, 1H), 7.81 (d, J=6.0 Hz, 1H), 7.60 (d, J=8.1 Hz, 1H), 7.47-7.34 (m, 4H), 6.96-6.79 (m, 3H), 6.30-6.14 (m, 1H), 4.66 (d, J=14.0 Hz, 1H), 4.50 (d, J=13.8 Hz, 1H), 4.07 (ddd, J=20.8, 13.6, 7.2 Hz, 3H), 3.91 (dd, J=13.0, 8.0 Hz, 1H), 2.88 (s, 3H), 1.39 (t, J=7.0 Hz, 3H); HRMS (ESI) m/z calcd for $C_{21}H_{24}NO_2$ (M+H)⁺ 322.1807, found 322.1808.

Example 21

Preparation of (E)-N-methyl-N-[(benzofuran-3-yl)methylene]-3-(3-trifluoromethylphenyl)-prop-2-en-1-amine (Compound $I_A$-18)

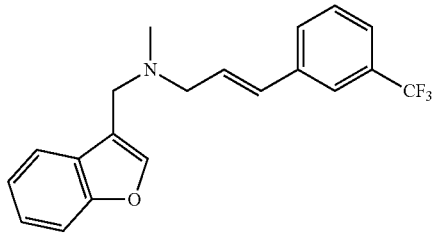

$I_A$-18

In addition to replacement of (E)-3-phenyl-propenal with (E)-3-(3-trifluoromethylphenyl)-propenal, the remaining starting materials, reagents and preparation methods as required were the same as in Examples 2-4, and 116 mg light yellow oily title compound was obtained with a yield of 58%. The hydrochloride salt of this compound was a white solid.

¹H-NMR (400 MHz, MeOD) δ 8.15 (d, J=5.1 Hz, 1H), 7.88-7.73 (m, 3H), 7.61 (dt, J=15.2, 7.7 Hz, 3H), 7.40 (dt, J=18.9, 7.3 Hz, 2H), 7.01 (d, J=15.8 Hz, 1H), 6.62-6.45 (m, 1H), 4.70 (d, J=14.0 Hz, 1H), 4.56 (d, J=13.7 Hz, 1H), 4.23-4.13 (m, 1H), 3.99 (dd, J=12.8, 7.8 Hz, 1H), 2.92 (s, 3H); HRMS (ESI) m/z calcd for $C_{20}H_{19}F_3NO$ (M+H)+ 346.1419, found 346.1418.

Example 22

Preparation of (E)-N-methyl-N-[(benzofuran-3-yl)methylene]-3-(3-fluorophenyl)-prop-2-en-1-amine (Compound $I_A$-19)

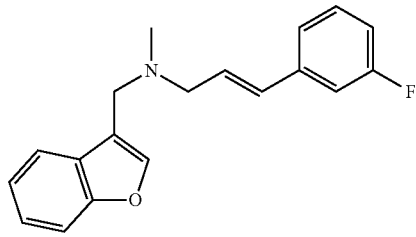

$I_A$-19

In addition to replacement of (E)-3-phenyl-propenal with (E)-3-(3-fluorophenyl)-propenal, the remaining starting materials, reagents and preparation methods as required were the same as in Examples 2-4, and 150 mg colorless oily title compound was obtained with a yield of 67%. The hydrochloride salt of this compound was a white solid.

¹H-NMR (400 MHz, MeOD) δ 8.11 (s, 1H), 7.81 (d, J=7.5 Hz, 1H), 7.64-7.58 (m, 2H), 7.45-7.34 (m, 3H), 7.24-7.11 (m, 2H), 7.08 (d, J=15.9 Hz, 1H), 6.56-6.41 (m, 1H), 4.58 (s, 2H), 4.02 (s, 2H), 2.90 (s, 3H); HRMS (ESI) m/z calcd for $C_{19}H_{19}FNO$ (M+H)⁺ 296.1451, found 296.1452.

Example 23

Preparation of (E)-N-methyl-N-[(benzofuran-3-yl)methylene]-3-(3-methoxyphenyl)-prop-2-en-1-amine (Compound $I_A$-20)

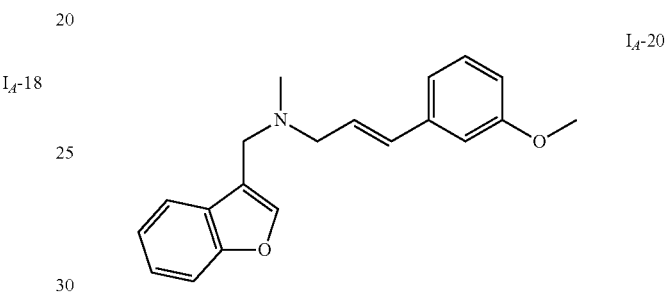

$I_A$-20

In addition to replacement of (E)-3-phenyl-propenal with (E)-3-(3-methoxyphenyl)-propenal, the remaining starting materials, reagents and preparation methods as required were the same as in Examples 2-4, and 81 mg colorless oily title compound was obtained with a yield of 50%. The hydrochloride salt of this compound was a white solid.

¹H-NMR (400 MHz, MeOD) δ 8.13 (s, 1H), 7.82 (d, J=7.3 Hz, 1H), 7.60 (d, J=8.2 Hz, 1H), 7.49-7.34 (m, 2H), 7.29 (t, J=7.9 Hz, 1H), 7.08 (dd, J=10.7, 4.8 Hz, 2H), 6.95-6.86 (m, 2H), 6.47-6.29 (m, 1H), 4.68 (d, J=14.0 Hz, 1H), 4.52 (d, J=13.7 Hz, 1H), 4.13 (dd, J=12.9, 7.2 Hz, 1H), 4.01-3.89 (m, 1H), 3.81 (s, 3H), 2.90 (s, 3H); HRMS (ESI) m/z calcd for $C_{20}H_{22}NO_2$ (M+H)⁺308.1651, found 308.1652.

Example 24

Preparation of (E)-N-methyl-N-[(benzofuran-3-yl)methylene]-3-(4-methylphenyl)-prop-2-en-1-amine (Compound $I_A$-21)

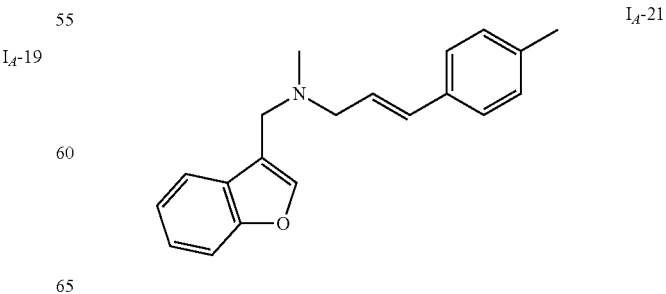

$I_A$-21

In addition to replacement of (E)-3-phenyl-propenal with (E)-3-(4-methylphenyl)-propenal, the remaining starting materials, reagents and preparation methods as required were the same as in Examples 2-4, and 110 mg colorless oily title compound was obtained with a yield of 56%. The hydrochloride salt of this compound was a white solid.

$^1$H-NMR (400 MHz, MeOD) δ 8.13 (s, 1H), 7.83 (d, J=7.2 Hz, 1H), 7.62 (dd, J=15.1, 7.8 Hz, 2H), 7.40 (qd, J=14.2, 6.8 Hz, 3H), 7.23-7.11 (m, 2H), 7.08 (d, J=16.0 Hz, 1H), 6.59-6.38 (m, 1H), 4.61 (s, 2H), 4.09 (s, 2H), 2.91 (s, 3H), 2.38 (s, 3H); HRMS (ESI) m/z calcd for $C_{20}H_{22}NO$ $(M+H)^+$ 292.1701, found 292.1702.

Example 25

Preparation of (E)-N-methyl-N-[(benzofuran-3-yl)methylene]-3-(2-nitrophenyl)-prop-2-en-1-amine (Compound $I_A$-22)

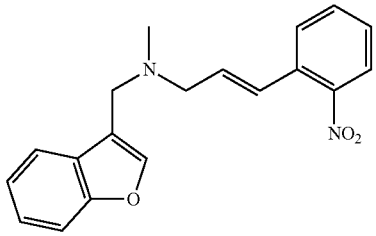

I$_A$-22

In addition to replacement of (E)-3-phenyl-propenal with (E)-3-(2-nitrophenyl)-propenal, the remaining starting materials, reagents and preparation methods as required were the same as in Examples 2-4, and 110 mg colorless oily title compound was obtained with a yield of 56%. The hydrochloride salt of this compound was a white solid.

$^1$H-NMR (400 MHz, MeOD) δ 8.14 (s, 1H), 8.07-8.02 (m, 1H), 7.85-7.80 (m, 1H), 7.76-7.71 (m, 2H), 7.63-7.56 (m, 2H), 7.46-7.34 (m, 3H), 6.38-6.27 (m, 1H), 4.70 (d, J=13.9 Hz, 1H), 4.56 (d, J=13.2 Hz, 1H), 4.17 (d, J=7.3 Hz, 1H), 4.04 (d, J=8.0 Hz, 1H), 2.95 (s, 3H); HRMS (ESI) m/z calcd for $C_{19}H_{19}N_2O_3$ $(M+H)^+$ 323.1396, found 323.1397.

Example 26

Preparation of (E)-N-methyl-N-[(benzofuran-3-yl)methylene]-but-2-en-1-amine (Compound $I_A$-23)

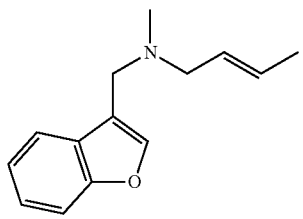

I$_A$-23

In addition to replacement of (E)-3-phenyl-propenal with 2-butenyl bromide, the remaining starting materials, reagents and preparation methods as required were the same as in Examples 2-4, and 80 mg yellow oily title compound was obtained with a yield of 49%. The hydrochloride salt of this compound was yellow and oily.

$^1$H-NMR (400 MHz, MeOD) δ 8.15 (s, 1H), 7.87-7.81 (m, 1H), 7.60 (dt, J=10.1, 4.9 Hz, 1H), 7.46-7.37 (m, 2H), 6.96-6.83 (m, 1H), 6.19-6.08 (m, 1H), 4.60 (dd, J=17.9, 9.2 Hz, 1H), 4.49-4.42 (m, 1H), 3.91 (dt, J=23.7, 11.8 Hz, 1H), 3.74 (dd, J=13.1, 7.9 Hz, 1H), 2.84 (s, 3H), 1.85 (dt, J=5.1, 2.5 Hz, 3H); HRMS(ESI) m/z calcd for $C_{14}H_{18}NO$ (M+H)+ 284.2014, found 284.2008.

Example 27

Preparation of (E)-N-Methyl-N-[(benzofuran-3-yl)methylene]-3-(4-cyanophenyl)-prop-2-en-1-amine (Compound $I_A$-24)

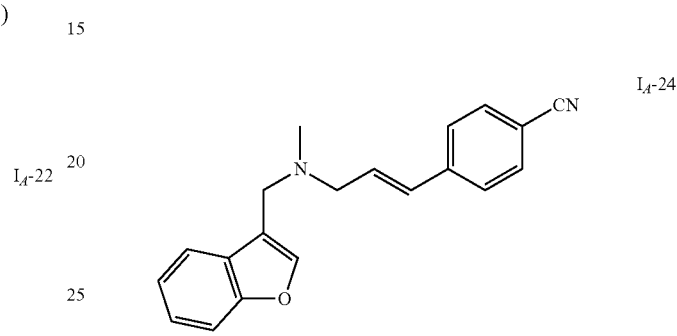

I$_A$-24

In addition to replacement of (E)-3-phenyl-propenal with (E)-3-(4-cyanophenyl)-propenal, the remaining starting materials, reagents and preparation methods as required were the same as in Examples 2-4, and 100 mg colorless oily title compound was obtained with a yield of 46%. The hydrochloride salt of this compound was a white solid.

$^1$H-NMR (400 MHz, MeOD) δ 8.13 (d, J=8.3 Hz, 1H), 7.83 (t, J=7.1 Hz, 1H), 7.74 (d, J=8.2 Hz, 3H), 7.69 (d, J=8.3 Hz, 2H), 7.60 (d, J=8.1 Hz, 1H), 7.47-7.35 (m, 3H), 6.99 (d, J=15.7 Hz, 1H), 6.64-6.52 (m, 1H), 4.69 (d, J=13.9 Hz, 1H), 4.56 (d, J=14.0 Hz, 1H), 4.18 (dd, J=13.3, 6.7 Hz, 1H), 4.00 (dd, J=13.1, 8.1 Hz, 1H), 2.92 (s, 3H); HRMS (ESI) m/z calcd for $C_{20}H_9NO$ $(M+H)^+$303.1497, found 303.1496.

Example 28

Preparation of (E)-N-methyl-N-[(benzofuran-3-yl)methylene]-3-(4-phenylphenyl)-prop-2-en-1-amine (Compound $I_A$-25)

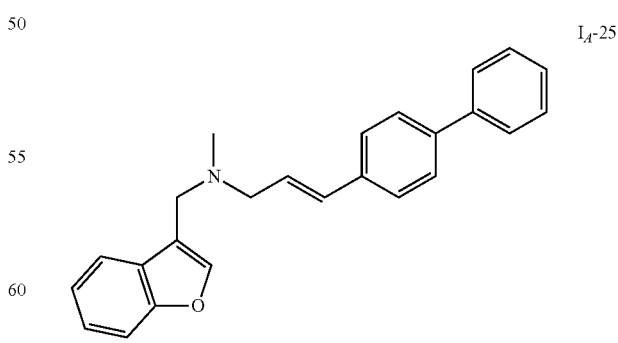

I$_A$-25

In addition to replacement of (E)-3-phenyl-propenal with (E)-3-(4-phenylphenyl)-propenal, the remaining starting materials, reagents and preparation methods as required were the same as in Examples 2-4, and 130 mg colorless oily title compound was obtained with a yield of 43%. The hydrochloride salt of this compound was a white solid.

¹H-NMR (400 MHz, MeOD) δ 8.13 (s, 1H), 7.86-7.77 (m, 1H), 7.67-7.58 (m, 7H), 7.41 (dddd, J=23.2, 15.9, 9.3, 4.8 Hz, 5H), 6.99 (d, J=15.7 Hz, 1H), 6.50-6.34 (m, 1H), 4.68-4.44 (m, 2H), 4.06 (d, J=55.9 Hz, 2H), 2.92 (s, 3H); HRMS (ESI) m/z calcd for $C_{25}H_{24}NO$ (M+H)⁺ 354.1858, found 354.1857.

Example 29

Preparation of (E)-N-methyl-N-[(benzofuran-3-yl)methylene]-3-(2-naphthyl)-prop-2-en-1-amine (Compound $I_A$-26)

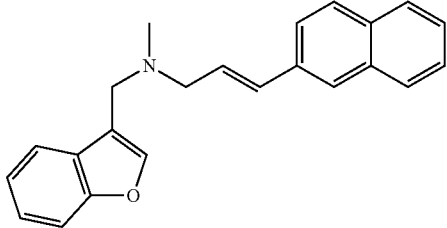

$I_A$-26

In addition to replacement of (E)-3-phenyl-propenal with (E)-3-(2-naphthyl)-propenal, the remaining starting materials, reagents and preparation methods as required were the same as in Examples 2-4, and 89 mg colorless oily title compound was obtained with a yield of 35%. The hydrochloride salt of this compound was a white solid.

¹H-NMR (400 MHz, MeOD) δ 8.14 (s, 1H), 7.91-7.81 (m, 5H), 7.73 (dd, J=8.7, 1.7 Hz, 1H), 7.63-7.59 (m, 1H), 7.53-7.48 (m, 2H), 7.41 (dtd, J=18.2, 7.3, 1.3 Hz, 2H), 7.12 (d, J=15.7 Hz, 1H), 6.60-6.44 (m, 1H); HRMS (ESI) m/z calcd for $C_{23}H_{22}NO$ (M+H)⁺ 328.1701, found 328.1700.

Example 30

Preparation of (E)-N-methyl-N-[(benzofuran-3-yl)methylene]-3-(4-tert-butylphenyl)-prop-2-en-1-amine (Compound $I_A$-27)

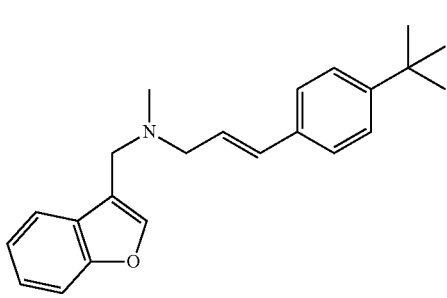

$I_A$-27

In addition to replacement of (E)-3-phenyl-propenal with (E)-3-(4-tert-butylphenyl)-propenal, the remaining starting materials, reagents and preparation methods as required were the same as in Examples 2-4, and 120 mg colorless oily title compound was obtained with a yield of 56%. The hydrochloride salt of this compound was a white solid.

¹H-NMR (400 MHz, MeOD) δ 8.16 (s, 1H), 7.85 (dd, J=7.1, 1.4 Hz, 1H), 7.66-7.59 (m, 1H), 7.47-7.39 (m, 6H), 6.97-6.91 (m, 1H), 6.43-6.31 (m, 1H), 4.70 (d, J=13.9 Hz, 1H), 4.54 (d, J=13.9 Hz, 1H), 4.19-4.10 (m, 1H), 3.99-3.89 (m, 1H), 2.92 (s, 3H), 1.34 (s, 9H); HRMS (ESI) m/z calcd for $C_{23}H_{22}NO$ (M+H)⁺ 334.2171, found 334.2172.

Example 31

Preparation of (E)-N-methyl-N-[(benzofuran-3-yl)methylene]-3-(2-fluorophenyl)-prop-2-en-1-amine (Compound $I_A$-28)

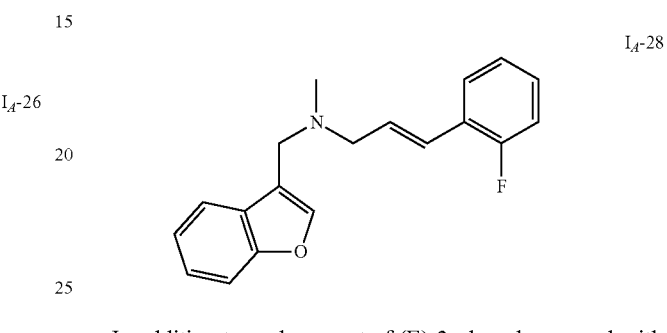

$I_A$-28

In addition to replacement of (E)-3-phenyl-propenal with (E)-3-(2-fluorophenyl)-propenal, the remaining starting materials, reagents and preparation methods as required were the same as in Examples 2-4, and 70 mg colorless oily title compound was obtained with a yield of 28%. The hydrochloride salt of this compound was a white solid.

¹H-NMR (400 MHz, MeOD) δ 8.12 (s, 1H), 7.85-7.76 (m, 1H), 7.68-7.54 (m, 2H), 7.49-7.29 (m, 3H), 7.27-6.99 (m, 3H), 6.56-6.40 (m, 1H), 4.61 (d, J=45.6 Hz, 2H), 4.08 (d, J=69.5 Hz, 2H), 2.91 (s, 3H); HRMS (ESI) m/z calcd for $C_{19}H_{19}FNO$ (M+H)⁺ 296.1451, found 296.1452.

Example 32

Preparation of (E)-N-methyl-N-[(benzofuran-3-yl)methylene]-3-(3-nitrophenyl)-prop-2-en-1-amine (Compound $I_A$-29)

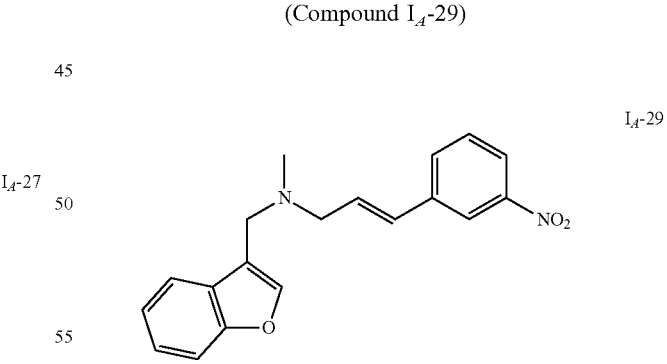

$I_A$-29

In addition to replacement of (E)-3-phenyl-propenal with (E)-3-(3-nitrophenyl)-propenal, the remaining starting materials, reagents and preparation methods as required were the same as in Examples 2-4, and 130 mg colorless oily title compound was obtained with a yield of 65%. The hydrochloride salt of this compound was yellow and oily.

¹H-NMR (400 MHz, MeOD) δ 8.37 (t, J=1.8 Hz, 1H), 8.19 (dd, J=8.2, 2.1 Hz, 1H), 8.11 (s, 1H), 7.91 (d, J=7.8 Hz, 1H), 7.85-7.80 (m, 1H), 7.63 (t, J=8.0 Hz, 1H), 7.58 (d, J=7.5 Hz, 1H), 7.44-7.33 (m, 2H), 7.01 (d, J=15.7 Hz, 1H), 6.64-6.53 (m, 1H), 4.55 (s, 2H), 4.04 (t, J=14.6 Hz, 2H), 2.88 (s, 3H); HRMS (ESI) m/z calcd for $C_{19}H_{19}N_2O_3$ (M+H)$^+$ 323.1396, found 323.1399.

Example 33

Preparation of (E)-N-methyl-N-[(benzofuran-3-yl)methylene]-3-(2-trifluoromethylphenyl)-prop-2-en-1-amine (Compound $I_A$-30)

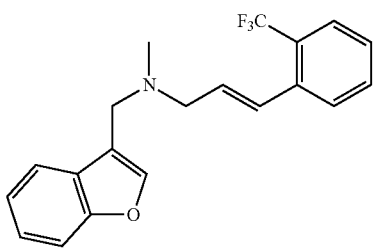

In addition to replacement of (E)-3-phenyl-propenal with (E)-3-(2-trifluoromethylphenyl)-propenal, the remaining starting materials, reagents and preparation methods as required were the same as in Examples 2-4, and 115 mg colorless oily title compound was obtained with a yield of 55%. The hydrochloride salt of this compound was a white solid.

$^1$H-NMR (400 MHz, MeOD) δ 8.15 (d, J=5.1 Hz, 1H), 7.89-7.75 (m, 3H), 7.61 (dt, J=15.2, 7.7 Hz, 3H), 7.40 (dt, J=18.9, 7.3 Hz, 2H), 7.01 (d, J=15.8 Hz, 1H), 6.62-6.46 (m, 1H), 4.70 (d, J=14.0 Hz, 1H), 4.56 (d, J=13.7 Hz, 1H), 4.17 (dd, J=12.9, 7.1 Hz, 1H), 3.99 (dd, J=12.8, 7.8 Hz, 1H), 2.92 (s, 3H); HRMS (ESI) m/z calcd for $C_{20}H_{19}F_3NO$ (M+H)$^+$ 346.1419, found 346.1418.

Example 34

Preparation of (E)-N-methyl-N-[(benzofuran-3-yl)methylene]-3-(2-fluoro-4-trifluoromethyl-phenyl)-prop-2-en-1-amine (Compound $I_A$-31)

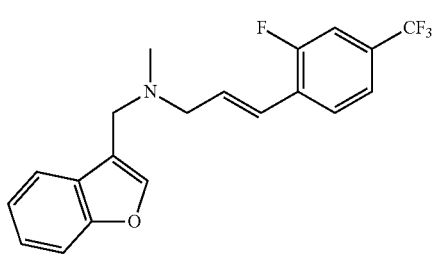

In addition to replacement of (E)-3-phenyl-propenal with (E)-3-(2-fluoro-4-trifluoromethylphenyl)-propenal, the remaining starting materials, reagents and preparation methods as required were the same as in Examples 2-4, and 104 mg colorless oily title compound was obtained with a yield of 43%. The hydrochloride salt of this compound was a white solid.

$^1$H-NMR (400 MHz, MeOD) δ 8.15 (d, J=5.1 Hz, 1H), 7.89-7.75 (m, 3H), 7.61 (dt, J=15.2, 7.7 Hz, 3H), 7.40 (dt, J=18.9, 7.3 Hz, 2H), 7.01 (d, J=15.8 Hz, 1H), 6.61-6.46 (m, 1H), 4.70 (d, J=14.0 Hz, 1H), 4.56 (d, J=13.7 Hz, 1H), 4.23-4.12 (m, 1H), 3.99 (dd, J=12.8, 7.8 Hz, 1H), 2.92 (s, 3H); HRMS (ESI) m/z calcd for $C_{20}H_{18}F_4NO$ (M+H)$^+$ 364.1325, found 364.1326.

Example 35

Preparation of (E)-N-methyl-N-[(benzofuran-3-yl)methylene]-3-cyclopentylprop-2-en-1-amine (Compound $I_A$-32)

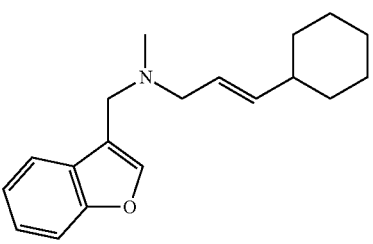

In addition to replacement of (E)-3-phenyl-propenal with (E)-3-cyclopentyl-propenal, the remaining starting materials, reagents and preparation methods were the same as in Examples 2-4, and 80 mg colorless oily title compound was obtained with a yield of 40%. The hydrochloride salt of this compound was yellow and oily.

$^1$H-NMR (400 MHz, MeOD) δ 8.10 (s, 1H), 7.80 (d, J=7.3 Hz, 1H), 7.58 (t, J=9.1 Hz, 1H), 7.47-7.30 (m, 2H), 6.19-5.97 (m, 1H), 5.71-5.53 (m, 1H), 4.52 (d, J=46.0 Hz, 2H), 3.81 (d, J=66.3 Hz, 2H), 2.80 (d, J=14.3 Hz, 3H), 2.65-2.51 (m, 1H), 1.85 (dt, J=11.2, 6.8 Hz, 2H), 1.75-1.50 (m, 5H), 1.44-1.23 (m, 3H); HRMS (ESI) m/z calcd for $C_{19}H_{26}NO$ (M+H)$^+$ 284.2014, found 284.2008.

Example 36

Preparation of (E)-N-methyl-N-[(benzofuran-3-yl)methylene]-3-thiophen-2-en-1-amine (Compound $I_A$-33)

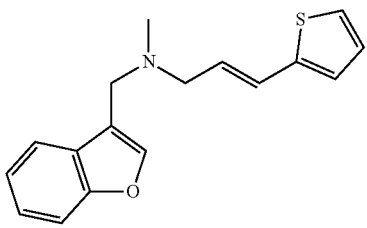

In addition to replacement of (E)-3-phenyl-propenal with (E)-3-thiophen-propenal, the remaining starting materials, reagents and preparation methods as required were the same as in Examples 2-4, and 62 mg yellow oily title compound was obtained with a yield of 31%. The hydrochloride salt of this compound was yellow and oily.

$^1$H-NMR (400 MHz, MeOD) δ 8.12 (s, 1H), 7.80 (d, J=1.2 Hz, 1H), 7.61-7.58 (m, 1H), 7.44 (dd, J=7.2, 1.2 Hz, 1H), 7.39-7.35 (m, 1H), 7.25 (t, J=7.6 Hz, 2H), 7.16 (d,

J=7.5 Hz, 1H), 6.91 (d, J=15.8 Hz, 1H), 6.41-6.31 (m, 1H), 4.66 (t, J=9.5 Hz, 1H), 4.54-4.46 (m, 1H), 4.11 (dt, J=7.0, 5.7 Hz, 1H), 3.94 (dd, J=13.1, 8.2 Hz, 1H), 2.90 (s, 3H); HRMS (ESI) m/z calcd for $C_{17}H_{18}NOS$ (M+H)$^+$ 360.1422, found 360.1421.

Example 37

Preparation of (E)-N-methyl-N-[(benzofuran-3-yl)methylene]-3-(2-methoxyphenyl)-prop-2-en-1-amine (Compound $I_A$-34)

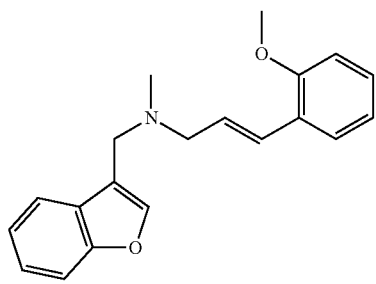

I$_A$-34

In addition to replacement of (E)-3-phenyl-propenal with (E)-3-(2-methoxyphenyl)-propenal, the remaining starting materials, reagents and preparation methods as required were the same as in Examples 2-4, and 121 mg colorless oily title compound was obtained with a yield of 55%. The hydrochloride salt of this compound was a white solid.

$^1$H-NMR (400 MHz, MeOD) δ 8.12 (s, 1H), 7.81 (d, J=7.6 Hz, 1H), 7.60 (d, J=7.9 Hz, 1H), 7.52 (dd, J=7.7, 1.5 Hz, 1H), 7.46-7.29 (m, 3H), 7.21 (d, J=15.9 Hz, 1H), 7.02 (d, J=8.3 Hz, 1H), 6.96 (t, J=7.5 Hz, 1H), 6.40 (dt, J=15.1, 7.5 Hz, 1H), 4.58 (d, J=50.9 Hz, 2H), 4.18-3.90 (m, 2H), 3.87 (s, 3H), 2.90 (s, 3H); HRMS (ESI) m/z calcd for $C_{20}H_{22}NO_2$ (M+H)$^+$ 308.1651, found 308.1649.

Example 38

Preparation of (E)-N-methyl-N-[(benzofuran-3-yl)methylene]-3-(2-fluoro-4-methoxyphenyl)-prop-2-en-1-amine (Compound $I_A$-35)

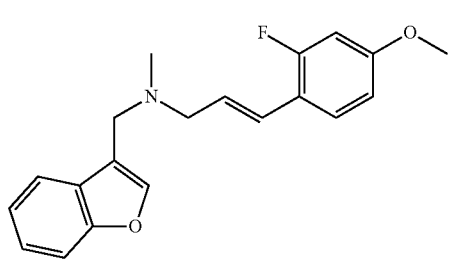

I$_A$-35

In addition to replacement of (E)-3-phenyl-propenal with (E)-3-(2-fluoro-4-methoxyphenyl)-propenal, the remaining starting materials, reagents and preparation methods as required were the same as in Examples 2-4, and 112 mg colorless oily title compound was obtained with a yield of 49%. The hydrochloride salt of this compound was a white solid.

$^1$H-NMR (400 MHz, MeOD) δ 8.14 (s, 1H), 7.83 (d, J=7.3 Hz, 1H), 7.60 (d, J=8.1 Hz, 1H), 7.39 (tt, J=17.3, 8.7 Hz, 2H), 7.32-7.21 (m, 1H), 7.08 (dd, J=9.8, 5.0 Hz, 2H), 6.93 (s, 1H), 6.47-6.31 (m, 1H), 4.60 (d, J=43.9 Hz, 2H), 3.99 (dd, J=41.1, 32.3 Hz, 2H), 3.82 (d, J=6.1 Hz, 3H), 2.91 (d, J=9.1 Hz, 3H); HRMS (ESI) m/z calcd for $C_{20}H_{21}FNO_2$ (M+H)$^+$ 326.1556, found 326.1554.

Example 39

Preparation of (E)-N-methyl-N-[(benzofuran-3-yl)methylene]-3-(2-methylphenyl)-prop-2-en-1-amine (Compound $I_A$-36)

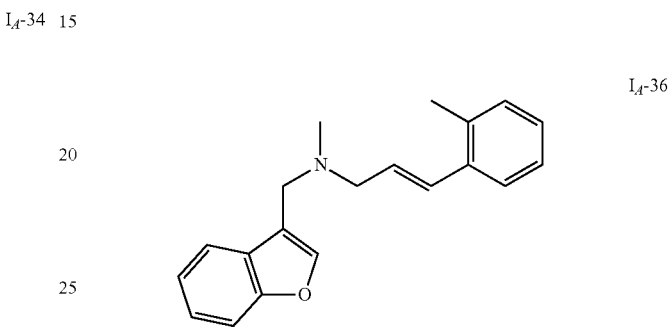

I$_A$-36

In addition to replacement of (E)-3-phenyl-propenal with (E)-3-(2-methylphenyl)-propenal, the remaining starting materials, reagents and preparation methods as required were the same as in Examples 2-4, and 95 mg colorless oily title compound was obtained with a yield of 45%. The hydrochloride salt of this compound was a white solid.

$^1$H-NMR (400 MHz, CDCl3) δ 7.70 (dd, J=15.7, 7.5 Hz, 1H), 7.56 (d, J=8.7 Hz, 1H), 7.47 (t, J=7.1 Hz, 2H), 7.32-7.27 (m, 1H), 7.26-7.22 (m, 1H), 7.18-7.11 (m, 3H), 6.77 (d, J=15.7 Hz, 1H), 6.20 (dt, J=15.7, 6.6 Hz, 1H), 3.71 (s, 2H), 3.27 (d, J=6.6 Hz, 2H), 2.34 (s, 3H), 2.32 (s, 3H); HRMS (ESI) m/z calcd for $C_{20}H_{22}NO$ (M+H)$^+$ 292.1701, found 292.1702.

Example 40

Preparation of (E)-N-methyl-N-[(benzofuran-3-yl)methylene]-3-(3-methylphenyl)-prop-2-en-1-amine (Compound $I_A$-37)

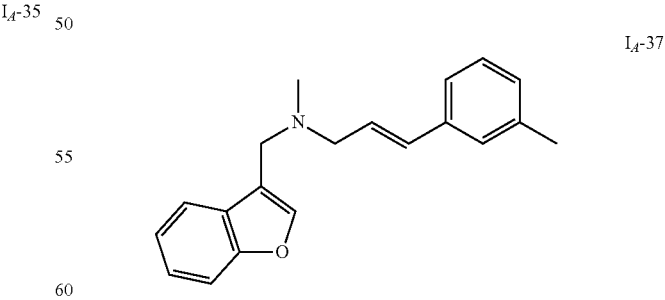

I$_A$-37

In addition to replacement of (E)-3-phenyl-propenal with (E)-3-(3-methylphenyl)-propenal, the remaining starting materials, reagents and preparation methods as required were the same as in Examples 2-4, and 116 mg colorless oily title compound was obtained with a yield of 53%. The hydrochloride salt of this compound was a white solid.

¹H-NMR (400 MHz, MeOD) δ 8.12 (s, 1H), 7.81 (d, J=7.2 Hz, 1H), 7.60 (d, J=8.1 Hz, 1H), 7.47-7.33 (m, 4H), 7.19 (d, J=7.9 Hz, 2H), 6.90 (d, J=15.8 Hz, 1H), 6.32 (dt, J=15.5, 7.6 Hz, 1H), 4.67 (d, J=13.9 Hz, 1H), 4.51 (d, J=13.9 Hz, 1H), 4.11 (dd, J=13.0, 7.0 Hz, 1H), 3.93 (dd, J=12.9, 7.9 Hz, 1H), 2.89 (s, 3H), 2.34 (s, 3H); HRMS (ESI) m/z calcd for $C_{20}H_{22}NO$ (M+H)+292.1701, found 292.1702.

Example 41

Preparation of (E)-N-methyl-N-[(benzofuran-3-yl)methylene]-3-(3-fluoro-4-methoxyphenyl)-prop-2-en-1-amine (Compound $I_A$-38)

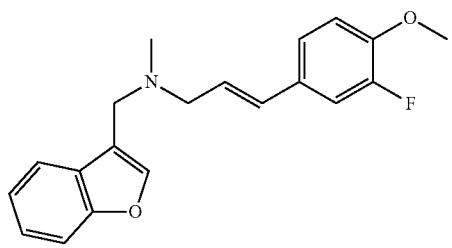

$I_A$-38

In addition to replacement of (E)-3-phenyl-propenal with (E)-3-(3-fluoro-4-methoxyphenyl)-propenal, the remaining starting materials, reagents and preparation methods as required were the same as in Examples 2-4, and 126 mg colorless oily title compound was obtained with a yield of 61%. The hydrochloride salt of this compound was a white solid.

¹H-NMR (400 MHz, MeOD) δ 7.98 (s, 1H), 7.77 (d, J=7.4 Hz, 1H), 7.55 (d, J=7.9 Hz, 1H), 7.40-7.36 (m, 1H), 7.34 (dd, J=7.5, 1.0 Hz, 1H), 7.29 (dd, J=12.5, 2.0 Hz, 1H), 7.20 (d, J=8.8 Hz, 1H), 7.09-7.03 (s, 1H), 6.72 (d, J=15.8 Hz, 1H), 6.29-6.19 (m, 1H), 4.68-4.55 (m, 2H), 4.28 (d, J=4.7 Hz, 2H), 3.88 (s, 3H), 2.68 (s, 3H); HRMS (ESI) m/z calcd for $C_{20}H_{21}FNO_2$ (M+H) 326.1556, found 326.1554.

Example 42

Preparation of (2E,4E)-5-([1,1'-biphenyl]-4-yl)-N-(benzofuran-3-ylmethyl)-N-methylpenta-2,4-dien-1-amine (Compound $I_A$-39)

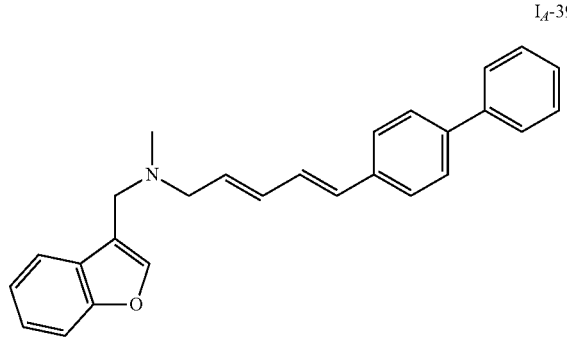

$I_A$-39

In addition to replacement of (E)-3-phenyl-propenal with (2E,4E)-5-phenyl-pentyl-2,4-dien-1-ol, the remaining starting materials, reagents and preparation methods as required were the same as in Examples 3-4, and 52 mg colorless oily title compound was obtained with a yield of 31%. The hydrochloride salt of this compound was a white solid.

¹H-NMR (400 MHz, MeOD) δ 7.60 (dd, J=12.1, 7.9 Hz, 5H), 7.51 (d, J=8.1 Hz, 2H), 7.42 (t, J=7.5 Hz, 2H), 7.33 (d, J=7.6 Hz, 1H), 7.14 (dd, J=20.8, 7.8 Hz, 2H), 6.97-6.88 (m, 1H), 6.75 (d, J=7.6 Hz, 2H), 6.64 (d, J=16.0 Hz, 1H), 6.55-6.40 (m, 1H), 5.94 (s, 1H), 4.61 (s, 2H), 3.38 (d, J=6.5 Hz, 2H), 2.42 (s, 3H); HRMS (ESI) m/z calcd for $C_{27}H_{26}NO$ (M+H)+ 380.2014, found 380.2012.

Example 43

Preparation of (E)-4-([1,1'-biphenyl]-4-yl)-N-(benzofuran-3-ylmethyl)-N-methylbut-3-en-1-amine (Compound $I_A$-40)

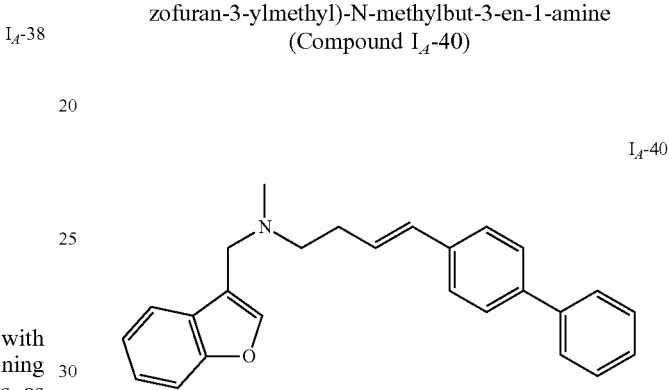

$I_A$-40

In addition to replacement of (E)-3-phenyl-propenal with (2E,4E)-5-phenyl-pentyl-4-en-1-ol, the remaining starting materials, reagents and preparation methods as required were the same as in Examples 3-4, and 70 mg colorless oily title compound was obtained with a yield of 41%. The hydrochloride salt of this compound was a white solid.

¹H-NMR (400 MHz, MeOD) δ 8.13 (s, 1H), 7.86-7.77 (m, 1H), 7.67-7.58 (m, 7H), 7.41 (dddd, J=23.2, 15.9, 9.3, 4.8 Hz, 5H), 6.99 (d, J=15.7 Hz, 1H), 6.45-6.28 (m, 1H), 4.68-4.44 (m, 2H), 3.26 (t, J=55.9 Hz, 2H), 2.92 (s, 3H), 2.36 (m, 2H); HRMS (ESI) m/z calcd for $C_{26}H_{26}NO$ (M+H) 368.2014, found 368.2013.

Example 44

Preparation of (E)-N-(benzo[b]thiophen-3-ylmethyl)-N-methyl-3-(4-(trifluoromethyl)phenyl)prop-2-en-1-amine (Compound $I_A$-41)

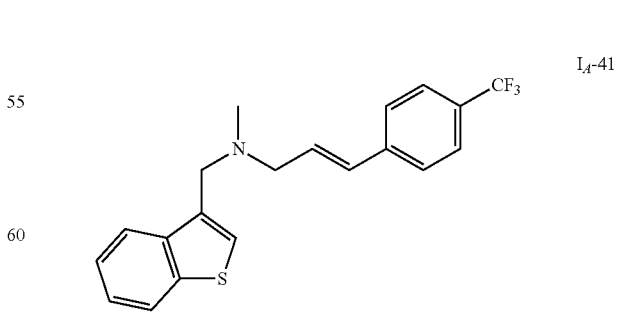

$I_A$-41

In addition to replacement of the substrate benzofuran-3-carboxaldehyde with benzothiophene-3-carboxaldehyde, and replacement of (E)-3-phenyl-propenal with (E)-3-(4- trifluoromethylphenyl)-propenal, the remaining starting materials, reagents and preparation methods as required were the same as those in Examples 1-4, and 34 mg of colorless oily title compound was obtained with a yield of 31%. The hydrochloride salt of this compound was a white solid.

$^1$H-NMR (400 MHz, MeOD) δ 8.02 (s, 3H), 7.68 (s, 3H), 7.50 (d, J=19.3 Hz, 2H), 6.99 (d, J=16.0 Hz, 1H), 6.53 (s, 1H), 4.71 (d, J=53.3 Hz, 2H), 4.09 (d, J=40.8 Hz, 2H), 2.90 (s, 3H); HRMS (ESI) m/z calcd for $C_{20}H_{19}F_3NS$ (M+H)$^+$ 362.1190, found 360.1193.

Example 45

Preparation of (E,E)-N-(3-4-trifluoromethylphenyl-prop-2-en-1-ylidene)-(6,7,8,9-tetrahydro-5H-benzo[3]annulen-1-yl)methylamine (Intermediate X-1)

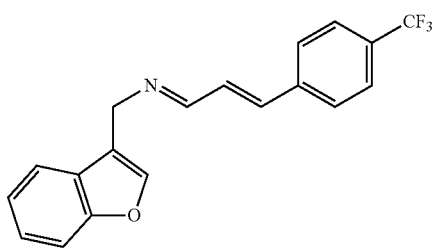

294 mg of Intermediate II, 264 mg of trans-4-trifluoromethylcinnamaldehyde, and 1 g of molecular sieves were added to 25 mL of dichloromethane solution, and the mixture was heated under reflux to react for 17 h; after completion of the reaction, the reaction system was cooled to room temperature, filtered, and concentrated, and the reaction products was used directly in the next step without isolation and purification.

Example 46

Preparation of (E)-N-[(benzofuran-3-yl)methylene]-3-(4-trifluoromethylphenyl)-prop-2-en-1-amine (Compound I$_B$-1)

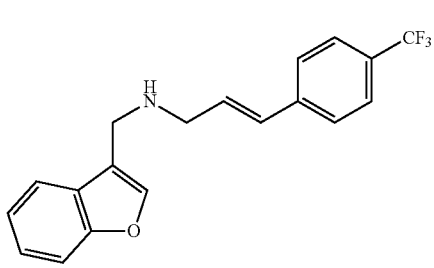

Intermediate V was dissolved in methanol, 76 mg of sodium borohydride was added in batches under ice bath, and the mixture reacted at room temperature for 10-30 min, followed by concentration; the residue was added with water, extracted with ethyl acetate for 3 times, washed with a saturated salt solution, dried over anhydrous sodium sulfate, and then filtered to obtain 97 mg of yellow oily title compound with a yield of 96%. The hydrochloride salt of this compound was a yellow solid.

$^1$H-NMR (400 MHz, MeOD) δ 8.15 (s, 1H), 7.88-7.78 (m, 1H), 7.61 (s, 1H), 7.36-7.33 (m, 2H), 6.94 (dd, J=7.5, 1.0 Hz, 1H), 6.89 (d, J=8.1 Hz, 1H), 6.82 (d, J=23.9 Hz, 2H), 5.65 (s, 1H), 4.62 (d, J=37.6 Hz, 2H), 4.03 (d, J=72.0 Hz, 2H); HRMS (ESI) m/z calcd for $C_{19}H_{17}F_3NO$ (M+H)$^+$332.1262, found 362.1263.

Example 47

Preparation of (E)-N-ethyl-N-[(benzofuran-3-yl)methylene]-3-(4-trifluoromethylphenyl)-prop-2-en-1-amine (Compound I$_B$-2)

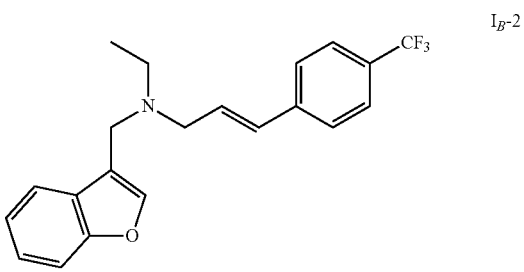 [SMILES: CCN(C/C=C/c1ccc(C(F)(F)F)cc1)Cc1coc2ccccc12]

360 mg of Compound I$_B$-1 was dissolved in 10 mL of anhydrous N, N-dimethylformamide, 56 mg of sodium hydride was added in batches under ice-bath, and the mixture was stirred for 15 min reaction; 0.6 mL of iodoethane was then added, and the mixture reacted overnight at room temperature under nitrogen protection; after completion of the reaction, the reaction system was added with water, extracted with ethyl acetate for 3 times, washed with a saturated saline solution, dried over anhydrous sodium sulfate followed by filtration and concentration; and the residue was purified by column chromatography to obtain 200 mg oily title compound with a yield of 50%. The hydrochloride salt of the compound was a yellowish-brown oil.

$^1$H-NMR (400 MHz, MeOD) δ 8.15 (s, 1H), 7.80 (d, J=7.6 Hz, 1H), 7.59 (d, J=6.4 Hz, 2H), 7.44 (ddd, J=9.5, 5.9, 2.2 Hz, 3H), 7.41-7.33 (m, 2H), 6.98 (d, J=15.8 Hz, 1H), 6.51-6.33 (m, 1H), 4.63 (s, 2H), 4.06 (dd, J=7.0, 3.4 Hz, 2H), 3.37 (q, J=7.3 Hz, 2H), 1.47 (t, J=7.3 Hz, 3H); HRMS (ESI) m/z calcd for $C_{21}H_{21}NO$ (M+H)$^+$ 360.1575, found 360.1576.

Example 48

Preparation of (E)-N-isopropyl-N-[(benzofuran-3-yl)methylene]-3-(4-trifluoromethylphenyl)-prop-2-en-1-amine (Compound I$_B$-3)

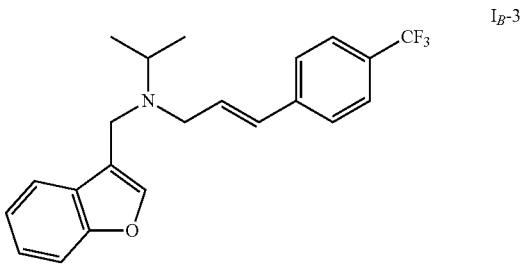 [SMILES: CC(C)N(C/C=C/c1ccc(C(F)(F)F)cc1)Cc1coc2ccccc12]

In addition to replacement of ethyl iodide with 2-iodopropane, the remaining starting materials, reagents and preparation methods as required were the same as in Example 47, and 210 mg yellow oily title compound was obtained with a yield of 50%. The hydrochloride salt of this compound was a light yellow solid.

$^1$H-NMR (400 MHz, MeOD) δ 8.03 (d, J=5.7 Hz, 1H), 7.82 (d, J=7.3 Hz, 1H), 7.77 (d, J=7.2 Hz, 1H), 7.58 (dd, J=7.9, 2.4 Hz, 1H), 7.37 (dddd, J=33.9, 26.7, 12.6, 5.2 Hz, 4H), 7.20 (t, J=7.9 Hz, 1H), 6.92 (td, J=7.1, 4.0 Hz, 1H), 6.81 (d, J=8.1 Hz, 1H), 4.71-4.58 (m, 1H), 4.57-4.44 (m, 3H), 3.95-3.79 (m, 1H), 3.31 (d, J=1.6 Hz, 6H); HRMS (ESI) m/z calcd for $C_{22}H_{23}F_3NO$ (M+H)$^+$374.1732, found 374.1733.

Example 49

Preparation of (1R,2R)-2-(1,1'-biphenyl)-1-hydroxymethylcyclopropane (Intermediate VI-1)

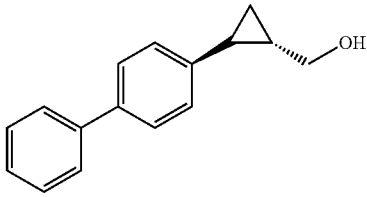

1.8 mL of diethyl zinc (1.1 M) n-hexane solution was added to 10 mL of dichloromethane, 0.15 mL of trifluoroacetic acid and 0.16 mL of diiodomethane were slowly added under nitrogen protection, and the mixture reacted at 5° C. for 30 min; 1,1'-biphenyl cinnamyl alcohol was dissolved in dichloromethane and slowly added dropwise to the above solution, and the mixture reacted for 3 h; after completion of the reaction, the reaction system was added with water, extracted with ethyl acetate for three times, washed with a saturated saline solution, and dried over anhydrous sodium sulfate followed by filtration and concentration; the residue was purified by column chromatography to obtain 197 mg of colorless oily title compound with a yield of 88%.

$^1$H-NMR (400 MHz, CDCl3) δ 7.57 (d, J=7.21-Hz, 2H), 7.50 (d, J=8.2 Hz, 21-H), 7.43 (t, J=7.6 Hz, 3H), 7.33 (t, J=7.4 Hz, 1H), 7.15 (d, J=8.2 Hz, 2H), 3.69-3.61 (m, 2H), 1.92-1.83 (m, 1H), 1.50 (d, J=5.8 Hz, 1H), 1.00 (ddt, J=13.9, 10.7, 5.2 Hz, 2H).

Example 50

Preparation of (1R,2R)-2-(1,1'-biphenyl)-1-bromomethylcyclopropane (Intermediate VII-1)

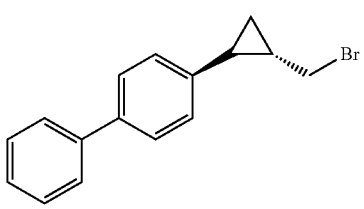

645 mg of carbon tetrabromide was dissolved in 20 mL of dichloromethane, 786 mg of triphenylphosphine was added in batches under stirring; after stirring for 15 min, an intermediate (1S,2S)-2-(1,1'-biphenyl)-1-hydroxymethyl cyclopropane was added, and the mixture reacted for 1-3 h; 212 mg of yellow oily title compound was obtained with a yield of 74%, which was used directly in the following reaction without further treatment.

Example 51

Preparation of 1-((1R,2R)-2-([1,1'-biphenyl]-4-yl) cyclopropyl)-N-(benzofuran-3-ylmethyl)-N-methyl-methanamine (Compound I$_C$-1)

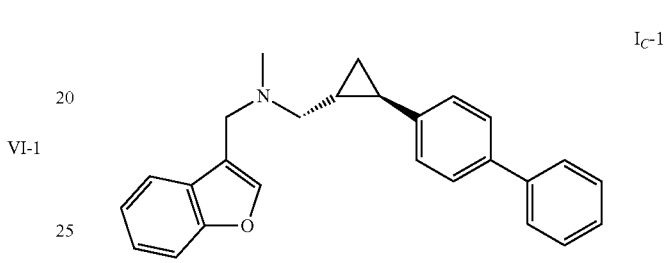

In addition to replacement of Intermediate VI-1 with Intermediate VIII-1, the remaining starting materials, reagents and preparation methods as required were the same as in Example 4, and 112 mg yellow oily title compound was obtained with a yield of 52%. The hydrochloride salt of this compound was a yellow oil.

$^1$H-NMR (400 MHz, MeOD) δ 7.86 (t, J=4.1 Hz, 1H), 7.83-7.75 (m, 3H), 7.53-7.41 (m, 3H), 7.42-7.31 (m, 1H), 7.28 (td, J=7.5, 1.7 Hz, 2H), 7.22-7.11 (m, 3H), 6.97 (td, J=5.3, 2.2 Hz, 1H), 4.85 (dd, J=16.5, 6.5 Hz, 1H), 4.58 (dd, J=13.3, 5.0 Hz, 1H), 3.52-3.45 (m, 1H), 3.29-3.15 (m, 1H), 2.90 (d, J=7.3 Hz, 3H), 2.13-2.03 (m, 1H), 1.62-1.49 (m, 1H), 1.18-1.06 (m, 1H), 0.94-0.81 (m, 1H); HRMS (ESI) m/z calcd for $C_{26}H_2NO$ (M+H)+368.2014, found 368.2016.

Example 52

Preparation of O-TBDMS-3-(1,1'-biphenyl)-propanol-2-yne (Intermediate VIII-1)

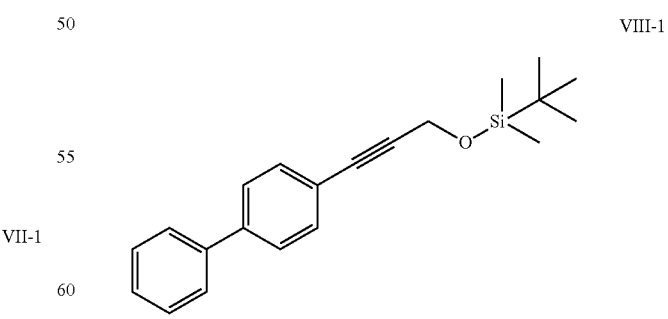

280 mg of intermediate 4-iodo-1,1'-biphenyl and 170 mg of tert-butyldimethyl (prop-2-yn-1-yloxy) silane were dissolved in 10 mL of N,N-dimethylformamide, 57 mg of cuprous iodide, 124 mg of tetrakis (triphenylphosphine) palladium and 10 mL of triethylamine were added respectively, and the mixture reacted at 80° C. for 4-6 h; after completion of the reaction, the reaction system was added with water, extracted with ethyl acetate for three times, washed with a saturated saline solution, and dried over anhydrous sodium sulfate followed by filtration and concentration; and the residue was purified by column chromatography to obtain 302 mg brown oily title compound with a yield of 94%.

Example 53

Preparation of 3-(1,1'-biphenyl)-propanol-2-yne (Intermediate IX-1)

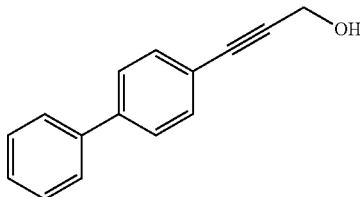

322 mg of intermediate O-TBDMS-3-(1,1'-biphenyl)-propanol-2-yne was dissolved in 10 mL of tetrahydrofuran, the mixture was stirred under nitrogen protection and at a temperature of less than 5° C., an appropriate amount of tetrabutylammonium fluoride was added, and the reaction was carried out for 1-3 h; after completion of the reaction, the reaction system was added with water, extracted with ethyl acetate for three times, washed with a saturated saline solution, and dried over anhydrous sodium sulfate followed by filtration and concentration; and the residue was purified by column chromatography to obtain 204 mg of colorless oily title compound with a yield of 98%.

Example 54

Preparation of 1-phenyl-3-bromopropyne (Intermediate X-1)

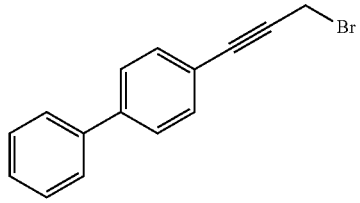

In addition to replacement of Intermediate III-1 with Intermediate IX-1, the remaining strating materials, reagents and preparation methods as required were the same as in Example 3, and 211 mg yellow oily title compound was obtained with a yield of 84%.

Example 55

Preparation of N-methyl-N-[(6,7,8,9-tetrahydro-5H-benzo[3]annulen-2-yl)methyl]-3-(4-phenylphenyl)-propane 2-yn-1-amine (Compound $I_D$-1)

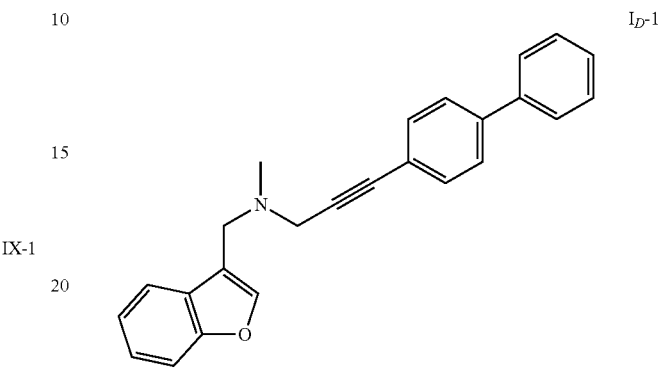

In addition to replacement of Intermediate IV-1 with Intermediate ix-1, the remaining starting materials, reagents and preparation methods as required were the same as in Example 4, and 120 mg colorless oily title compound was obtained with a yield of 59%. The hydrochloride salt of this compound was a white solid.

$^1$H-NMR (400 MHz, MeOD) δ 7.70-7.56 (m, 7H), 7.46 (dd, J=10.3, 4.8 Hz, 2H), 7.37 (dd, J=8.3, 6.4 Hz, 1H), 7.32 (dd, J=7.6, 1.6 Hz, 1H), 7.27-7.18 (m, 1H), 6.97-6.82 (m, 2H), 5.64 (t, J=9.1 Hz, 2H), 4.41 (s, 2H), 2.92 (s, 3H); HRMS (ESI) m/z calcd for $C_{25}H_{22}NO$ (M+H)+352.1701, found 352.1702.

Example 56

Preparation of 3-(1,1'-biphenyl)-propanol (Intermediate XI-1)

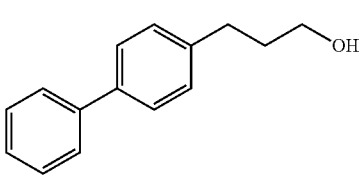

(E)-(1,1'-biphenyl)-cinnamyl alcohol was dissolved in methanol, a catalytic amount of palladium carbon was added, hydrogen was introduced for replacement of air, and the mixture reacted for 8-10 h at 20-30° C., followed by filtration and concentration; and the residue was purified by column chromatography to obtain 204 mg colorless oily title compound with a yield of 96%.

$^1$H-NMR (400 MHz, CDCl3) δ 7.58 (d, J=7.2 Hz, 2H), 7.53 (d, J=8.0 Hz, 2H), 7.43 (t, J=7.6 Hz, 2H), 7.33 (t, J=7.4 Hz, 1H), 7.28 (d, J=8.0 Hz, 2H), 3.78-3.67 (m, 2H), 2.82-2.71 (m, 2H), 2.02-1.87 (m, 2H).

Example 57

Preparation of 3-(1,1'-biphenyl)-1-bromopropane (Intermediate XII-1)

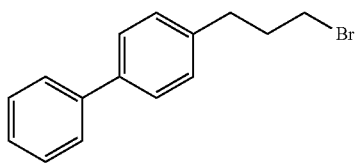

654 mg of carbon tetrabromide was dissolved in 10 mL of dichloromethane, 786 mg of triphenylphosphine was added in batches under stirring, 212 mg of intermediate 3-(1,1'-biphenyl)-propanol was added after stirring for 15 min, and the mixture reacted for 1 to 3 h, followed by filtration and concentration; and the residue was purified by column chromatography to obtain 206 mg title compound as a white solid with a 75% yield.

$^1$H-NMR (400 MHz, CDCl3) δ 7.61-7.50 (m, 1H), 7.43 (t, J=7.6 Hz, 1H), 7.35-7.05 (m, 5H), 3.43 (t, J=6.6 Hz, 1H), 2.83 (t, J=7.3 Hz, 1H), 2.36 (s, 3H), 2.24-2.16 (m, 1H).

Example 58

Preparation of 3-([1,1'-biphenyl]-4-yl)-N-(benzofuran-3-ylmethyl)-N-methylpropan-1-amine (Compound $I_E$-1)

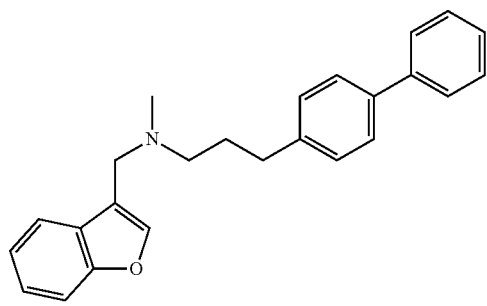

In addition to replacement of Intermediate IX-1 with Intermediate XII-1, the remaining starting materials, reagents and preparation methods as required were the same as in Example 4, and 126 mg colorless oily title compound was obtained with a yield of 60%. The hydrochloride salt of this compound was a white solid.

$^1$H-NMR (400 MHz, MeOD) δ 7.62-7.53 (m, 4H), 7.43 (t, J=7.6 Hz, 2H), 7.23 (dddd, J=13.9, 11.2, 9.5, 4.5 Hz, 5H), 6.88-6.81 (m, 2H), 4.62 (s, 1H), 4.27 (s, 1H), 3.17-3.02 (m, 2H), 2.78 (s, 3H), 2.69 (dd, J=9.4, 5.6 Hz, 2H), 2.12-1.94 (m, 2H). HRMS (ESI) m/z calcd for $C_{25}H_{26}NO$ $(M+H)^+$ 356.2014, found 356.2014.

Example 59

Preparation of (E)-N-(benzofuran-2-ylmethyl)-N-methyl-3-(4-(trifluoromethyl)phenyl)prop-2-en-1-amine (Compound $I_F$-1)

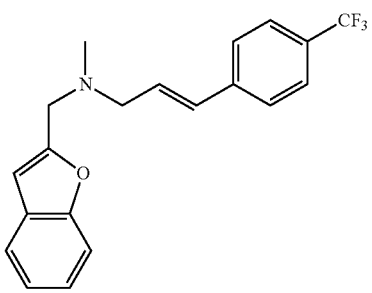

In addition to replacement of the substrate benzofuran-3-carboxaldehyde with benzofuran-2-carboxaldehyde, and replacement of (E)-3-phenyl-propenal with (E)-3-(4-trifluoromethylphenyl)-propenal, the remaining starting materials, reagents and preparation methods as required were the same as in Examples 1-4, and 84 mg colorless oily title compound was obtained with a yield of 62%. The hydrochloride salt of this compound was a white solid.

$^1$H-NMR (400 MHz, MeOD) δ 7.72-7.63 (m, 5H), 7.60-7.54 (m, 1H), 7.45-7.36 (m, 1H), 7.35-7.27 (m, 1H), 7.20 (s, 1H), 7.02 (d, J=15.8 Hz, 1H), 6.56-6.46 (m, 1H), 4.66 (s, 2H), 4.10 (dd, J=14.3, 7.1 Hz, 2H), 2.95 (s, 3H); HRMS (ESI) m/z calcd for $C_{20}H_{19}F_3NO$ $(M+H)^+$ 346.1419, found 346.1418.

Example 60

Preparation of (E)-N-(benzo[b]thiophen-2-ylmethyl)-N-methyl-3-(4-(trifluoromethyl)phenyl)prop-2-en-1-amine (Compound $I_F$-2)

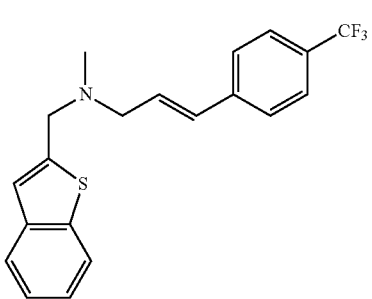

In addition to replacement of the substrate benzofuran-3-carboxaldehyde with benzothiophene-2-carboxaldehyde, and replacement of (E)-3-phenyl-propenal with (E)-3-(4-trifluoromethylphenyl)-propenal, the remaining strating materials, reagents and preparation methods as required were the same as in Examples 1-4, and 112 mg colorless oily title compound was obtained with a yield of 72%. The hydrochloride salt of this compound was a white solid.

$^1$H-NMR (400 MHz, MeOD) δ 7.99-7.85 (m, 2H), 7.75-7.63 (m, 5H), 7.49-7.37 (m, 2H), 7.02 (d, J=15.8 Hz, 1H), 6.53 (dt, J=15.2, 7.4 Hz, 1H), 4.73 (s, 2H), 4.02 (s, 2H), 2.94 (s, 3H); HRMS (ESI) m/z calcd for $C_{20}H_{19}F_3NS$ $(M+H)^+$ 362.1190, found 360.1193.

Example 61 Preliminary Screening Assay of the Compounds of the Invention Having Activity of Inhibiting Staphyloxanthin Synthesis Strains used for assay: freshly activated wild-type *Staphylococcus aureus* subsp. *aureus* str. strain Newman and its homologous mutant strain having crtN insertion (without staphyloxanthin synthesis).

Medium for assay: Tryptone Soy broth (TSB), a product from Oxid Corporation, the United Kingdom, which was formulated with distilled water, sterilized at 121° C. for 15 min for later use.

Method of Preliminary Screening Assay:

(1) Preparation of compound: the compound of the invention was dissolved in dimethyl sulfoxide (DMSO) to prepare a stock solution having a concentration of 10 mM; 400 µL of DMSO was added to 100 µL of the stock solution to get a dilution with a concentration of 2 mM; 250 µL (2 mM) of the dilution was taken after mixing, and an equal amount of DMSO was added thereto for 2-fold dilution to get a solution with a concentration of 0.0625 mM for later use.

(2) Culture of the strain: single colonies of strain Newman were picked from TSA plates into a test tube containing 4 mL of sterile TSB medium, and cultured at 37° C. and 250 rpm for 12 h for later use.

(3) Preliminary screening of the compounds of the invention with the ability of inhibiting staphyloxanthin synthesis in *S. aureus*: the sterile test tubes were taken, and each of them was added with 3980 µL of fresh and sterilized TSB medium; subsequently, 20 µL of a prepared compound solution having a concentration of 10 mM, 2 mM, 1 mM, 0.5 mM, 0.25 mM, 0.125 mM, or 0.0625 mM was added respectively to each test tube, so that the final concentrations of the compound of the invention were 50 µM, 10 µM, 5 µM, 2.5 µM, 1.25 µM, 0.625 µM, and 0.3125 µM, respectively; at the same time, 20 µL of DMSO solution (final concentration: 0.5%) was added to another test tube as a negative control without the compound; 40 µL of the bacteria liquid, which had been cultured for 12 h, was added into each test tube (inoculation amount:medium=1:100), and cultured at 37° C. and 250 rpm for 24 h; 1.5 mL of the bacterial liquid was taken out, and centrifuged at 14,000 g for 2 min; the supernatant was removed, so as to observe whether there is a significant decrease in staphyloxanthin synthesized by the strains as compared to the negative control after the addition of a specific concentration of the compound of the invention.

Figure 2:
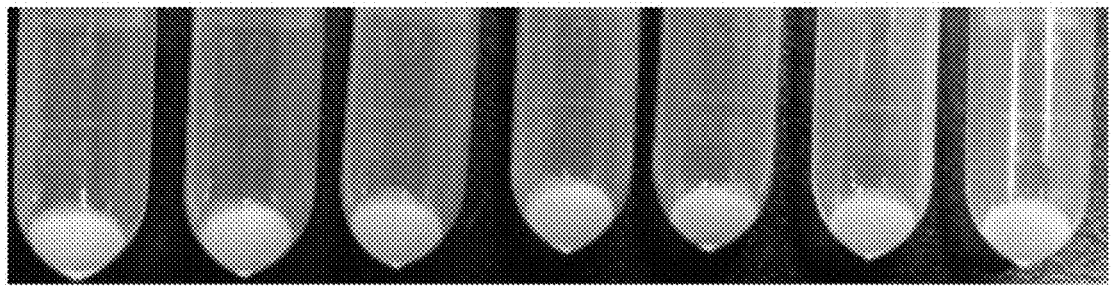
FIG. 2 shows the final photograph of inhibition of staphyloxanthin synthesis by Compound $I_C$-1 of the invention, with the concentrations of 50 μM, 10 μM, 5 μM, 2.5 μM, 1.25 μM, 0.625 μM, 0.3125 μM, and 0 μM from left to right successively and the colors of white to yellow from left to right gradually.

Example 62 Results of Preliminary Screening Assay of Compounds $I_A$-25 and $I_C$-1 of the Invention Having Activity of Inhibiting Staphyloxanthin Synthesis The final photographs of inhibition of staphyloxanthin synthesis by Compounds $I_A$-25 and $I_C$-1 were shown in FIGS. 1 and 2, respectively, wherein the concentrations of the compounds are 50 µM, 10 µM, 5 µM, 2.5 µM, 1.25 µM, 0.625 µM, 0.3125 µM, and 0 µM from left to right successively.

The results showed that Compound $I_A$-25 of the invention can inhibit significantly staphyloxanthin synthesis at a concentration as low as 0.3125 µM.

Example 63 Method for $IC_{50}$ Determination Assay of the Compound of the Invention Having Activity of Inhibiting Staphyloxanthin Synthesis Selection of compound concentrations: based on the preliminary screening results, the ability of each compound to inhibit staphyloxanthin synthesis was determined. For the compounds with stronger activity, if they still strongly inhibited staphyloxanthin synthesis at the lowest concentration during the preliminary screening, the assay can be continued in a manner similar to the preliminary screening until the compound could not substantially inhibit staphyloxanthin production. According to the assay results, 10 different concentration gradients were designed for each compound, such that the ability to inhibit staphyloxanthin synthesis comprised substantially from 0% to 100%.

Culture of the strains: single colonies of strain Newman and crtN mutant strain were picked from TSA plates, added into test tubes containing 4 mL of sterile TSB medium, and cultured at 37° C. and 250 rpm for 12 h for later use.

$IC_{50}$ determination: sterile test tubes were taken, and 3980 µL of fresh and sterilized TSB medium was added into each sterile test tube; subsequently, 20 µL of the prepared compound of the invention with 10 concentrations gradients were added to the test tubes, respectively; at the same time, 20 µL of DMSO solution (final concentration: 0.5%) was added into the other two test tubes as controls without the compound; into the two test tubes with DMSO solution, 40 µL of strain Newman (negative control) and crtN mutant strain (positive control) which had been cultured for 12 h were added; into the remaining test tubes in which the compounds were added, 40 µL of strain Newman which had been cultured for 12 h was added, respectively; all the test tubes were cultured at 37° C. and 250 rpm for 12 h, then at 30° C. and 250 rpm for 36 h to increase the accumulation of staphyloxanthin; after completion of the culture, 3 mL of the bacteria liquid was added into a 5 mL EP tube, and centrifuged at 14,000 g for 2 min, the supernatant was removed; the residue was washed twice with PBS buffer (1 mL per time), added with 300 µL of methanol solution, vortexed for mixing, heated in a water bath at 55° C. for 3 min to extract staphyloxanthin, and then centrifuged at 14,000 g for 2 min; the methanol extract was pipetted into a 1.5 mL EP tube, into which an equal amount of methanol solution was added to repeat the extraction twice, and the three staphyloxanthin extracts were combined; the methanol extract for crtN mutant strain was used as a blank control, the absorbance values of various samples at a wavelength of 450 nm were measured, and the absorbance value of the compound-free negative control was measured. The relative level of staphyloxanthin synthesis at each concentration of the compound of the invention=A450 (sample)/A450 (negative control) *100%. With the molar concentration of the compound as the abscissa and the relative level of staphyloxanthin synthesis as the ordinate, a curve fitting of inhibitor concentration-inhibition rate (log(inhibitor) vs response) was performed in Graphpad prism 5.0 software, and the $IC_{50}$ of the compound for inhibiting staphyloxanthin synthesis was calculated by software based on the fitting results.

Example 64 Results of $IC_{50}$ Determination Assay of the Compounds According to the Invention with Respect to Activity of Inhibiting Staphyloxanthin Synthesis

*S. aureus* was selected for $IC_{50}$ determination with respect to activity of inhibiting staphyloxanthin synthesis. The data on activity are shown in Table 1. A total of 19 compounds of the invention were found to have potent activity of inhibiting staphyloxanthin synthesis, wherein there were 10 active compounds with a half effective inhibitory concentration of $IC_{50}$<10 nM, 7 active compounds with a half effective inhibition concentration of 10 nM<$IC_{50}$<100 nM, and 2 active compounds with a half effective inhibition concentration of 100 nM<$IC_{50}$<1000 nM.

TABLE 1

Data on inhibitory activity of benzofuran-3-alkylamine compounds on staphyloxanthin synthesis ($IC_{50}$, nM)

| Compound No. | $IC_{50}$ (nM) |
|---|---|
| $I_A$-1 | >1000 |
| $I_A$-2 | 9.8 ± 0.3 |
| $I_A$-3 | 4.9 ± 0.1 |
| $I_A$-4 | 74.1 ± 2.7 |
| $I_A$-5 | 2.5 ± 0.3 |
| $I_A$-6 | 6.4 ± 0.1 |
| $I_A$-7 | 397.3 ± 20.3 |
| $I_A$-8 | 359.8 ± 57.8 |
| $I_A$-9 | >1000 |
| $I_A$-10 | >1000 |
| $I_A$-11 | 6.2 ± 0.5 |
| $I_A$-12 | >1000 |
| $I_A$-13 | 9.45 ± 0.75 |
| $I_A$-14 | >1000 |
| $I_A$-15 | 15.8 ± 2.8 |
| $I_A$-16 | 9.5 ± 3.2 |
| $I_A$-17 | >1000 |
| $I_A$-18 | >1000 |
| $I_A$-19 | >1000 |
| $I_A$-20 | >1000 |
| $I_A$-21 | 9.9 ± 1.8 |
| $I_A$-22 | >1000 |
| $I_A$-23 | >1000 |
| $I_A$-24 | 80.1 ± 4.7 |
| $I_A$-25 | 2 ± 0.1 |
| $I_A$-26 | 6.4 ± 0.6 |
| $I_A$-27 | >1000 |
| $I_A$-28 | >1000 |
| $I_A$-29 | >1000 |
| $I_A$-30 | >1000 |
| $I_A$-31 | 9.2 ± 0.4 |
| $I_A$-32 | >1000 |
| $I_A$-33 | >1000 |
| $I_A$-34 | >1000 |
| $I_A$-35 | >1000 |
| $I_A$-36 | 86.4 ± 0.6 |
| $I_A$-37 | >1000 |
| $I_A$-38 | >1000 |
| $I_A$-39 | >1000 |
| $I_A$-40 | >1000 |
| $I_A$-41 | 52.1 ± 0.8 |
| $I_B$-1 | >1000 |
| $I_B$-2 | >1000 |
| $I_B$-3 | >1000 |
| $I_C$-1 | >1000 |
| $I_D$-1 | >1000 |
| $I_E$-1 | >1000 |
| $I_F$-1 | 70.3 ± 5.2 |
| $I_F$-2 | 95.3 ± 1.6 |

It can be seen from Table 1 that most of the compounds of Formula I of the invention have a strong inhibitory activity against staphyloxanthin synthesis, indicating that the compounds of the invention can be developed into novel antibacterial drugs targeting synthesis of staphyloxanthin, a virulence factor in S. aureus s.

Example 65 Method and Results of $I_C50$ Determination Assay of Compound $I_A$-25 of the Invention with Respect to Activity of Inhibiting Staphyloxanthin Synthesis in Drug-Resistant Bacteria In addition to replacement of S. aureus strain Newman with USA 400 MW 2, USA 300 LAC and Mu 50, the rest of the method is the same as in Examples 58-59.

As shown in Table 2, it can be seen that Compound IA-25 of the invention not only inhibits staphyloxanthin synthesis in Staphylococcus aureus (strain Newman), but also has a potent inhibitory effect on drug-resistant strains USA400MW2, USA300LAC and Mu50.

TABLE 2

Data on inhibitory activity of benzofuran-3-alkylamine Compound $I_A$-25 on staphyloxanthin synthesis in drug-resistant strains ($IC_{50}$, nM)

| Drug-Resistant strain | $IC_{50}$ (nM) |
|---|---|
| USA400MW2 | 1.9 ± 0.5 |
| USA300LAC | 7.9 ± 1.2 |
| Mu50 | 0.8 ± 1.4 |

Example 66 Method and Results of $IC_{50}$ Determination Assay with Respect to Activity of Inhibiting Staphyloxanthin Synthesis in Drug-Resistant Strains in the Invention Compound $I_A$-25 was used as a representative compound. In addition to replacement of S aureus strain Newman with other MRSA strains as described in Table 3, the rest of the method is the same as in Examples 61-62.

The determination results are shown in Table 3, Compound IA-25 of the invention not only inhibits staphyloxanthin synthesis in Staphylococcus aureus (not limited to strain Newman), but also has a broad-spectrum potent inhibitory effects on drug-resistant strains.

TABLE 3

Data on inhibitory activity of benzofuran-3-alkylamine Compound $I_A$-25 on staphyloxanthin synthesis in drug-resistant strains ($IC_{50}$, nM) Inhibitory activity on staphyloxanthin $IC_{50}$ (nM)

| MRSA strain | $IC_{50}$ (nM) | MRSA strain | $IC_{50}$ (nM) |
|---|---|---|---|
| Newman | 2.0 ± 0.1 | MU50 (JPN) | 0.8 ± 0.01 |
| USA300 LAC (USA) | 7.9 ± 0.2 | USA400 MW2 (USA) | 1.9 ± 1.2 |
| NRS271 (SPA) | 0.4 ± 0.01 | NRS70 (JPN) | 1.7 ± 0.01 |
| NRS100 (USA) | 1.2 ± 0.1 | LRSA205 (CHN) | 10.5 ± 0.4 |
| NRS108 (FRA) | 5.6 ± 0.02 | HS663 (CHN) | 0.02 ± 0.01 |
| LRSA56 (CHN) | 1.8 ± 0.1 | NF65Y (CHN) | 1.0 ± 0.02 |
| LRSA202 (CHN) | 1.6 ± 0.2 | XN108 (CHN) | 0.2 ± 0.04 |

All documents mentioned in the invention are incorporated herein by reference as if each of them is individually incorporated by reference. Further, it should be understood that those skilled in the art, upon reading the above disclosure of the invention, can make various changes or modifications in the invention, and such equivalents also fall within the scope of the invention as defined by the appended claims.

Example 67 Method and Results of Determination of Inhibition of CrtN Enzyme Activity in the Invention Compound $I_A$-25 was used as a representative compound.

(1) Preparation of Diapophytoene Emulsion as Substrate

Overnight cultured pet28a::crtM/*E. coli* (DE3) was inoculated to 50 mL of fresh and sterile LB (containing kanamycin at a concentration of 50 μg/mL) in a ratio of 1:100 (bacteria liquid:medium); after a culture at 37° C. and 250 rpm for 24 h, the bacterial cells were collected by centrifugation at 8000 g for 4 min and washed twice with PBS buffer; 20 mL of acetone was added to the bacterial cells, and the bacterial cells were vortexed for mixing so as to extract staphyloxanthin and the intermediate products thereof; thereafter, 10 mL of n-hexane and 10 mL of an aqueous solution of NaCl (10%, mass/volume) were added to the extract, and vigorous shaking was carried out to remove the oily components in the extract; the hexane layer containing the staphyloxanthin and its intermediate products was collected, 10 mL of n-hexane was further added, and the extraction process was repeated once; the two hexane extracts were combined, dried over anhydrous magnesium sulfate and weighed; the obtained diapophytoene and phosphatidylcholine were dissolved in 200 μL of chloroform in a ratio of 1:3, and concentrated to dryness under vacuum; 2 mL of 0.02 M HEPES buffer (20 mM HEPES, pH 7.5; 500 mM NaCl) was added into each mixture of 8 mg of diapophytoene and 24 mg of phosphatidylcholine, followed by sonication in ice water until a homogeneous emulsion was formed.

(2) Assay of CrtN Enzyme Activity

Preparation of stock solutions of the relevant ingredients in the reaction system: FAD 10 mM; glucose 200 mM; glucose oxidase 2000 U/mL; catalase, dissolved in diapophytoene emulsion to 20000 U/mL. The above solutions were all prepared with 0.02 M HEPES buffer. The entire reaction system was 700 μL and the reaction was carried out in a 2 mL EP tube. The reaction system contained the following ingredients: 50 μL diapophytoene emulsion (containing catalase), 70 μL of compound solutions at different concentrations (prepared with distilled water) or distilled water, 262.5 μL 0.02 M HEPES buffer, 3.5 μL FAD solution, 7 μL glucose solution, 7 μL glucose oxidase solution. Finally 300 μL of pet28a::crtN/*E. coli* (DE3) whole cell lysate (~1.41 mg CrtN protein) was added to start the reaction. The reaction was carried out in a shaker at 37° C. and 250 rpm for 14 h.

(3) Extraction and Detection of Reaction Product

After completion of the reaction, the reaction was terminated by adding 500 μL of methanol, and the reaction solution was transferred to a 15 mL centrifuge tube; the reaction solution was added with 700 μL of chloroform, and vortexed thoroughly to extract the reacted staphyloxanthin, and then centrifuged at 7000 rpm for 3 min, and the chloroform layer was carefully pipetted; the remaining reaction solution was extracted by further adding 500 μL of chloroform thereto, and the extracts were combined and concentrated to dryness under vacuum; the concentrated product was dissolved by adding 200 μL of chloroform, and pipetted into a 96-well microplate, and then the absorbance was measured at 450 nm for quantification of the CrtN product diaponeurosporene. $IC_{50}$ is defined as the corresponding concentration of Compound $I_A$-25 at which 50% of CrtN activity is inhibited under laboratory conditions; the dose-effect relationship curve of CrtN enzyme activity was plotted in Graphpad 5.0.

In view of the excellent performance in staphyloxanthin inhibition assay, Compound $I_A$-25 was used as a representative compound for the study on enzyme inhibitory activity, and the enzyme inhibitory activity of Compound $I_A$-25 is measured to be $IC_{50}$=372.6 nM according to the above method for enzyme assay.

Example 68 Method and Results of Verification Assay Using CrtN as a Target in the Invention Compound $I_A$-25 was used as a representative compound. 6 strains for assay were set: wild-type *S. aureus* Newman strain, crtM mutant strain, crtN mutant strain, crtN mutant strain containing complementary crtN genome (crtN-C), naftifine hydrochloride-administration stain and Compound $I_A$-25-administration stain; carotenoid extract was analyzed by high performance liquid chromatography at a wavelength of 440 nm.

The specific operations were as follows:

Analysis on isoprene: *S. aureus* strain which had been cultured overnight in a test tube was added into 50 mL of fresh TSB medium, 100 μM naftifine hydrochloride and Compound $I_A$-25 was or not added in accordance with the instructions; culture was carried out at 37° C. and 250 rpm for 24 h, and the strains were collected by centrifugation and removal of the supernatant; the strains was washed twice with PBS buffer, and re-suspended in 500 μL of 1×TE (10 mM Tris, pH 8.5 and 1 mM EDTA) buffer; the suspension was added with lysostaphin (final concentration of 50 μg/mL), and incubated at 37° C. for 30 min; after 20 mL of methanol/0.3% aqueous sodium chloride solution (10:1, v/v) was added, the suspension was vortexed for mixing; subsequently, an equal amount of n-hexane was added twice for extraction, and the combined extracts were concentrated with a rotary evaporator; finally, the extract was re-dissolved in 500 μL of methanol/2-isopropanol, and then filtered; 50 μL of the sample was taken for analysis by high performance liquid chromatography (Agilent 1260) using a Shim-pack CLC-ODS reverse phase column (228-00808-91) (6 mm×150 mm; mobile phase: methanol/2-isopropanol, 1:1 (v/v), flow rate: 1 mL/min).

Analysis on carotenoid extract: *S. aureus* strain which had been cultured in a test tube overnight was added into 50 mL of fresh TSB medium, and 100 μM naftifine hydrochloride and Compound $I_A$-25 was added or not in accordance with the instructions; the culture was carried out at 37° C. and 250 rpm for 24 h, the strains were collected by centrifugation and removal of the supernatant; the strains were added with 20 mL of acetone, 10 mL of n-hexane and 10 mL of aqueous solution of sodium chloride (10:1, v/v); the mixture was shaken vigorously to remove the oily components in the extract, and the carotenoid extract was contained in the n-hexane layer; the extract was dried over anhydrous magnesium sulfate and concentrated using a rotary evaporator; finally, the extract was re-dissolved by adding 500 μL of methanol/2-isopropanol (85:15, v/v); the dissolved extract was filtered, and 50 μL of the sample was taken for analysis by high performance liquid chromatography (Agilent 1260, PAD detector) using a Spherisorb ODS2 column (250 mm×4.6 mm; mobile phase: methanol/2-isopropanol, 85:15 (v/v); flow rate: 1 mL/min).

Figure 3:
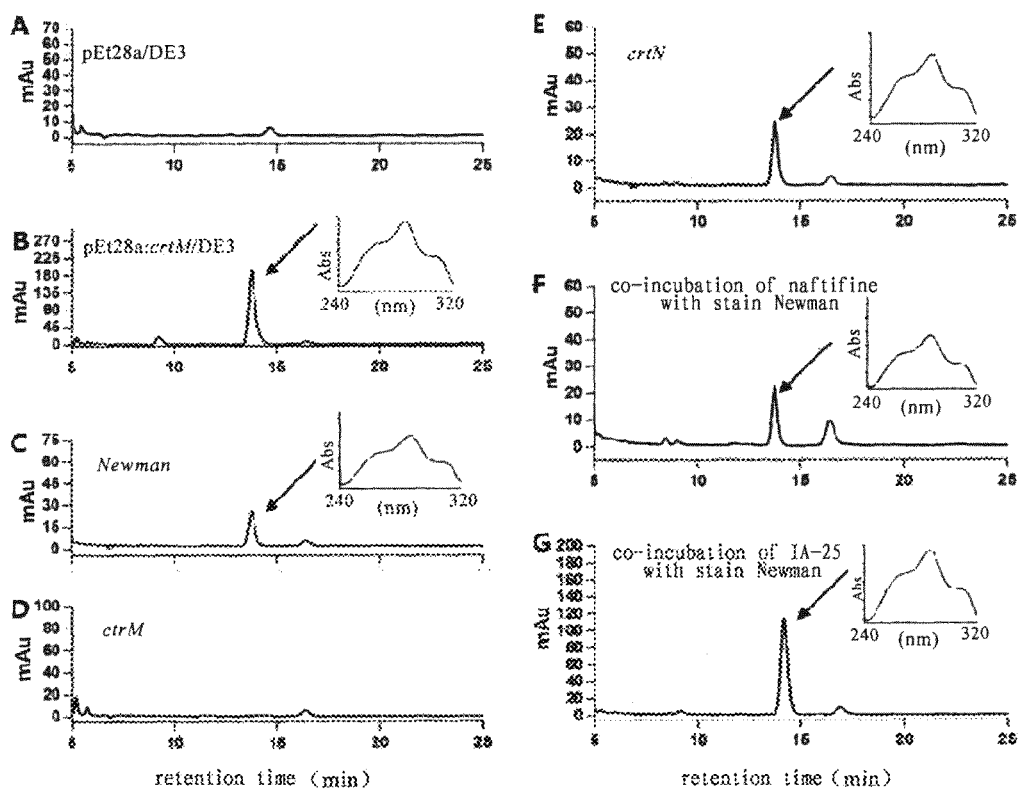
FIG. 3 shows the results of verification assay of Compound $I_A$-25 on the target CrtN.

As shown in FIG. 3, some visible absorption peaks were observed in the liquid phase spectrum of wild-type *S. aureus* Newman strain, which disappeared in the liquid phase spectrums of crtM mutant strain and crtN mutant strain, indicating that enzymes CrtM and CrtN were essential for the production of substance showing these peaks. The above results are consistent with that of recurrence of these liquid phase absorption peaks for crtN mutant strain containing complementary crtN genome. When naftifine hydrochloride or Compound $I_A$-25 was added to wild-type strain Newman, the absorption peaks at the original peak position disappeared again. These results indicate that naftifine hydrochloride or Compound $I_A$-25 exerts an inhibitory effect on the production of staphyloxanthins by inhibiting enzymes CrtM and CrtN simultaneously, or one of them.

Example 69 Method and Results of In Vitro Immunological Killing Assay According to the Invention Compound $I_A$-25 was used as a representative compound. The main object of the invention was to impair the ability of bacteria to resist immunological killing in vivo by inhibiting staphyloxanthins synthesis. The invention achieved the above object by designing an in vitro immunological killing assay on Compound $I_A$-25, and the specific procedure was as follows:

Hydrogen peroxide killing assay: Compound $I_A$-25 was added at a particular concentration to a sterile test tube, a S. aureus bacteria liquid which had been cultured overnight was added in a ratio of inoculum:medium=1:100, the culture was carried at 37° C. and 250 rpm for 24 h, 500 μL of the bacteria liquid was pipetted and centrifuged to collect the bacterial cells, and the bacterial cells were washed twice with PBS buffer; then, 500 μL of PBS was added, and the bacterial cells were re-suspended by thorough vortexing; 15 μL of the bacteria liquid was pipetted and added into 1500 μL of PBS buffer, and thorough vortexing was carried out for mixing (OD=~0.1); 250 μL of the mixed bacteria liquid was added to a 2 mL EP tube, and 10 μL of 37% hydrogen peroxide solution was added so that the final concentration of hydrogen peroxide in the bacteria liquid is 1.5%; after addition of hydrogen peroxide, the EP tube was capped with sealing film, and incubated at 37° C. and 250 rpm for 1 h for performing killing; another 250 μL of the mixed bacteria liquid was added with 10 μL of sterile PBS buffer as a control; after completion of the reaction, 5 μL of prepared catalase solution (the stock solution: 20000 U/mL, prepared with PBS buffer solution) was added, and vortexed thoroughly for mixing so as to decompose residual hydrogen peroxide; 100 μL of the reaction solution was added into 900 μL of sterile PBS buffer for 10-fold dilution and so on, until $10^6$-fold dilution; 10 μL of each of the above dilutions was added onto a TSA plate, then cultured overnight in a 37° C. incubator, and the viable colonies were counted. The calculated survival rate of bacteria after hydrogen peroxide killing=(count of bacteria grown in sample after hydrogen peroxide killing×dilution factor)/(count of bacteria grown in control group×dilution factor)×100%.

Human whole blood killing assay: Compound $I_A$-25 was added at a particular concentration into a sterile test tube, a bacteria liquid of S. aureus which had been cultured overnight was added in a ratio of inoculum:medium=1:100, the culture was carried at 37° C. and 250 rpm for 24 h, 500 μL of the culture liquid was pipetted and centrifuged to collect the bacterial cells, and the bacterial cells were washed twice with PBS buffer; then, 500 μL of PBS was added, and the cells were re-suspended by thorough vortexing; 15 μL of the bacteria liquid was pipetted and added into 1500 μL of PBS buffer, and thorough vortexing was carried out for mixing (OD=~0.1); then, 150 μL of bacteria liquid (OD=0.1) was added into 850 μL of sterile PBS buffer so that OD=0.015 for later use; fresh venous blood from healthy human body was collected with BD VACUTAINER PT tube, 360 μL fresh blood and 40 μL bacteria liquid (OD=~0.015) were added into a sterile glass test tube successively, then the incubation was carried out at 37° C. and 250 rpm for 6 h, 50 μL of the reaction liquid was added into 450 μL of sterile PBS buffer for 10-fold dilution, and so on, until $10^6$-fold dilution; another bacteria liquid of OD=~0.015 was taken as a control, and subject to 10-fold dilution, and so on, until $10^6$-fold dilution; 10 μL of each of the above dilutions was added onto a TSA plate, then cultured overnight in a 37° C. incubator, and the viable colonies were counted. The calculated survival rate of bacteria after blood killing=(count of bacteria grown in sample after blood killing×dilution factor)/(count of bacteria grown in control group×dilution factor)×100%.

Figure 4:
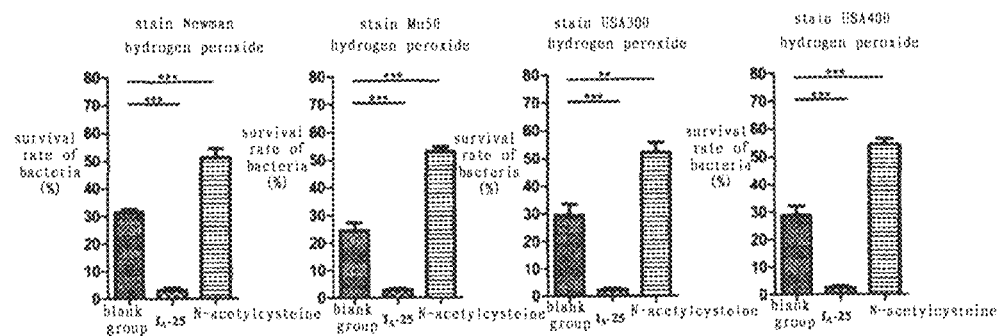
FIG. 4 shows the results of hydrogen peroxide killing assay.
Figure 5:
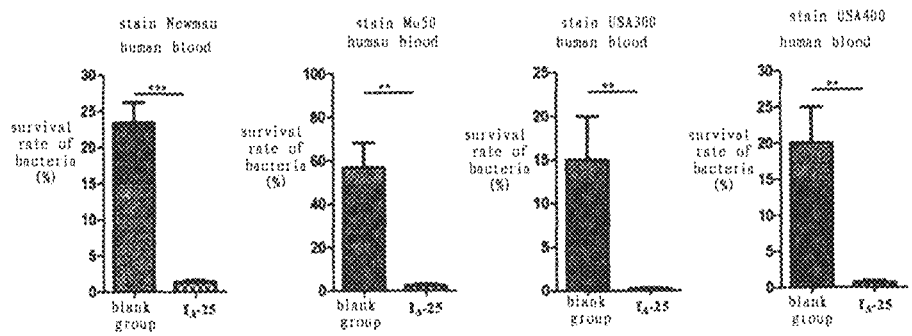
FIG. 5 shows the results of human blood killing assay.

The same procedure was applicable to other MRSA strains, and the assay results were shown in FIGS. 4 and 5.

Compound $I_A$-25 showed an excellent effect in the in vitro immunological killing assay. In the hydrogen peroxide killing assay, the survival rates of bacteria in the negative groups of the four strains were greater than 20%, while in the groups in which Compound $I_A$-25 was involved, the bacterial survival rates were less than 5%, and there were significant differences. Similarly, in the human blood killing assay, the survival rates of bacteria in the negative groups of the four strains were greater than 15%, while in the groups in which Compound $I_A$-25 was involved, the bacterial survival rates were less than 3%, and there were significant differences. This directly proved that Compound $I_A$-25 can effectively impair the ability of S. aureus to resist immunological killing in vivo.

Example 70 Method and Results of In Vitro Bacterial Growth Assay According to the Invention Compound $I_A$-25 was used as a representative compound. The main object of the invention is to impair the ability of bacteria to resist immunological killing in vivo by inhibiting staphyloxanthins synthesis, and the compounds according to the invention do not have the ability to kill bacteria themselves. The invention achieved the above object by designing an assay method of co-incubating Compound $I_A$-25 with MRSA strain, and the specific assay was as follows:

Compound $I_A$-25 was dissolved in a certain amount of DMSO to prepare a stock solution of a concentration of 20 mM; Compound $I_A$-25 was diluted with fresh TSB solution to a 1000 μL solution at a concentration of 0.2 mM or 0.5 mM; the dilution was placed in an environment of 37° C. for 2 h so as to fully dissolve naftifine hydrochloride; 100 μL of Compound $I_A$-25 dilution was added to a 96-well plate while the same volume of DMSO only was added as a negative control; an overnight culture of S. aureus strain was washed twice with PBS, then diluted with fresh medium to $OD_{600}$=1.0; 5 μL of the bacterial suspension was added to a 96-well plate so that the final bacterial concentration of OD600=~0.05; to prevent evaporation of the medium, 60 μL of liquid paraffin was added into a 96-well plate and incubated at 37° C. for 15 h; the value of OD600 was recorded with a microplate reader every half hour, and then a growth curve was plotted.

Figure 6:
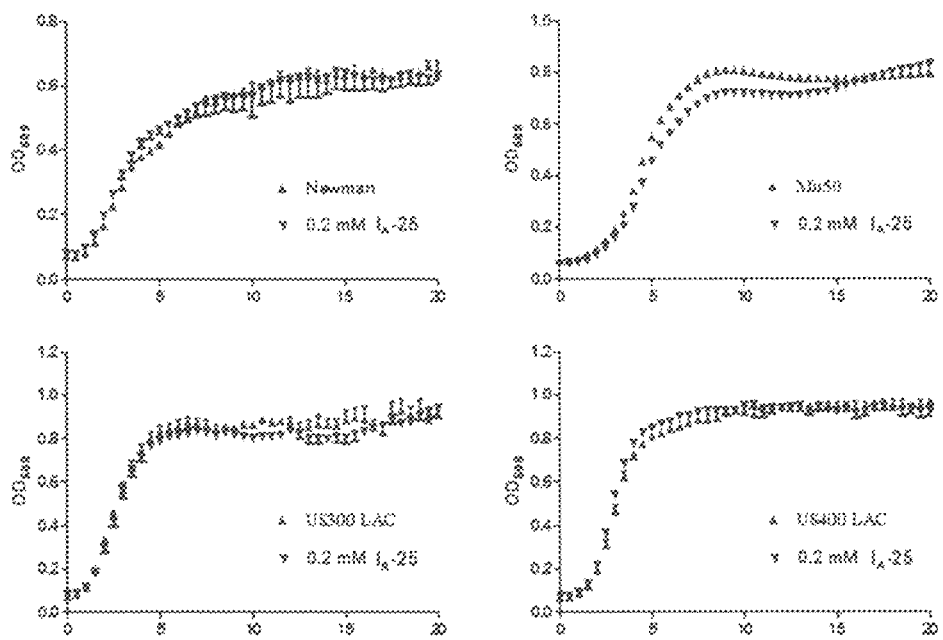
FIG. 6 shows the growth curves of bacteria.

As shown in FIG. 6, the trends of bacterial growth curve of the blank group and the administration group basically are consistent, indicating that the compounds according to the invention did not affect the growth and reproduction of bacteria.

Example 71 Method and Results of In Vitro Antifungal Assay According to the Invention As a representative compound, Compound $I_A$-25 was derived by structural modification of naftifine hydrochloride as a lead compound, thus whether Compound $I_A$-25 retains the antifungal activity of naftifine hydrochloride was further verified in the invention. In the invention, with Fluconazole, Voriconazole and Ketoconazole as positive controls, three strains which are sensitive to naftifine hydrochloride including *Tinea barbae*, *Microsporum gypseum* and *Trichophyton rubrum* were selected to determine in vitro antifungal activity of Compound $I_A$-25 by a micro liquid-based dilution method, which are described as follows:

Fluconazole (purchased from Pfizer Pharmaceutical Co., Ltd.), Voriconazole (purchased from Sigma) and Ketoconazole (purchased from Sigma) were used as controls. The concentration ranges of working solution of each drug were as follows: Fluconazole 0.125-64 µg/mL, and other compounds 0.0312-8 µg/mL. The fat-soluble drug was dissolved in dimethyl sulfoxide (DMSO) which had a concentration not more than 1%.

(1) Preparation of fungal suspension: prior to the assay, a small amount of *Candida albicans* was picked from a SDA plate preserved at 4° C., then inoculated into a glass tube containing 1 mL of YEPD culture medium, and a constant-temperature shaking culture was performed at 30° C. and 200 rpm for 24 h; 10 µL of the cultured fungal liquid was taken and inoculated into a glass tube containing 1 mL of YEPD culture medium, and was reactivated for 16 h under the same conditions, so that the fungi were at the late stage of exponential growth phase; the fungal suspension was diluted to an appropriate concentration with RPMI 1640, then counted using a hemocytometer, and the concentration of the fungal suspension was adjusted to a concentration of $(1-5) \times 10^3$ CFU/mL with RPMI 1640 medium, and inoculate the fungal suspension.

(2) Preparation of reaction plate for drug sensitivity: 100 µL of RPMI 1640 liquid medium was added into well No. 1 of each row in a sterile 96-well plate as a blank control; 100 µl of freshly prepared fungal suspension was added into wells No. 3-12 respectively; 198 µL of the fungal suspension and 2 µL of Compound $I_A$-25 solution to be tested were added into well No. 2 respectively; no drug but only 100 µL of the fungal suspension was added into well No. 12 as a positive growth control; wells No. 2-11 were subjected to doubling dilution so that the final drug concentrations of fluconazole in each well were 64 µg/mL, 32 µg/mL, 16 µg/mL, 8 µg/mL, 4 µg/mL, 2 µg/mL, 1 µg/mL, 0.5 µg/mL, 0.25 µg/mL and 0.125 µg/mL, respectively; the final drug concentrations of the other two compounds in each well were 8 µg/mL, 4 µg/mL, 2 µg/mL, 1 µg/mL, 0.5 µg/mL, 0.25 µg/mL, 0.125 µg/mL, 0.0625 µg/mL, 0.312 µg/mL, and 0.0156 µg/mL, respectively, and the tips were replaced after each concentration gradient was completed during the preparation process. A plate for drug sensitivity for quality control was prepared while each drug-sensitive plate was prepared, and each plate for drug-sensitive was incubated statically at 30° C. in a constant temperature and humidity incubator. The MIC reference value was as follows: $MIC_{80}$ value of FCZ is 2.0-8.0 µg/mL, and the experimental operation was considered to be accurate and reliable only when the MIC value was within the above range. If the test strains grew well at the same time, the assay was considered successful and the results were acceptable.

(3) Determination of minimum inhibitory concentration (MIC value): according to the standard M38-A2 protocol proposed by NCCLS, the lowest drug concentration corresponding to >80% growth inhibition is the MIC80 of the drug as compared with the growth control well. The results were determined by combining visual reading and a microplate reader. The OD value of each well was measured at 630 nm using a microplate reader. The OD value of the positive control well was controlled at about 0.2. Compared with the positive control well, the lowest drug concentration in the well in which the OD value decreased by 80% or more was $MIC_{80}$. The visual reading was terminated when the bacterial growth was invisible. Visual reading and determination using microplate reader was combined to avoid result error. When the $MIC_{80}$ value of a drug exceeded the measurable concentration range, the results were determined as follows: when the $MIC_{80}$ value was higher than the highest concentration of 64 µg/mL, the result was indicated as ">64 µg/mL"; when the MIC80 value of a drug was the lowest concentration or below the lowest concentration, the result was indicated as "<0.0312 µg/mL" with no difference. The above assay was performed in parallel 2 to 3 times, the result was accepted only when the $MIC_{80}$ value could be accurately repeated or differed by only one concentration level, and the higher concentration was taken as the $MIC_{80}$ value; when the MIC80 value differed by more than two concentration levels, the assay needed to be repeated until the requirements were met.

TABLE 4

Results of in vitro antifungal activity assay
Antifungal Activities, MIC80 (µg/mL)

| Compound | Trichophyton rubrum | Microsporum gypseum | Tinea barbae |
|---|---|---|---|
| Ketoconazole | 0.5 | 2 | 0.0625 |
| Voriconazole | 0.03125 | 0.25 | 0.03125 |
| Fluconazole | 1 | 8 | 2 |
| $I_A$-25 | 64 | 32 | >64 |

As shown in Table 4, Compound IA-25 lost antifungal activity.

Example 72 Method and Results of In Vivo Pharmacodynamics Evaluation Assay in Mice According to the Invention Compound $I_A$-25 was used as a representative compound. The laboratory SPF-grade female BALB/c mice were purchased from Shanghai Jiesijie Laboratory Animal Co., Ltd. and bred under aseptic condition to 6-8 weeks old. The *S. aureus* strains which had been cultured overnight were transferred to fresh and sterile TSB medium and cultured at 37° C. and 250 rpm for 3 h to exponential growth phase; the culture was washed twice with PBS buffer, and then suspended in PBS for later use. In the mouse infection assay, the mice were divided into several groups, each containing 10 mice. All mice were anesthetized by intraperitoneal injection of sodium pentobarbital (80 mg/kg), then the mice were infected by retroorbital injection of 100 µL of strain Newman or other MRSA strains, and the in vivo pharmacodynamic levels of Compound $I_A$-25 were determined by comparison with blank group and positive group.

TABLE 5

In vivo pharmacodynamics evaluation of Compound $I_A$-25 in mice

Viable colony counts of MRSA and Newman strains in vivo ($Log_{10}$CFU)

| | Newman | Mu50 | NRS271 | LRSA202 | LRSA56 | NF65Y | NRS108 |
|---|---|---|---|---|---|---|---|
| $I_A$-25 | 3.8 | 2.7 | 6.4 | 4.9 | 3.3 | 3.5 | 2.3 |
| Blank | 6.4 | 5.1 | 8.5 | 6.6 | 4.3 | 5.7 | 4.0 |
| Vancomycin | 4.3 | 5.4 | 6.5 | 5.3 | 3.8 | 4.6 | 2.4 |
| Linezolid | 4.9 | 3.1 | 8.3 | 4.6 | 4.6 | 5.1 | 2.3 |

As shown in Table 5, Compound IA-25 exhibited excellent antibacterial effects in terms of pharmacodynamics in mice, and was superior to the positive drug in some organs.

Example 73 Method and Results of Evaluation Assay of Liver Microsome Metabolism in Mice According to the Invention Compound $I_A$-25 was used as a representative compound.

The results of liver microsome metabolism assay showed that the half-life of the drug is between 50 min and 120 min, showing good pharmacokinetic properties, so it is suitable for various administration routes.

Example 74 Method and Results of Pharmacokinetics Assay According to the Invention Compound $I_A$-25 was used as a representative compound.

The results of pharmacokinetics assay showed that the bioavailability of the drug is between 15% and 45%, showing good pharmacokinetic properties, so it is further confirmed to be suitable for various administration routes.

Example 75 Method and Results of Inhibition Assay on hepaticCYP450 Enzyme According to the Invention Compound $I_A$-25 was used as a representative compound.

TABLE 6

Inhibition assay of Compound $I_A$-25 on hepatic CYP450 enzyme

| CYP enzyme subtype | Half inhibitory concentration of positive drug ($IC_{50}$, µM) | Half inhibitory concentration of $I_A$-25 ($IC_{50}$, µM) |
|---|---|---|
| 1A2 | 0.00 (α-naphthoflavone) | 5.69 |
| 2B6 | 0.12 (ticlopidine hydrochloride) | >10 |
| 2C8 | 0.11 (montelukast) | >10 |
| 2C9 | 0.24 (sulfaphenazole) | >10 |
| 2C19 | 3.88 (omeprazole) | >10 |
| 2D6 | 0.03 (quinidine) | 3.20 |
| 3A4M | 0.11 (ketoconazole) | >10 |
| 3A4T | 0.43 (ketoconazole) | >10 |

As shown in Table 6, Compound $I_A$-25 showed a very weak inhibitory activity on hepatic CYP450 enzyme, which initially demonstrated a lower hepatotoxicity of the compound.

Example 76 Method and Results of HERG Potassium Ion Channel Inhibition Assay According to the Invention Compound $I_A$-25 was used as a representative compound.

The results showed that the hERG inhibitory activity of Compound $I_A$-25 was greater than 40 µM, which initially demonstrated that the compound had a lower cardiotoxicity.

Example 77 Method and Results of Rat MTD Assay According to the Invention

Compound $I_A$-25 was used as a representative compound.

Thirty rats weighing 180-220 g, half male and half female, were picked out and randomly divided into three groups. The first group was administered Compound $I_A$-25 at a dose of 60 mg/kg, the second group was administered Compound $I_A$-25 at a dose of 250 mg/kg, and the third group was administered Compound $I_A$-25 at a dose of 1000 mg/kg. After a single administration, the rats were observed for 14 days, and dissected for observation on the 15th day.

The results showed that Compound $I_A$-25 at a single dose of 1000 mg/kg did not result in any death or poor behavior events in the rats, and there was not any abnormality in the dissected organs, which demonstrated that the compound had a less acute toxicity.

Example 78 Results of In Vitro Cytotoxicity Assay of the Selected Compound of the Invention

TABLE 7

Results of in vitro cytotoxicity assay of the compound

| | CC50 of compounds on cells (ug/ml) | |
|---|---|---|
| Compounds | HepG2 | HEK293 |
| $I_A$-25 | 41.19 | 18.69 |
| Amphotericin B | 2.956 | 3.923 |

The results showed that Compound $I_A$-25 exhibited a weaker in vitro cytotoxicity.

All documents mentioned in the present invention are incorporated herein by reference as if each of them is individually incorporated by reference. Further, it should be understood that those skilled in the art, upon reading the above disclosure of the invention, can make various changes or modifications in the invention, and such equivalents also fall within the scope of the invention as defined by the appended claims.

The invention claimed is:

1. A compound of Formula I, or a pharmaceutically acceptable salt thereof, or a stereoisomer thereof:

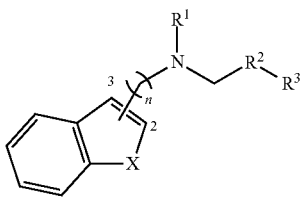

I in the Formula I:
X is S or O;
R¹ is H, or a substituted or unsubstituted $C_1$-$C_4$ linear or branched alkyl;
R² is a substituted or unsubstituted $C_1$-$C_3$ linear alkyl, a substituted or unsubstituted $C_3$-$C_8$ cycloalkyl, a substituted or unsubstituted $C_2$-$C_6$ linear or branched alkenyl, -(CH=CH)-p, or a substituted or unsubstituted $C_2$-$C_6$ linear or branched alkynyl, wherein p is a positive integer from 2 to 5;
R³ is a substituted or unsubstituted $C_1$-$C_3$ linear or branched alkyl, a substituted or unsubstituted $C_3$-$C_8$ cycloalkyl, a substituted or unsubstituted $C_3$-$C_7$ heteroaromatic ring group, or a substituted or unsubstituted $C_6$-$C_{10}$ aromatic ring group;
n is an integer from 1 to 3:
wherein, the group

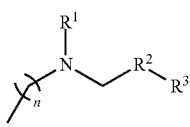

is located at position 2 or 3;
wherein, in R¹, R², and R³, the substitution means having 1, 2, 3 or 4 substituents selected from the group consisting of a $C_1$-$C_6$ linear or branched alkyl, a $C_1$-$C_6$ haloalkyl, halogen, nitro, cyano, a $C_1$-$C_4$ linear or branched alkoxy, a -(C=O)-O-$C_1$-$C_4$ alkyl, a $C_6$-$C_{10}$ aromatic ring group, and a $C_3$-$C_8$ cycloalkyl.

2. The compound of Formula I, or a pharmaceutically acceptable salt thereof, or a stereoisomer thereof according to claim 1, characterized in that the R¹ is H, methyl, ethyl or isopropyl.

3. The compound of Formula I, or a pharmaceutically acceptable salt thereof, or a stereoisomer thereof according to claim 1, characterized in that the R² is vinyl, cyclopropyl, ethynyl or (CH=CH)-p, where p is a positive integer from 2 to 3.

4. The compound of Formula I, or a pharmaceutically acceptable salt thereof, or a stereoisomer thereof according to claim 1, characterized in that the R³ is a substituted $C_4$-$C_7$ cycloalkyl, a substituted $C_5$-$C_6$ heteroaromatic ring group, or a substituted $C_6$-$C_{10}$ aromatic ring group, wherein the substitution means having 1, 2, 3 or 4 substituents selected from the group consisting of a $C_1$-$C_6$ alkyl, -$CF_3$, halogen, nitro, or a $C_1$-$C_4$ linear or branched alkoxy, and the number of substituents is an integer from 1 to 4.

5. The compound of Formula I, or a pharmaceutically acceptable salt thereof, or a stereoisomer thereof according to claim 1, characterized in that the substitution means having 1, 2, 3 or 4 substituents selected from the group consisting of a $C_1$-$C_3$ linear or branched alkyl, a $C_1$-$C_3$ perfluoroalkyl group, a $C_1$-$C_3$ linear or branched alkoxy, halogen or nitro, and the number of substituent is an integer from 1 to 4.

6. The compound of Formula I, or a pharmaceutically acceptable salt thereof, or a stereoisomer thereof according to claim 1, characterized in that the compound of Formula I is selected from the group consisting of:

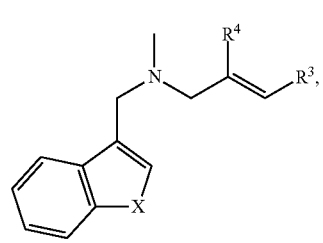

$I_A$

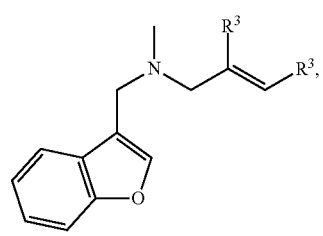

$I_B$

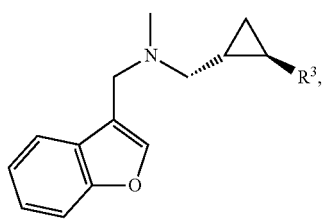

$I_C$

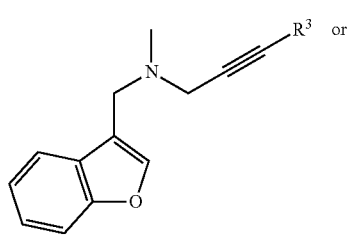

$I_D$

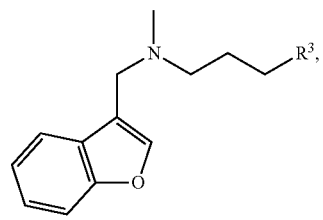

$I_E$ wherein X, R¹ and R³ are as defined in claim 1, and R⁴ is H, or a substituted or unsubstituted $C_1$-$C_3$ linear alkyl.

7. The compound of Formula I, or a pharmaceutically acceptable salt thereof, or a stereoisomer thereof according to claim 1, characterized in that the compound of Formula I is selected from the group consisting of:
(E)-N-methyl-N-[(benzofuran-3-yl)methylene]-3-phenyl-prop-2-en-1-amine;

(E)-N-methyl-N-[(benzofuran-3-yl)methylene]-3-(4-trifluoromethylphenyl)prop-2-en-1-amine;
(E)-N-methyl-N-[(benzofuran-3-yl)methylene]-3-(4-chlorophenyl)prop-2-en-1-amine;
(E)-N-methyl-N-[(benzofuran-3-yl)methylene]-3-(4-fluorophenyl)prop-2-en-1-amine;
(E)-N-methyl-N-[(benzofuran-3-yl)methylene]-3-(4-bromophenyl)prop-2-en-1-amine;
(E)-N-methyl-N-[(benzofuran-3-yl)methylene]-3-(4-difluoromethylphenyl)prop-2-en-1-amine;
(E)-N-methyl-N-[(benzofuran-3-yl)methylene]-3-(4-cyclopentyl)prop-2-en-1-amine;
(E)-N-methyl-N-[(benzofuran-3-yl)methylene]-3-(2-chlorophenyl)prop-2-en-1-amine;
(E)-N-methyl-N-[(benzofuran-3-yl)methylene]-3-(3-fluoro-4-trifluoromethylphenyl)prop-2-en-1-amine;
(E)-N-methyl-N-[(benzofuran-3-yl)methylene]-3-(naphthalen-1-yl)prop-2-en-1-amine;
(E)-N-methyl-N-[(benzofuran-3-yl)methylene]-3-(2,4-dichlorophenyl)prop-2-en-1-amine;
(E)-N-methyl-N-[(benzofuran-3-yl)methylene]-3-(3-chlorophenyl)prop-2-en-1-amine;
(E)-N-methyl-N-[(benzofuran-3-yl)methylene]-3-(4-methylcarboxylate phenyl)prop-2-en-1-amine;
(E)-N-methyl-N-[(benzofuran-3-yl)methylene]-3-(furan-2-yl)-prop-2-en-1-amine;
(E)-N-methyl-N-[(benzofuran-3-yl)methylene]-3-(4-methoxyphenyl)-prop-2-en-1-amine;
(E)-N-methyl-N-[(benzofuran-3-yl)methylene]-3-(4-nitrophenyl)-prop-2-en-1-amine;
(E)-N-methyl-N-[(benzofuran-3-yl)methylene]-3-(4-ethoxyphenyl)-prop-2-en-1-amine;
(E)-N-methyl-N-[(benzofuran-3-yl)methylene]-3-(3-trifluoromethylphenyl)-prop-2-en-1-amine;
(E)-N-methyl-N-[(benzofuran-3-yl)methylene]-3-(3-fluorophenyl)-prop-2-en-1-amine;
(E)-N-methyl-N-[(benzofuran-3-yl)methylene]-3-(3-methoxyphenyl)-prop-2-en-1-amine;
(E)-N-methyl-N-[(benzofuran-3-yl)methylene]-3-(4-methylphenyl)-prop-2-en-1-amine;
(E)-N-methyl-N-[(benzofuran-3-yl)methylene]-3-(2-nitrophenyl)-prop-2-en-1-amine;
(E)-N-methyl-N-[(benzofuran-3-yl)methylene]-but-2-en-1-amine;
(E)-N-methyl-N-[(benzofuran-3-yl)methylene]-3-(4-cyanophenyl)-prop-2-en-1-amine;
(E)-N-methyl-N-[(benzofuran-3-yl)methylene]-3-(4-phenylphenyl)-prop-2-en-1-amine;
(E)-N-methyl-N-[(benzofuran-3-yl)methylene]-3-(2-naphthyl)-prop-2-en-1-amine;
(E)-N-methyl-N-[(benzofuran-3-yl)methylene]-3-(4-tert-butylphenyl)-prop-2-en-1-amine;
(E)-N-methyl-N-[(benzofuran-3-yl)methylene]-3-(2-fluorophenyl)-prop-2-en-1-amine;
(E)-N-methyl-N-[(benzofuran-3-yl)methylene]-3-(3-nitrophenyl)-prop-2-en-1-amine;
(E)-N-methyl-N-[(benzofuran-3-yl)methylene]-3-(2-trifluoromethylphenyl)-prop-2-en-1-amine;
(E)-N-methyl-N-[(benzofuran-3-yl)methylene]-3-(2-fluoro-4-trifluoromethylphenyl)-prop-2-ene-1-amine;
(E)-N-methyl-N-[(benzofuran-3-yl)methylene]-3-cyclopentylprop-2-en-1-amine;
(E)-N-methyl-N-[(benzofuran-3-yl)methylene]-3-thiophen-2-en-1-amine;
(E)-N-methyl-N-[(benzofuran-3-yl)methylene]-3-(2-methoxyphenyl)-prop-2-en-1-amine;
(E)-N-methyl-N-[(benzofuran-3-yl)methylene]-3-(2-fluoro-4-methoxyphenyl)-prop-2-en-1-amine;
(E)-N-methyl-N-[(benzofuran-3-yl)methylene]-3-(2-methylphenyl)-prop-2-en-1-amine;
(E)-N-methyl-N-[(benzofuran-3-yl)methylene]-3-(3-methylphenyl)-prop-2-en-1-amine;
(E)-N-methyl-N-[(benzofuran-3-yl)methylene]-3-(3-fluoro-4-methoxyphenyl)-prop-2-en-1-amine;
(E)-N-methyl-N-[(benzothiophen-3-yl)methylene]-3-(3-fluoro-4-methoxyphenyl)-prop-2-en-1-amine;
(E)-N-[(benzofuran-3-yl)methylene]-3-(4-trifluoromethylphenyl)-prop-2-en-1-amine;
(E)-N-ethyl-N-[(benzofuran-3-yl)methylene]-3-(4-trifluoromethylphenyl)-prop-2-en-1-amine;
(E)-N-isopropyl-N-[(benzofuran-3-yl)methylene]-3-(4-trifluoromethylphenyl)-prop-2-en-1-amine;
N-methyl-N-[(benzofuran-7-yl)methylene]-1-[(1S,2S)-2-phenylcyclopropyl]-methylamine;
N-methyl-N-[(6,7,8,9-tetrahydro-5H-benzo[3]annulen-2-yl)methyl]-3-(4-phenylphenyl)-prop-2-yn-1-amine;
N-methyl-N-[(6,7,8,9-tetrahydro-5H-benzo[3]annulen-2-yl)methylene]-3-phenyl-prop-1-amine;
(E)-N-methyl-N-[(benzofuran-2-yl)methylene]-3-(4-phenylphenyl)-prop-2-en-1-amine; or
(E)-N-methyl-N-[(benzothiophen-2-yl)methylene]-3-(4-phenylphenyl)-prop-2-en-1-amine.

8. A pharmaceutical composition comprising:
(1) the compound, or a pharmaceutically acceptable salt thereof, or a stereoisomer thereof according to claim 1 as an active ingredient; and
(2) a pharmaceutically acceptable carrier.

9. An antibacterial drug comprising:
(1) the compound, or a pharmaceutically acceptable salt thereof, or a stereoisomer thereof according to claim 1;
(2) an additional antibiotic; and
(3) a pharmaceutically acceptable carrier.

10. A method for treating infectious diseases caused by Staphylococcus aureus, comprising administering to a patient in need a therapeutically effective amount of the compound of Formula I or pharmaceutically acceptable salts thereof according to claim 1.

* * * * *